United States Patent
Harding

(10) Patent No.: US 10,040,864 B2
(45) Date of Patent: Aug. 7, 2018

(54) ANTI-OX40 ANTIBODIES AND THEIR USES

(71) Applicant: AbbVie Biotherapeutics Inc., Redwood City, CA (US)

(72) Inventor: Fiona A. Harding, Mountain View, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 0 days.

(21) Appl. No.: 15/908,221

(22) Filed: Feb. 28, 2018

(65) Prior Publication Data

US 2018/0194855 A1 Jul. 12, 2018

Related U.S. Application Data

(63) Continuation of application No. 15/843,281, filed on Dec. 15, 2017.

(60) Provisional application No. 62/434,761, filed on Dec. 15, 2016.

(51) Int. Cl.
| | |
|---|---|
| *C07K 16/28* | (2006.01) |
| *A61K 39/395* | (2006.01) |
| *C07K 16/30* | (2006.01) |
| *C12N 15/85* | (2006.01) |
| *A61P 35/00* | (2006.01) |

(52) U.S. Cl.
CPC .......... *C07K 16/3023* (2013.01); *A61P 35/00* (2018.01); *C07K 16/2875* (2013.01); *C07K 16/2896* (2013.01); *C12N 15/85* (2013.01); *C07K 2317/56* (2013.01)

(58) Field of Classification Search
None
See application file for complete search history.

(56) References Cited

U.S. PATENT DOCUMENTS

| | | | |
|---|---|---|---|
| 7,504,101 | B2 | 3/2009 | Weinberg |
| 9,738,723 | B2 | 8/2017 | Hammond |
| 2006/0281072 | A1 | 12/2006 | Bakker |
| 2008/0286286 | A1 | 11/2008 | Liu |
| 2010/0166740 | A1 | 7/2010 | Endl |
| 2013/0280275 | A1 | 10/2013 | Liu |
| 2015/0307617 | A1 | 10/2015 | Du |

FOREIGN PATENT DOCUMENTS

| | | |
|---|---|---|
| EP | 1060247 B1 | 8/1999 |
| EP | 1060247 B2 | 8/1999 |
| WO | 199942585 A1 | 8/1999 |
| WO | 2003106498 A2 | 12/2003 |
| WO | 2005017148 A1 | 2/2005 |
| WO | 2007084559 A2 | 7/2007 |
| WO | 2012027328 A2 | 3/2012 |
| WO | 2016073380 A1 | 5/2016 |
| WO | 2017096281 A1 | 6/2017 |

OTHER PUBLICATIONS

Aspeslagh et al., 2016 "Rationale for anti-OX40 cancer immunotherapy," Eur J Cancer 52:50-66.
Baruah et al., 2012 "Decreased levels of alternative co-stimulatory receptors OX40 and 4-1BB characterise T cells from head and neck cancer patients," Immunobiology 217(7):669-675.
Baumann et al., 2004 "Functional expression of CD134 by neutrophils," Eur J Immunol 34(8): 2268-2275.
Bodmer, et al., 2002 "The molecular architecture of the TNF superfamily," Trends Biochem Sci 27(1):19-26.
Bulliard et al., 2014 "OX40 engagement depletes intratumoral Tregs via activating FcgammaRs, leading to antitumor efficacy," Immunol Cell Biol 92(6):475-80.
Croft, 2010 "Control of immunity by the TNFR-related molecule OX40 (CD134)," Annu Rev Immunol 28:57-78.
Curti et al., 2013 "OX40 is a potent immune-stimulating target in late-stage cancer patients," Cancer Res 73(24):7189-7198.
Gonzalez et al. 2016 "INCAGN01949: A novel anti-OX40 agonist antibody with the potential to enhance tumor specific T-cell responsiveness, while selectively depleting intratumoral regulatory T cells," Poster 3204, American Association for the Cancer Research Annual Meeting, New Orleans, LA USA, Apr. 16-20, 2016.
Gramaglia et al., 1998 "OX40 ligand: a potent costimulatory molecule for sustaining primary CD4 T cell responses," J Immunol 161(12):6510-6517.
Guo et al., 2014 "PD-1 blockade and OX40 triggering synergistically protects against tumor growth in a murine model of ovarian cancer," PLoS One 9(2):e89350.
Karulf et al., 2010 "OX40 ligand regulates inflammation and mortality in the innate immune response to sepsis," J Immunol 185(8): 4856-4862.
Kitamura et al., 2009 "OX40 costimulation can abrogate Foxp3+ regulatory T cell-mediated suppression of antitumor immunity," Int J Cancer 125(3):630-638.
Kjaergaard et al., 2000 Therapeutic Efficacy of OX-40 Receptor Antibody Depends on Tumor Immunogenicity and Anatomic Site of Tumor Growth, Cancer Res 60(19):5514-5521.
Kovacsovics-Bankowski et al., 2013 "Phase I/II clinical trial of anti-OX40, radiation and cyclophosphamide in patients with prostate cancer: immunological analysis," Journal for ImmunoTherapy of Cancer 1(Suppl 1):P255.
Ladanyi et al., 2004 "T-cell activation marker expression on tumor-infiltrating lymphocytes as prognostic factor in cutaneous malignant melanoma," Clin Cancer Res 10(2):521-530.
Marabelle et al., 2013 "Depleting tumor-specific Tregs at a single site eradicates disseminated tumors," J Clin Invest 123(6):2447-2463.
Jetty et al., 2002 "Survival in human colorectal cancer correlates with expression of the T-cell costimulatory molecule OX-40 (CD134)," Am J Surg 183(5):512-518.
Piconese et al., 2008 "OX40 triggering blocks suppression by regulatory T cells and facilitates tumor rejection," J Exp Med 205(4):825-839.
Ramstad et al., 2000 "Immunohistochemical analysis of primary breast tumors and tumor-draining lymph nodes by means of the T-cell costimulatory molecule OX-40," Am J Surg 179(5):400-409.
Rogers et al.,2001 "OX40 promotes Bcl-xL and Bcl-2 expression and is essential for long-term survival of CD4 T cells," Immunity 15(3):445-455.

(Continued)

*Primary Examiner* — Ilia I Ouspenski
(74) *Attorney, Agent, or Firm* — Dechert LLP

(57) ABSTRACT

The present disclosure provides novel anti-OX40 antibodies, compositions including the antibodies, nucleic acids encoding the antibodies, and methods of making and using the same.

18 Claims, 9 Drawing Sheets

(56) References Cited

OTHER PUBLICATIONS

Figure 1A:
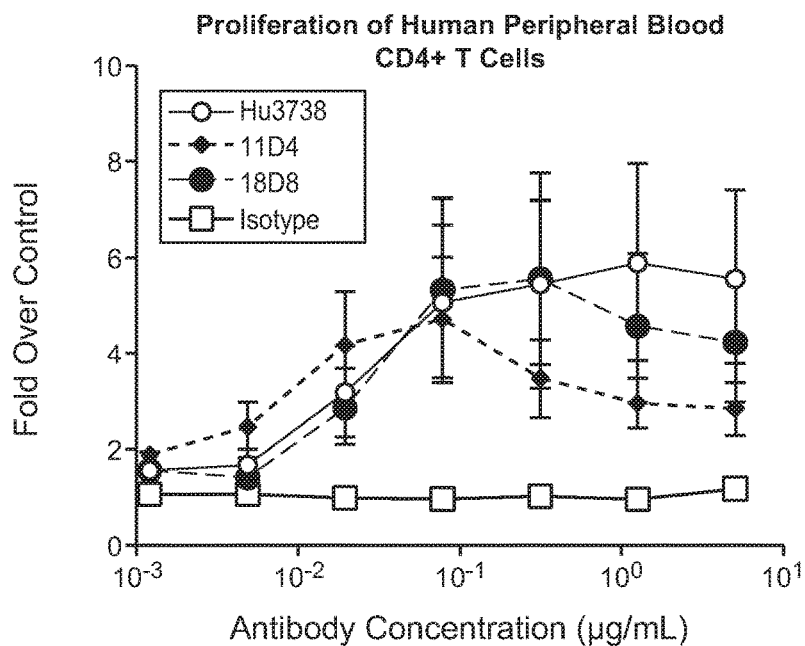

Ruby et al., 2009 "Cutting Edge: OX40 agonists can drive regulatory T cell expansion if the cytokine milieu is right." J Immunol 183(8):4853-4857.

Sarff et al., 2008 "OX40 (CD134) expression in sentinel lymph nodes correlates with prognostic features of primary melanomas," Am J Surg 195(5):621-625.

So et al., 2007 "Cutting edge: OX40 inhibits TGF-beta- and antigen-driven conversion of naive CD4 T cells into CD25+Foxp3+ T cells," J Immunol 179(3):1427-1430.

So et al., 2011 "Antigen-independent signalosome of CARMA1, PKCtheta, and TNF receptor-associated factor 2 (TRAF2) determines NF-kappaB signaling in T cells," Proc Natl Acad Sci U S A 108(7):2903-2908.

Song et al., 2005 "Sustained survivin expression from OX40 costimulatory signals drives T cell clonal expansion," Immunity 22(5):621-631.

Soroosh et al., 2007 "Differential requirements for OX40 signals on generation of effector and central memory CD4+ T cells," J Immunol 179(8):5014-5023.

Voo et al., 2013 "Antibodies Targeting Human OX40 Expand Effector T Cells and Block Inducible and Natural Regulatory T Cell Function," J Immunol 191(7):3641-3650.

Vu et al., 2007 "OX40 costimulation turns off Foxp3+ Tregs," Blood 110(7):2501-2510.

Weinberg et al., 2000 "Engagement of the OX-40 Receptor In Vivo Enhances Antitumor Immunity," J Immunol 164(4):2160-2169.

Weinberg et al., 2006 "Anti OX40 (CD134) Administration of Nonhuman Primates: Immunostimulatory Effects and Toxicokinetic Study," J Immunother 29(6):575-585.

International Search Report and Written Opinion dated May 3, 2018 corresponding to related International Patent Application No. PCT/US2017/066680.

Signal Sequence
[CRDI]
[CRDII]
[CRDIII]
[CRDIV]
[Transmembrane]

human  MCVGARRLGRGPCAALLLLGLGLS-TVTGL HCVGDTYPSNDRCCHECRPGNGMVSRCSRS
mouse  MY----VWVQQPTALLLLLGLTLGVTARRL NCVKHTYPSGHKCCRECQPHGMVSRCDHT human  QNTVCR PCGPGFYNDVVSSKPCKPCTWCNLRSGSERKQLCTATQDTVC RCRAGTQPLD--
mouse  RDTLCH PCETGFYNEAVNYDTCKQCTQCNHRSGSELKQNCTPTQDTVC RCRPGTQPRQDS human  SYKPGVDCA PPGHFSPGDNQACKPWTNCTLAGKHTLQPASNSSDAIC EIDRDPPATQPQ
mouse  GYKLGVDCV PPGHFSPGNNQACKPWTNCTLSGKQTRHPASDSLDAVC EDRSLLATLLW human  ETQGPPARPITVQPTEAWPRTSQPSTRPVEVPGGRAVAA ILGLIGLVLGLLGPLAILLAL
mouse  ETQRPTFRPTTVQSTTVWPRTSELPSPPTLVTPEGPA FAVLLGLG--LGLLAPLTVLLAL human  YLL RRDQRLPPDAHKPPGGGSFRTPIQEEQADAHSTLAKI  (SEQ ID NO:1)
mouse  Y LLRKAWRLPN-TPKPCWGNSFRTPIQEEHTDAHFTLAKI  (SEQ ID NO:3)

FIG. 4A

ANTI-OX40 ANTIBODIES AND THEIR USES

1. CROSS REFERENCE TO RELATED APPLICATIONS

This application is a continuation of U.S. application Ser. No. 15/843,281, filed Dec. 15, 2017, which claims the benefit under 35 U.S.C. § 119(e) of U.S. Provisional Application Ser. No. 62/434,761, filed Dec. 15, 2016, the contents of which are incorporated herein in its entirety by reference thereto.

2. SEQUENCE LISTING

The instant application contains a Sequence Listing which has been submitted electronically in ASCII format and is hereby incorporated by reference in its entirety. Said ASCII copy, created on Oct. 30, 2017, is named 381493-368US-_SL.txt and is 96,788 bytes in size.

3. TECHNICAL FIELD

The present application pertains to, among other things, novel anti-OX40 antibodies, compositions including the antibodies, nucleic acids encoding the antibodies, and methods of making and using the same.

4. BACKGROUND

Cancer therapies comprise a wide range of therapeutic approaches, including surgery, radiation, and chemotherapy. While the various approaches allow a broad selection of treatments to be available to the medical practitioner to treat the cancer, existing therapeutics suffer from a number of disadvantages, such as a lack of selectivity of targeting cancer cells over normal, healthy cells, and the development of resistance by the cancer to the treatment.

Recent approaches based on targeted therapeutics, which interfere with cellular processes of cancer cells preferentially over normal cells, have led to chemotherapeutic regimens with fewer side effects as compared to non-targeted therapies such as radiation treatment.

Cancer immunotherapy has emerged as a promising therapeutic approach to complement existing standards of care. See, e.g., Miller, et al. Cancer Cell, 27, 439-449 (2015). Such immunotherapy approaches include the development of antibodies used to modulate the immune system to kill cancer cells.

Anti-tumor immune responses in patients with solid tumors have been enhanced by treatment with biologics. For example, there are two approved and marketed anti-PD-1 monoclonal antibodies: nivolumab (OPDIVO®) and pembrolizumab (KEYTRUDA®), with approvals in the US and the European Union to treat diseases such as unresectable or metastatic melanoma and metastatic non-small cell lung cancer. Treatment of patients with these agents has resulted in anti-tumor responses as measured by improvement in either progression free survival and/or overall survival.

The recent failure of OPDIVO® to slow progression of advanced lung cancer in a treatment-naïve patient population in a clinical trial comparing OPDIVO® with conventional chemotherapy highlights the need for alternative approaches and additional cancer treatments to complement existing therapeutic standards of care.

5. SUMMARY

The present disclosure provides anti-OX40 antibodies that specifically bind to and activate OX40. The amino acid sequences of exemplary complementarity determining regions (CDRs), the heavy chain variable domain ($V_H$) and light chain variable domain ($V_L$) regions (i.e., the $V_H$ and $V_L$ chains, respectively), and the heavy and light chains of exemplary anti-OX40 antibodies are provided in the Detailed Description below. Anti-OX40 antibodies provided herein result in activation of the adaptive immune response.

The anti-OX40 antibodies may include modifications and/or mutations that alter the properties of the antibodies, such as those that increase half-life, increase or decrease antigen-dependent cellular cytotoxicity (ADCC), as is known in the art.

Nucleic acids comprising nucleotide sequences encoding the anti-OX40 antibodies of the disclosure are provided herein, as are vectors comprising nucleic acids. Additionally, prokaryotic and eukaryotic host cells transformed with a vector comprising a nucleotide sequence encoding a disclosed anti-OX40 antibody are provided herein, as well as eukaryotic (such as mammalian) host cells engineered to express the nucleotide sequences. Methods of producing antibodies, by culturing host cells and recovering the antibodies are also provided, and discussed further in the Detailed Description below.

In another aspect, the present disclosure provides compositions including the anti-OX40 antibodies described herein. The compositions generally comprise one or more anti-OX40 antibodies as described herein, and one or more excipients, carriers or diluents.

The present disclosure provides methods of treating subjects, such as human subjects, i.e., human patients, diagnosed with a solid tumor with an anti-OX40 antibody. The method generally involves administering to the subject an amount of an anti-OX40 antibody described herein effective to provide therapeutic benefit. The subject may be diagnosed with any one of a number of solid tumors that may be newly diagnosed, relapsed, or relapsed and refractory. An anti-OX40 antibody can be administered as an intravenous infusion once every two weeks.

The anti-OX40 antibodies may be administered as single therapeutic agents (monotherapy) or adjunctive to or with other therapeutic agents typically, but not necessarily, those used for the treatment of a solid tumor. Therapeutic agents typically will be used at their approved dose, route of administration, and frequency of administration.

The anti-OX40 antibodies may be administered via a variety of routes or modes of administration, including but not limited to, intravenous infusion and/or injection, and intratumoral injection. The amount administered will depend upon the route of administration, the dosing schedule, the type of cancer being treated, the stage of the cancer being treated, and other parameters such as the age and weight of the patient, as is well known in the art.

6. BRIEF DESCRIPTION OF THE FIGURES

Figure 1B:
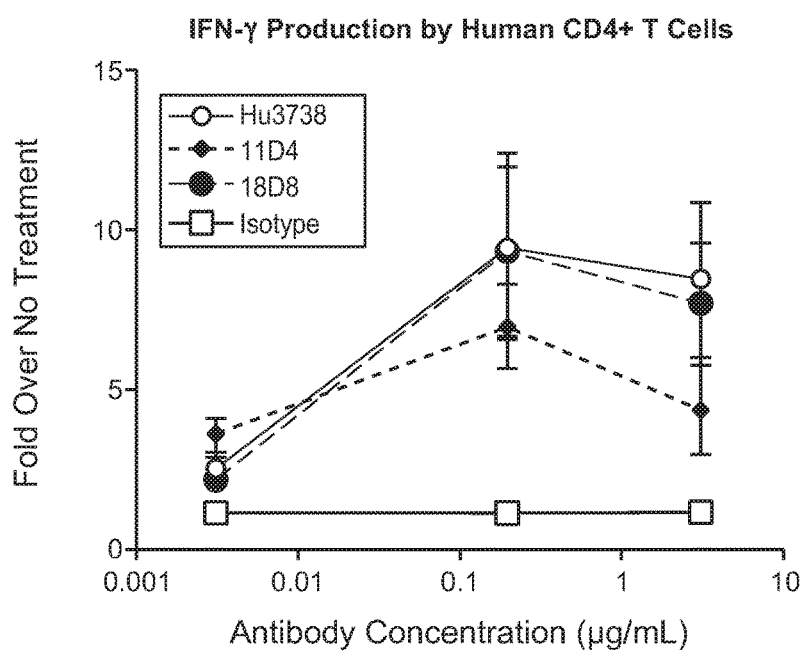
Figure 1C:
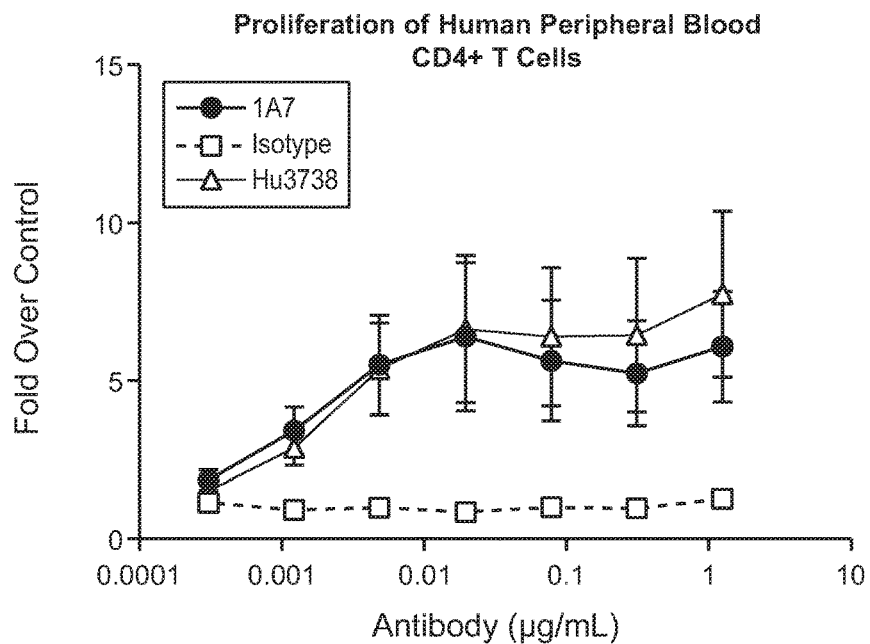
Figure 1D:
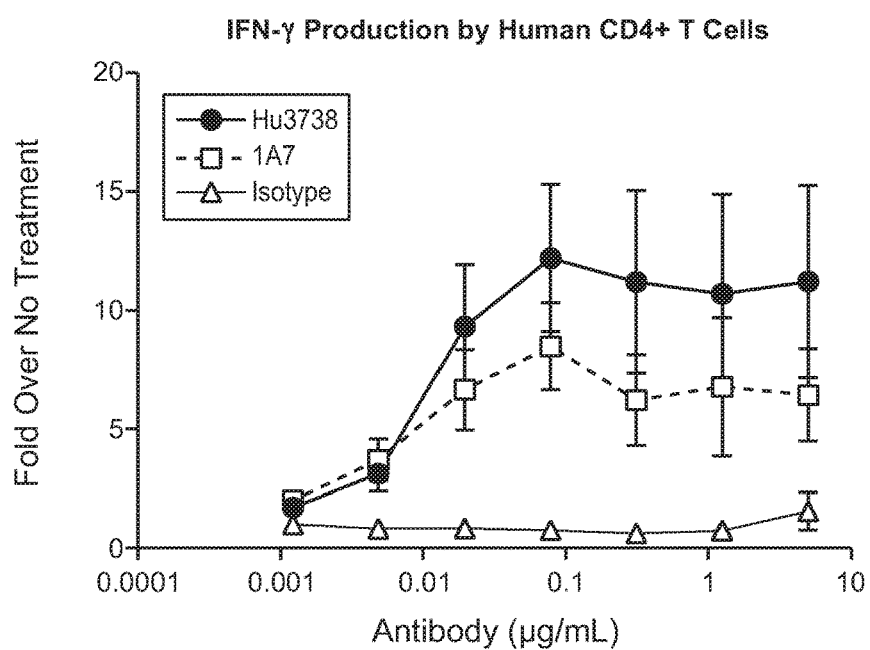

FIGS. 1A-1D depict functional activation of human T cells in vitro after treatment with the exemplary anti-OX40 antibody Hu3738. FIG. 1A depicts the proliferation of human peripheral blood CD4+ T cells after treatment with anti-OX40 antibody Hu3738, or literature antibody 11D4 or 18D8. FIG. 1B depicts the increase in interferon-gamma (IFN-γ) production by human CD4+ T cells after treatment with anti-OX40 antibody Hu3738, or literature antibody 11D4 or 18D8. FIG. 1C depicts the proliferation of human peripheral blood CD4+ T cells after treatment with Hu3738, or literature antibody 1A7. FIG. 1D depicts the increase in IFN-γ production by human CD4+ T cells after treatment with Hu3738, or literature antibody 1A7.

Figure 2A:
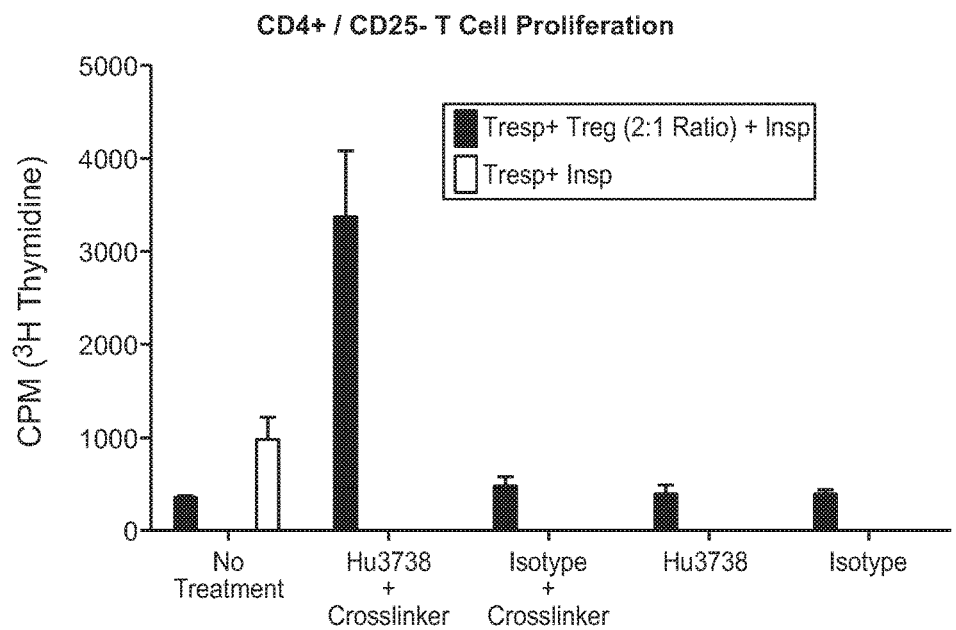
Figure 2B:
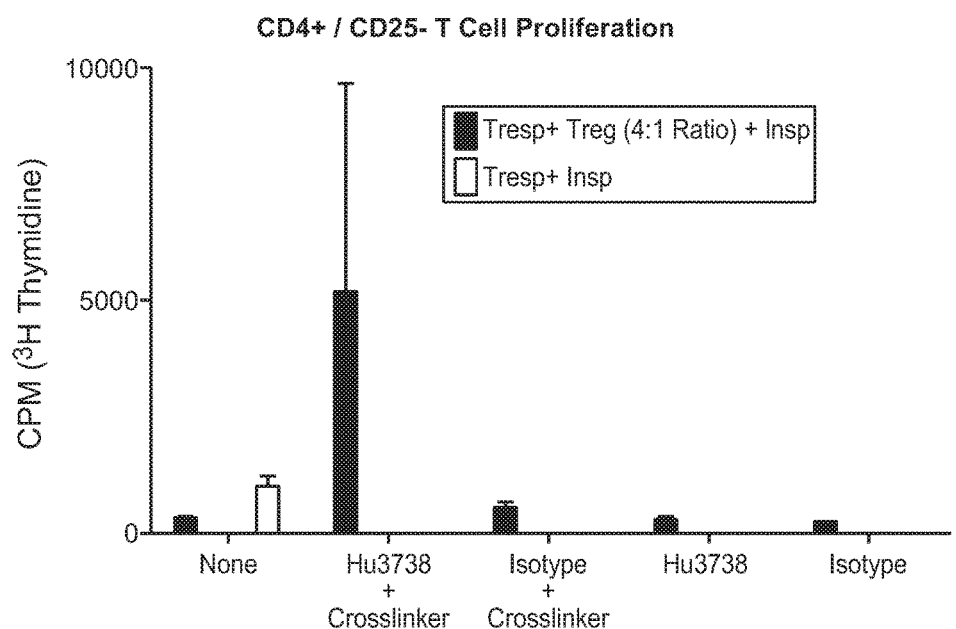

FIGS. 2A-2B show the effect of exemplary anti-OX40 antibody Hu3738 on human T regulatory (Treg) cell-mediated suppression in vitro. The Treg suppression assay was set up using two different ratios of CD4+/CD25− responder T cells (Tresp) to CD4+/CD25+/CD127low T regulatory cells (Treg). Treg Suppression Inspector reagent beads (Insp) were added to culture wells at 1:1 bead-to-cell ratio for stimulation. The clear bar represents proliferation of Tresp cells in the presence of Insp. Anti-OX40 and isotype control human $IgG_1$ antibodies were tested in triplicate at 10 μg/mL final concentration in the absence or presence of cross-linking reagent $(F(ab')_2$ goat anti-human IgG, Fc specific) at 1:4 ratio. Plates were incubated at 37° C. in 5% $CO_2$ for four days. 1μCi/well $^3$H-thymidine was added and the plates were further incubated for another 16 hours. Graphs represent proliferation as shown in counts per minute (cpm). FIG. 2A depicts results with Tresp to Treg at 2:1 ratio; FIG. 2B depicts results with Tresp to Treg at 4:1 ratio.

Figure 3:
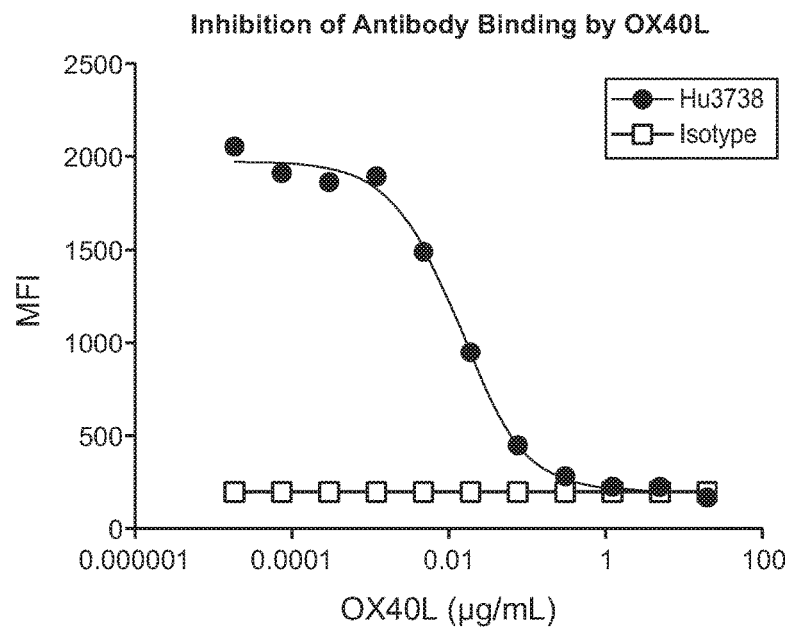

FIG. 3 depicts the inhibition of binding of exemplary anti-OX40 antibody Hu3738 in the presence of soluble human OX40 ligand (OX40L). The graph shows mean fluorescence intensity (MFI) vs. concentration of OX40L (μg/mL). Human OX40-expressing Jurkat cells were co-stained with a titration of unlabeled soluble OX40L and 0.2 μg/mL Hu3738 or isotype control antibody.

Figure 4B:
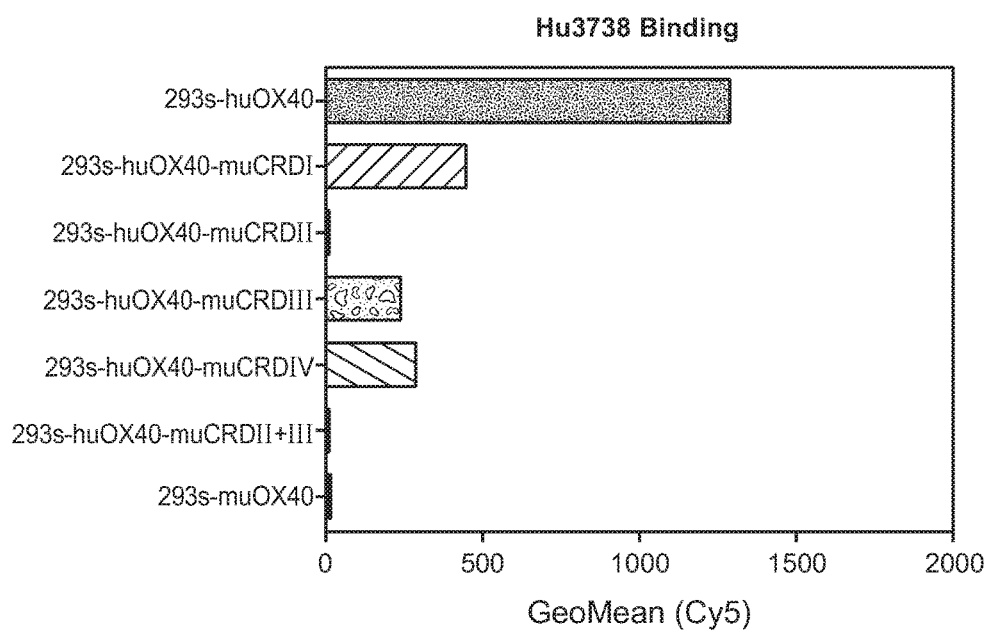

FIG. 4A shows an amino acid sequence alignment of human OX40 (SEQ ID NO:1) with mouse OX40 (SEQ ID NO:3). FIG. 4B depicts the binding activity of exemplary anti-OX40 antibody Hu3738 to cell-surface expressed human, murine, or chimeric human-mouse OX40 molecules containing mouse cysteine-rich domains (CRDs) swapped out for the corresponding human regions. Human OX40 is shown as "293s-huOX40," chimeric human OX40 with murine CRDI is shown as "293s-huOX40-muCRDI," chimeric human OX40 with murine CRDII is shown as "293s-huOX40-muCRDII," chimeric human OX40 with murine CRDIII is shown as "293s-huOX40-muCRDIII," chimeric human OX40 with murine CRDIV is shown as "293s-huOX40-muCRDIV," chimeric human OX40 with murine CRDII and murine CRDIII is shown as "293s-huOX40-muCRDII+III," and murine OX40 is shown as "293s-muOX40."

Figure 5:
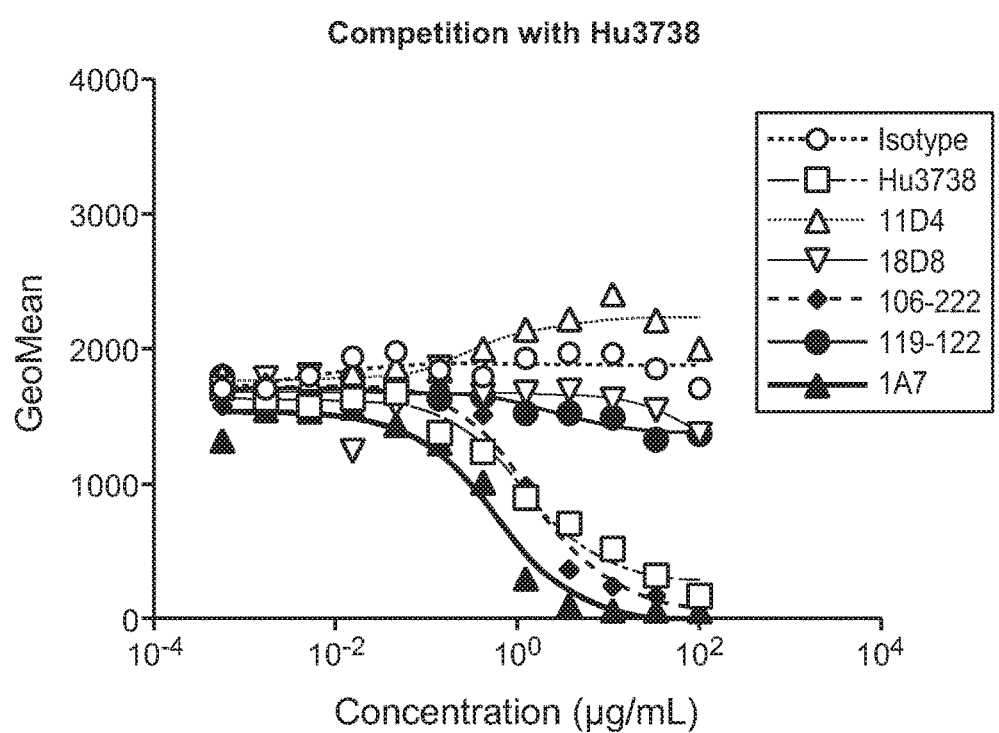

FIG. 5 depicts competition for cell surface human OX40 binding by exemplary anti-OX40 antibody Hu3738 or a literature antibody (11D4, 18D8, 106-222, 119-122, or 1A7).

Figure 6A:
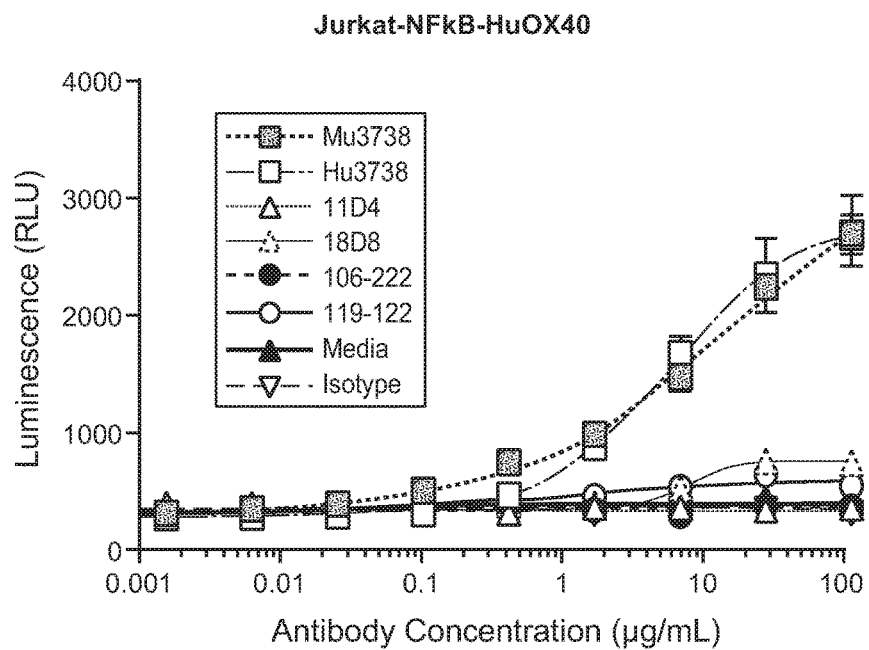
Figure 6B:
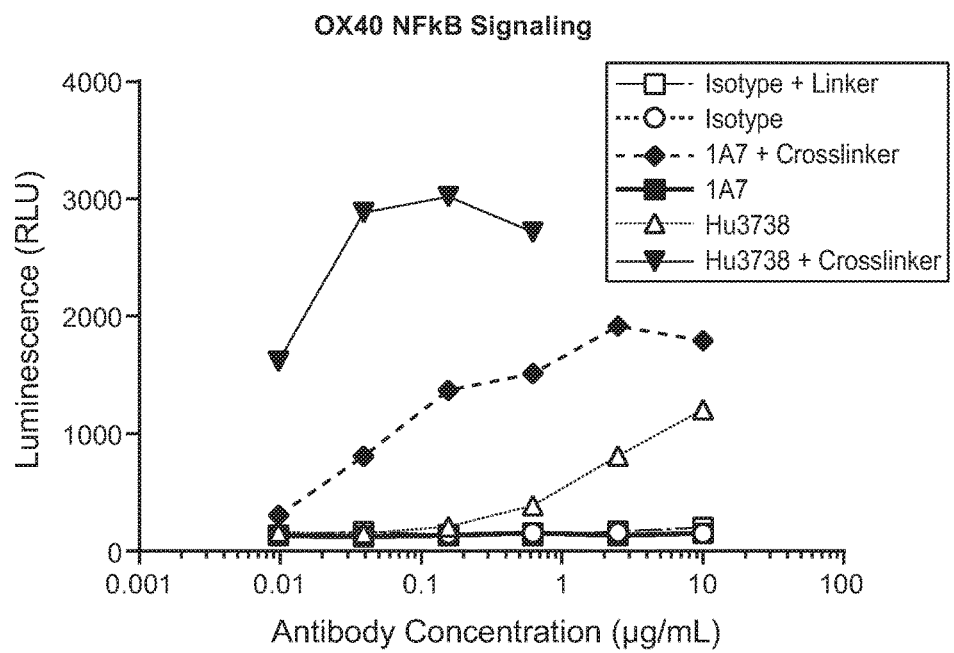

FIG. 6A depicts the activation of NF-κB in human OX40-transfected Jurkat reporter cell lines upon treatment with exemplary anti-OX40 antibody Mu3738 or Hu3738, or literature antibody 11D4, 18D8, 106-222, or 119-122, or isotype control in the absence of an added cross-linker. FIG. 6B depicts the activation of NF-κB in human OX40-transfected Jurkat reporter cell lines upon treatment with exemplary anti-OX40 antibody Hu3738, literature antibody 1A7, or isotype control in the presence or absence of an added cross-linker.

Figure 7:
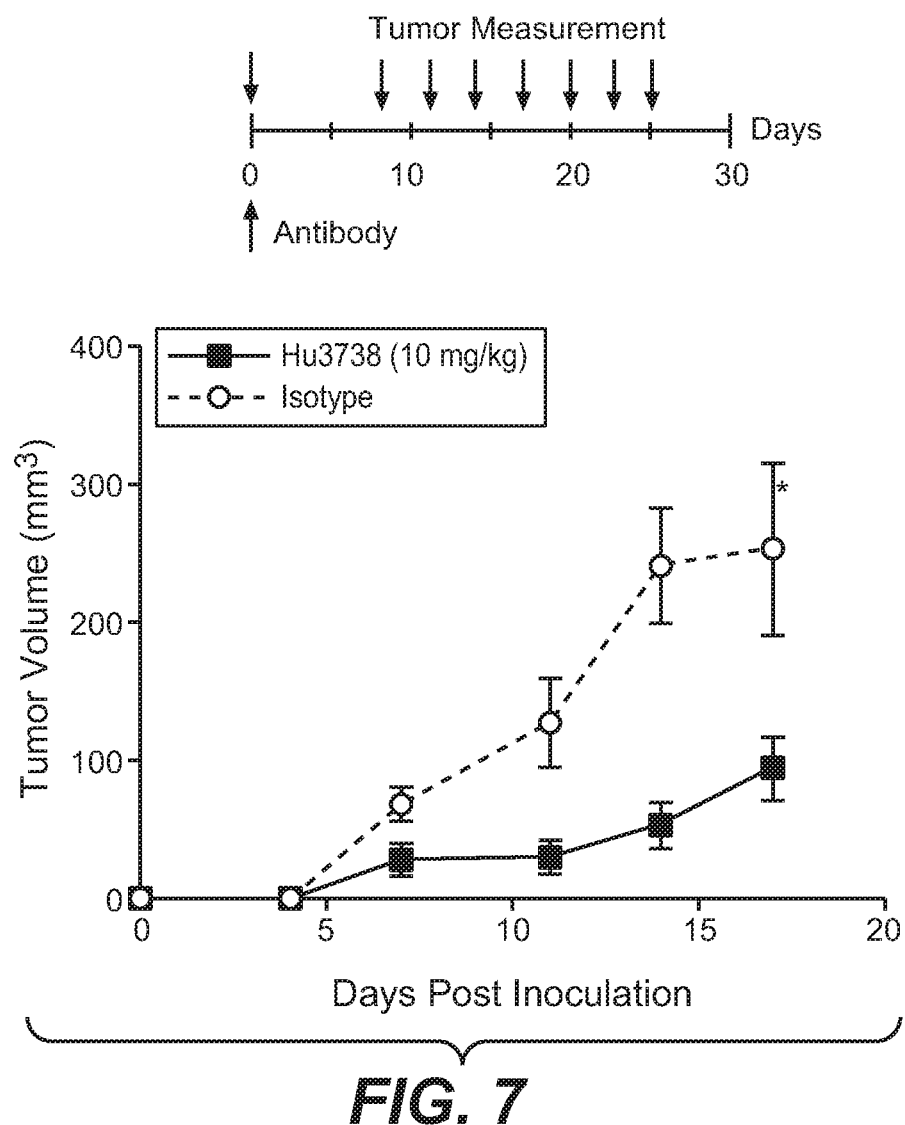

FIG. 7 depicts anti-tumor activity of exemplary anti-OX40 antibody Hu3738 in a human PC3 adoptive cell tumor model in NSG mice.

Figure 8:
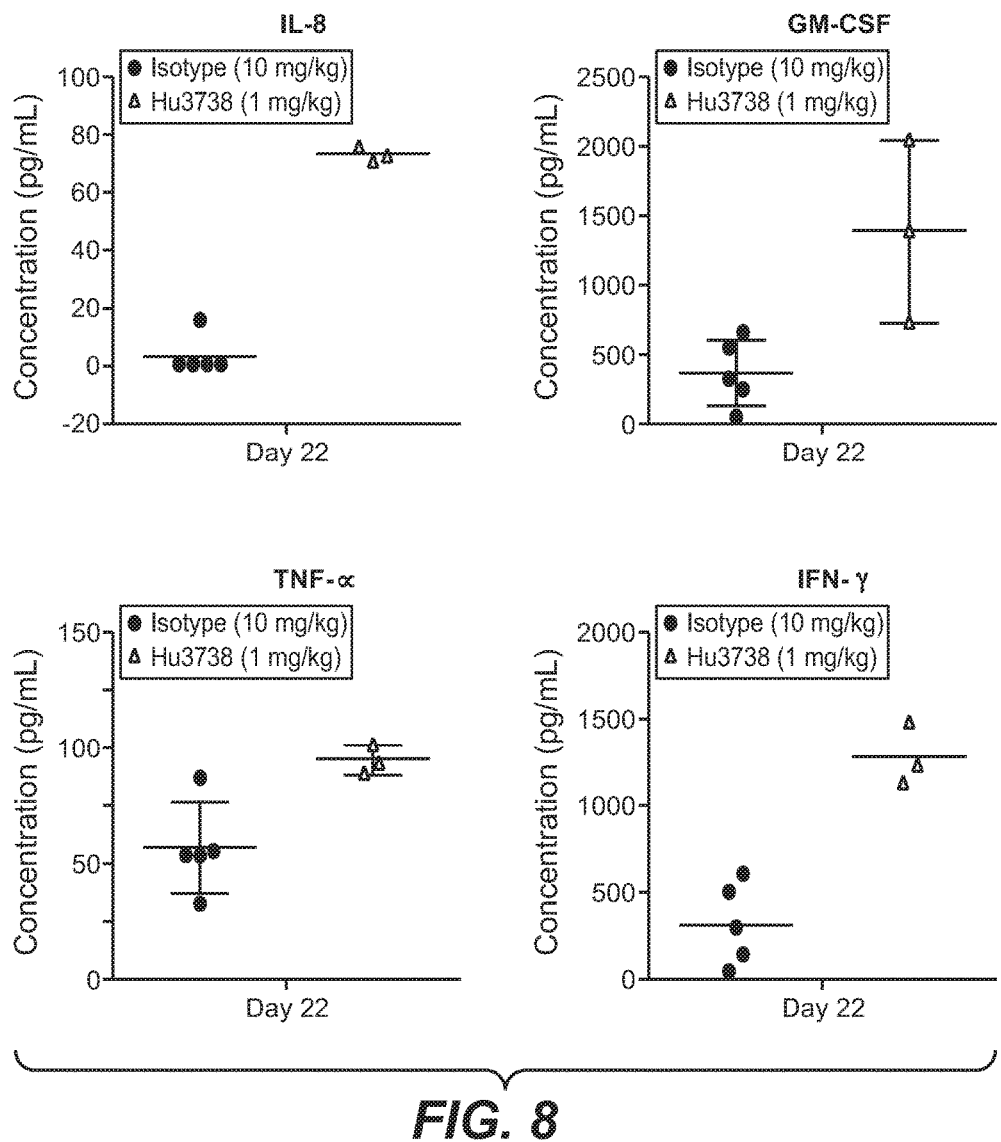

FIG. 8 depicts levels of interleukin-8 (IL-8), granulocyte macrophage colony-stimulating factor (GM-CSF), tumor necrosis factor alpha (TNF-α), and interferon-gamma (IFN-γ) in a human peripheral blood mononuclear cell (PBMC) mediated graft-versus-host disease (GVHD) model in NSG mice, after treating the mice with 1 mg/kg Hu3738 or human $IgG_1$ isotype control once every 7 days for a total of 4 doses.

7. DETAILED DESCRIPTION

The present disclosure concerns antibodies and fragments thereof that specifically bind OX40, compositions comprising the antibodies, polynucleotides encoding anti-OX40 antibodies, host cells capable of producing the antibodies, methods and compositions useful for making the antibodies, and various methods of using the same.

As will be appreciated by skilled artisans, antibodies and fragments thereof are "modular" in nature. Throughout the disclosure, various specific embodiments of the various "modules" composing anti-OX40 antibodies or binding fragments thereof are described. As specific non-limiting examples, various specific embodiments of heavy chain variable domain ($V_H$) complementarity determining regions (CDRs), $V_H$ chains, light chain variable domain ($V_L$) CDRs and $V_L$ chains are described. It is intended that all of the specific embodiments may be combined with each other as though each specific combination were explicitly described individually.

7.1. Abbreviations

The antibodies, binding fragments, and polynucleotides described herein are, in many embodiments, described by way of their respective polypeptide or polynucleotide sequences. Unless indicated otherwise, polypeptide sequences are provided in N→C orientation; polynucleotide sequences in 5'→3' orientation. For polypeptide sequences, the conventional three or one-letter abbreviations for the genetically encoded amino acids may be used, as noted in TABLE 1, below.

TABLE 1

Encoded Amino Acid Abbreviations

| Amino Acid | Three Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Certain sequences are defined by structural formulae specifying amino acid residues belonging to certain classes (e.g., aliphatic, hydrophobic, etc.). The various classes to which the genetically encoded amino acids belong as used herein are noted in TABLE 2, below. Some amino acids may belong to more than one class. Cysteine, which contains a sulfhydryl group, and proline, which is conformationally constrained, are not assigned classes.

TABLE 2

Encoded Amino Acid Classes

| Class | Amino Acids |
| --- | --- |
| Aliphatic | A, I, L, V |
| Aromatic | F, Y, W |
| Non-Polar | M, A, I, L, V |
| Polar | N, Q, S, T |
| Basic | H, K, R |
| Acidic | D, E |
| Small | A, G |

7.2. Definitions

Unless otherwise defined herein, scientific and technical terms used in connection with the present disclosure shall have the meanings that are commonly understood by those of ordinary skill in the art.

7.3. Anti-OX40 Antibodies and Binding Fragments

OX40 is a co-stimulatory molecule that has a critical role in the enhancement of nascent immune responses and concomitantly acts to suppress regulatory T cell activity. OX40, also known as CD134 or tumor necrosis factor receptor superfamily 4 (TNFRSF4), is a Type I transmembrane cell surface member of the tumor necrosis factor (TNF) receptor superfamily transiently expressed on recently activated T cells and constitutively expressed on activated T regulatory cells. The extracellular ligand binding domain of OX40 is composed of three cysteine-rich domains (CRD) and a fourth partial CRD (CRDI, CRDII, CRDIII, and CRDIV, respectively). While primarily expressed by activated CD4+ T cells, OX40 can be expressed on B cells, CD8+ T cells, and natural killer (NK) and natural killer T (NKT) cells following activation. Neutrophils have also been reported to express OX40 and signaling through OX40 on human neutrophils inhibits apoptotic cell death. The ligand for OX40 (OX40L), also known as tumor necrosis factor ligand superfamily 4 (TNFSF4), CD252 or glycoprotein 34 (gp34), is upregulated by activated antigen-presenting cells and B cells. Ligand binding to OX40 on antigen-activated T cells results in downstream NF-κB translocation and AKT pathway activation. NF-κB translocation leads to upregulation of pro-survival molecules such as Bcl-2, Bcl-XL and cell survival. Activating antibodies directed at OX40 are intended at least in part to enhance antigen-specific immune responses by prolonging activation and differentiation of T effector cells.

In addition to the impact on antigen activated T effector cells, targeting OX40 expressed by T regulatory cells may also contribute to the putative mechanism of action. T regulatory cells express high levels of OX40 within the tumor microenvironment. OX40 activation has been shown to impact suppressive capacity of T regulatory cells and to lead to the active depletion of OX40 positive T regulatory cells from the tumor microenvironment.

In one aspect, the disclosure concerns antibodies that specifically bind OX40.

As used herein, the term "antibody" (Ab) refers to an immunoglobulin molecule that specifically binds to a particular antigen—here, OX40. In some embodiments, the anti-OX40 antibodies of the disclosure bind to human OX40 (SEQ ID NO:1) (NCBI Reference Sequence NP003318) and thereby modulate the immune system. The resulting immune system response is cytotoxic to tumor cells. Anti-OX40 antibodies comprise complementarity determining regions (CDRs), also known as hypervariable regions, in both the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies. See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al. unless otherwise indicated.

The antibodies of the disclosure may be polyclonal, monoclonal, genetically engineered, and/or otherwise modified in nature, including but not limited to chimeric antibodies, humanized antibodies, and human antibodies. In some embodiments, the constant region is an isotype selected from: IgA (e.g., $IgA_1$ or $IgA_2$), IgD, IgE, IgG (e.g., $IgG_1$, $IgG_2$, $IgG_3$ or $IgG_4$), and IgM. In specific embodiments, an anti-OX40 antibody described herein comprises an $IgG_1$. In other embodiments, the anti-OX40 antibodies comprise an $IgG_2$ or $IgG_4$. As used herein, the "constant region" of an antibody includes the natural constant region, allotypes or natural variants, such as D356E and L358M, or A431G in human $IgG_1$. See, e.g., Jefferis and Lefranc, MAbs, 1(4): 332-338 (July-August 2009).

The light constant region of an anti-OX40 antibody may be a kappa (κ) light region or a lambda (λ) region. A λ light region can be any one of the known subtypes, e.g., $\lambda_1$, $\lambda_2$, $\lambda_3$, or $\lambda_4$. In some embodiments, the anti-OX40 antibody comprises a kappa (κ) light region.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of the anti-OX40 antibodies in humans, chimeric, humanized, or human antibodies can be used.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

"Human antibodies" include antibodies having the amino acid sequence of a human immunoglobulin and include antibodies isolated from human immunoglobulin libraries or from animals transgenic for one or more human immunoglobulins and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as LakePharma, Inc. (Belmont, Calif.) or Creative BioLabs (Shirley, N.Y.) can be engaged to provide human antibodies directed against a selected antigen using technology similar to that described above. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

Also contemplated are anti-OX40 antibody binding fragments. The binding fragments of the disclosure include those that are capable of specifically binding OX40. Examples of antibody binding fragments include by way of example and not limitation, Fab, Fab', F(ab')$_2$, Fv fragments, single chain Fv (scFv) fragments and single domain fragments.

A Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab' fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_2$ fragments lack the Fragment crystallizable (Fc) region of an intact antibody, clear more rapidly from the circulation of animals, and may have less non-specific tissue binding than an intact antibody (see, e.g., Wahl et al., 1983, J. Nucl. Med. 24:316).

As is commonly understood in the art, an "Fc" region is the Fragment crystallizable constant region of an antibody not comprising an antigen-specific binding region. In IgG, IgA and IgD antibody isotypes, the Fc region is composed of two identical protein fragments, derived from the second and third constant domains (CH2 and CH3 domains, respectively) of the two heavy chains of an antibody. IgM and IgE Fc regions contain three heavy chain constant domains (CH2, CH3, and CH4 domains) in each polypeptide chain.

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site.

"Single-chain Fv" or "scFv" antibody binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form a structure favorable for target binding.

"Single domain fragments" are composed of a single $V_H$ or $V_L$ domains which exhibit sufficient affinity to OX40. In a specific embodiment, the single domain fragment is camelized (See, e.g., Riechmann, 1999, Journal of Immunological Methods 231:25-38).

Anti-OX40 antibodies of the disclosure include derivatized antibodies. For example, derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (See, e.g., Wolfson, 2006, Chem. Biol. 13(10):1011-2).

The anti-OX40 antibodies may be antibodies whose sequences have been modified to alter at least one constant region-mediated biological effector function. For example, in some embodiments, an anti-OX40 antibody may be modified to reduce at least one constant region-mediated biological effector function relative to the unmodified antibody, e.g., reduced binding to one or more of the Fc receptors (FcγR) such as FcγRI, FcγRIIA, FcγRIIB, FcγRIIIA and/or FcγRIIIB. FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC"). In an illustrative example, a variant CH2 domain having a V263L, V273C, V273E, V273F, V273L, V273M, V273S, or V273Y substitution in the CH2 domain of the Fc region can exhibit reduced affinity to FcγRIIB as compared to the corresponding wild type constant region.

The anti-OX40 antibody described herein include antibodies that have been modified to acquire or improve at least one constant region-mediated biological effector function relative to an unmodified antibody, e.g., to enhance FcγR interactions (See, e.g., US Patent Appl. No. 2006/0134709). For example, an anti-OX40 antibody of the disclosure can have a constant region that binds FcγRI, FcγRIIA, FcγRIIB, FcγRIIIA and/or FcγRIIIB with greater affinity than the corresponding wild type constant region. In an illustrative example, a variant CH2 domain having a V263L, V273C, V273E, V273F, V273L, V273M, V273S, or V273Y substitution in the CH2 domain of the Fc region can exhibit greater affinity to FcγRIIIA as compared to the corresponding wild type constant region.

Thus, anti-OX40 antibodies of the disclosure may have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (also known as "M3," shown in FIG. 4 of U.S. Pat. No. 5,834,597) in which residues 234 and 237 (using EU numbering) are substituted with alanines. A mutant 3 (also known as "M3") variation may be used in a number of antibody isotypes, e.g., human $IgG_2$ M3.

Additional substitutions that can modify FcγR binding and/or ADCC effector function of an anti-OX40 antibody include the K322A substitution or the L234A and L235A double substitution in the Fc region, for example, a human $IgG_1$ having the L234A/L235A double substitution. See, e.g., Hezareh, et al. J. Virol., 75 (24): 12161-12168 (2001).

In some embodiments, the anti-OX40 antibodies have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

Anti-OX40 antibodies can comprise modified (or variant) CH2 domains or entire Fc domains that include amino acid substitutions that increase binding to FcγRIIB and/or reduced binding to FcγRIIIA as compared to the binding of a corresponding wild-type CH2 or Fc region. Variant CH2 or variant Fc domains have been described in U.S. Patent Appl. No. 2014/0377253. A variant CH2 or variant Fc domain typically includes one or more substitutions at position 263, position 266, position 273, and position 305, wherein the numbering of the residues in the Fc domain is that of the EU index as in Kabat. In some embodiments, the anti-OX40 antibodies comprise one or more substitutions selected from V263L, V266L, V273C, V273E, V273F, V273L, V273M, V273S, V273Y, V305K, and V305W, relative to the wild-type CH2 domain. In specific embodiments, the one or more substitutions of the CH2 domain are selected from V263L, V273E, V273F, V273M, V273S, and V273Y, relative to the CH2 domain of a human $IgG_1$. For example, the one or more substitutions of an $IgG_1$ CH2 domain can be V273E. In another specific embodiment, the anti-OX40 antibody of the disclosure comprises a variant $IgG_1$ CH2 domain comprising the amino acid substitution V263L.

Other examples of variant CH2 or variant Fc domains that can afford increased binding to FcγRIIB and/or reduced binding to FcγRIIIA as compared to the binding of a corresponding wild-type CH2 or Fc region include those found in Vonderheide, et al. Clin. Cancer Res., 19(5), 1035-1043 (2013), such as S267E or S267E/L328F in human $IgG_1$.

In some embodiments, the anti-OX40 antibodies include modifications that increase or decrease their binding affinities to the fetal Fc receptor, FcRn, for example, by mutating the immunoglobulin constant region segment at particular regions involved in FcRn interactions (see, e.g., WO 2005/123780). In particular embodiments, an anti-OX40 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. An exemplary substitution known to modify Fc effector function is the Fc substitution M428L, which can occur in combination with the Fc substitution T250Q. Additional specific combinations of suitable amino acid substitutions are identified in Table 1 of U.S. Pat. No. 7,217,797. Such mutations increase binding to FcRn, which protects the antibody from degradation and increases its half-life.

An anti-OX40 antibody may have one or more amino acids inserted into one or more of its CDRs, for example as described in Jung and Plückthun, 1997, Protein Engineering 10:8, 959-966; Yazaki et al., 2004, Protein Eng. Des Sel. 17(5):481-9. Epub 2004 Aug. 17; and U.S. Pat. Appl. No. 2007/0280931.

Anti-OX40 antibodies with high affinity for human OX40 (SEQ ID NO:1) may be desirable for therapeutic and diagnostic uses. Accordingly, the present disclosure contemplates antibodies having a high binding affinity to human OX40. In specific embodiments, the anti-OX40 antibodies bind human OX40 with an affinity of at least about 100 nM, but may exhibit higher affinity, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind human OX40 with an affinity in the range of about 1 pM to about 100 nM, or an affinity ranging between any of the foregoing values, such as but not limited to from about 0.001 to 10 nM, 0.001 to 5 nM, 0.01 to 100 nM, 0.01 to 50 nM, 0.01 to 10 nM, 0.01 to 5 nM, or 0.01 to 1 nM.

Affinity of anti-OX40 antibodies for human OX40 can be determined using techniques well known in the art or described herein, such as for example, but not by way of limitation, ELISA, isothermal titration calorimetry (ITC), surface plasmon resonance, or fluorescent polarization assay.

Anti-OX40 antibodies generally comprise a heavy chain comprising a variable region ($V_H$) having three complementarity determining regions ("CDRs") referred to herein (in N→C order) as $V_H$ CDR#1, $V_H$ CDR#2, and $V_H$ CDR#3, and a light chain comprising a variable region ($V_L$) having three complementarity determining regions referred to herein (in N→C order) as $V_L$ CDR#1, $V_L$ CDR#2, and $V_L$ CDR#3. The amino acid sequences of exemplary CDRs, as well as the amino acid sequence of the $V_H$ and $V_L$ regions of the heavy and light chains of exemplary anti-OX40 are provided herein. Specific embodiments of anti-OX40 antibodies include these exemplary CDRs and/or $V_H$ and/or $V_L$ sequences, as well as antibodies that compete for binding human OX40 with such antibodies.

In some embodiments, the amino acid sequences of the CDRs of an anti-OX40 antibody have sequences selected from their respective $V_H$ and $V_L$ CDR sequences in TABLE 3 below:

TABLE 3

Exemplary CDR Sequences

| CDR | Sequence | Identifier |
|---|---|---|
| $V_H$ CDR#1: | GFTFSRYGMS | (SEQ ID NO: 101) |
|  | GYSIASGYYWN | (SEQ ID NO: 111) |
|  | GFNIKDTYMH | (SEQ ID NO: 121) |
|  | GFSLTSYGVH | (SEQ ID NO: 131) |
| $V_H$ CDR#2: | TINSNGGRTYYPDSVKG | (SEQ ID NO: 102) |
|  | YISYDGSNNYNPSLG | (SEQ ID NO: 112) |
|  | RIDPANGNTKYDPKFQG | (SEQ ID NO: 122) |
|  | VIWSGGSTDYNAAFIS | (SEQ ID NO: 132) |

TABLE 3-continued

Exemplary CDR Sequences

| CDR | Sequence | Identifier |
|---|---|---|
| $V_H$ CDR#3: | EGITTAYAMDY | (SEQ ID NO: 103) |
|  | TLPYYFDY | (SEQ ID NO: 113) |
|  | GGPAWFVY | (SEQ ID NO: 123) |
|  | EEFDY | (SEQ ID NO: 133) |
| $V_L$ CDR#1: | KASQSVDYDGDSYMH | (SEQ ID NO: 104) |
|  | RASQDISNYLN | (SEQ ID NO: 114) |
| $V_L$ CDR#2: | AASILES | (SEQ ID NO: 105) |
|  | YTSRLHS | (SEQ ID NO: 115) |
|  | YTSRLRS | (SEQ ID NO: 125) |
| $V_L$ CDR#3: | QQSNEDPRT | (SEQ ID NO: 106) |
|  | QQGNTLPLT | (SEQ ID NO: 116) |
|  | QQGNTLPWT | (SEQ ID NO: 126) |
|  | QQGYTLPPT | (SEQ ID NO: 136) |

Specific exemplary embodiments of anti-OX40 antibodies with the above CDRs are described herein. In some embodiments, an anti-OX40 antibody has the CDRs according to SEQ ID NOS: 101, 102, 103, 104, 105, and 106. In some embodiments, an anti-OX40 antibody has the CDRs according to SEQ ID NOS: 111, 112, 113, 114, 115, and 116. In some embodiments, an anti-OX40 antibody has the CDRs according to SEQ ID NOS: 121, 122, 123, 114, 125, and 126. In some embodiments, an anti-OX40 antibody has the CDRs according to SEQ ID NOS: 131, 132, 133, 114, 115, and 136.

The CDRs described herein form binding elements within $V_H$ and $V_L$ chains of anti-OX40 antibodies of the disclosure. TABLES 4 and 5 below describe $V_H$ and $V_L$ chains corresponding to exemplary anti-OX40 antibodies containing the above-described CDRs. The CDRs are underlined below in TABLES 4 and 5. In some embodiments, an anti-OX40 antibody comprises a $V_H$ chain having an amino acid sequence as described in TABLE 4:

TABLE 4

Exemplary $V_H$ Sequences

| $V_H$ | Sequence | Identifier |
|---|---|---|
| Mu3738 $V_H$ | EVQLVESGGGLVQPGGSLKLSCAAS<u>GFTFSRYGMS</u>WVRQT PDKRLELVA<u>TINSNGGRTYYPDSVKG</u>RFTISRDNAKNTLYL QMSSLKSEDTAMYYCAR<u>EGITTAYAMDY</u>WGQGTSVTVSS | (SEQ ID NO: 21) |
| Hu3738 $V_H$.1b | EVQLVESGGGLVQPGGSLRLSCAAS<u>GFTFSRYGMS</u>WVRQA PGKGLELVA<u>TINSNGGRTYYPDSVKG</u>RFTISRDNAKNSLYL QMNSLRAEDTAVYYCAR<u>EGITTAYAMDY</u>WGQGTTVTVSS | (SEQ ID NO: 22) |
| Mu3726 $V_H$ | NVQLQESGPGLVKPSQSLSLTCSVT<u>GYSIASGYYWN</u>WIRQF PGNKLEWMG<u>YISYDGSNNYNPSLG</u>NRISITRDTSKNQVFLK LNSVTTEDTATYYCVK<u>TLPYYFDY</u>WGQGTTLTVSS | (SEQ ID NO: 23) |
| Hu3726 $V_H$.1a | EVQLQESGPGLVKPSDTLSLTCAVS<u>GYSIASGYYWN</u>WIRQP PGKGLEWMG<u>YISYDGSNNYNPSLG</u>NRITISRDTSKNQVSLK LSSVTAVDTAVYYCVK<u>TLPYYFDY</u>WGQGTTVTVSS | (SEQ ID NO: 24) |
| Mu3739 $V_H$ | EVQLQQSGAELVKPGASVKLSCTASG<u>FNIKDTYMH</u>WVKQR PEQGLEWIG<u>RIDPANGNTKYDPKFQG</u>KATITADTSSNTAYL QLSSLTSEDTDVYYCAR<u>GGPAWFVY</u>WGQGTLVTVSA | (SEQ ID NO: 25) |
| Hu3739 $V_H$.1b | EVQLVQSGAEVKKPGSSVKVSCKAS<u>GFNIKDTYMH</u>WVRQ APGQGLEWIG<u>RIDPANGNTKYDPKFQG</u>RATITADTSTNTAY MELSSLRSEDTAVYYCAR<u>GGPAWFVY</u>WGQGTLVTVSS | (SEQ ID NO: 26) |
| Mu3741 $V_H$ | QVQLKQSGPGLVQPSQSLSITCTVS<u>GFSLTSYGVH</u>WVRQSP GKGLEWLG<u>VIWSGGSTDYNAAFIS</u>RLSISKDNSKSQVFFKM NSLQADDTAIYCCAR<u>EEFDY</u>WGQGTTLTVSS | (SEQ ID NO: 27) |

TABLE 4-continued

Exemplary V_H Sequences

| V_H | Sequence | Identifier |
|---|---|---|
| Hu3741 V_H.2b | EVQLVESGGGLVQPGGSLRLSCAVS<u>GFSLTSYGVH</u>WVRQA PGKGLEWLGV<u>IWSGGSTDYNAAFI</u>SRLTISKDNSKSTVYLQ MNSLRAEDTAVYYCAR<u>EEFDY</u>WGQGTTVTVSS | (SEQ ID NO: 28) | and a $V_L$ chain having an amino acid sequence as described in TABLE 5:

TABLE 5

Exemplary V_L Sequences

| V_L | Sequence | Identifier |
|---|---|---|
| Mu3738 V_L | DIVLTQSPASLAVSLGQRATISC<u>KASQSVDYDGDSYMH</u>W YQQKPGQPPKLLIY<u>AASILES</u>GIPARFSGSGSGTDFTLNIHP VEEEDAATYYC<u>QQSNEDPRT</u>FGGGTKLEIK | (SEQ ID NO: 31) |
| Hu3738 V_L.1 | DIVMTQSPDSLAVSLGERATINC<u>KASQSVDYDGDSYMH</u>W YQQKPGQPPKLLIY<u>AASILES</u>GVPDRFSGSGSGTDFTLTISS LQAEDVAVYYC<u>QQSNEDPRT</u>FGGGTKVEIK | (SEQ ID NO: 32) |
| Mu3726 V_L | DIQMTQTTSSLSASLGDRVTISC<u>RASQDISNYLN</u>WYQQKP DGTVKLLIF<u>YTSRLHS</u>GVPSRFSGGGSGTDYSLTISNLEQE DIATYFC<u>QQGNTLPLT</u>FGAGTKLELK | (SEQ ID NO: 33) |
| Hu3726 V_L.1b | DIQMTQTPSSLSASVGDRVTITC<u>RASQDISNYLN</u>WYQQKP GKAPKLLIF<u>YTSRLHS</u>GVPSRFSGSGSGTDYTLTISSLQPED FATYYC<u>QQGNTLPLT</u>FGQGTKLEIK | (SEQ ID NO: 34) |
| Mu3739 V_L | DIQMTQTTSSLSASLGDRVTISC<u>RASQDISNYLN</u>WYQQKP DGTVKLLIY<u>YTSRLRS</u>GLPSRFSGSGSGTDYSLTISNLEQE DIATYFC<u>QQGNTLPWT</u>FGGGTKLEIK | (SEQ ID NO: 35) |
| Hu3739 V_L.1b | DIQMTQSPSSLSASVGDRVTITC<u>RASQDISNYLN</u>WYQQKP GKAPKLLIY<u>YTSRLRS</u>GLPSRFSGSGSGTDYTLTISSLQPED FATYYC<u>QQGNTLPWT</u>FGGGTKVEIK | (SEQ ID NO: 36) |
| Mu3741 V_L | DIQMTQTTSSLSASLGDRVTISC<u>RASQDISNYLN</u>WFQQKP DGTVKLLIY<u>YTSRLHS</u>GVPSRFSGSGSGTDYSLTISNLEQE DIATYFC<u>QQGYTLPPT</u>FGGGTKLEIK | (SEQ ID NO: 37) |
| Hu3741 V_L.1c | DIQMTQSPSSLSASVGDRVTITC<u>RASQDISNYLN</u>WFQQKP GKAPKLLIY<u>YTSRLHS</u>GVPSRFSGSGSGTDYTLTISSLQPE DFATYYC<u>QQGYTLPPT</u>FGGGTKVEIK | (SEQ ID NO: 38) |

In some embodiments, an anti-OX40 antibody comprises a $V_H$ chain having an amino acid sequence according to SEQ ID NO:21, and a $V_L$ chain having an amino acid sequence according to SEQ ID NO:31. In some embodiments, an anti-OX40 antibody comprises a $V_H$ chain having an amino acid sequence according to SEQ ID NO:23, and a $V_L$ chain having an amino acid sequence according to SEQ ID NO:33. In some embodiments, an anti-OX40 antibody comprises a $V_H$ chain having an amino acid sequence according to SEQ ID NO:25, and a $V_L$ chain having an amino acid sequence according to SEQ ID NO:35. In some embodiments, an anti-OX40 antibody comprises a $V_H$ chain having an amino acid sequence according to SEQ ID NO:27, and a $V_L$ chain having an amino acid sequence according to SEQ ID NO:37.

In some embodiments, an anti-OX40 antibody is suitable for administration to humans. In a specific embodiment, the anti-OX40 antibody is humanized. In some embodiments, an anti-OX40 antibody comprises a $V_H$ chain having an amino acid sequence according to SEQ ID NO:22, and a $V_L$ chain having an amino acid sequence according to SEQ ID NO:32. In some embodiments, an anti-OX40 antibody comprises a $V_H$ chain having an amino acid sequence according to SEQ ID NO:24, and a $V_L$ chain having an amino acid sequence according to SEQ ID NO:34. In some embodiments, an anti-OX40 antibody comprises a $V_H$ chain having an amino acid sequence according to SEQ ID NO:26, and a $V_L$ chain having an amino acid sequence according to SEQ ID NO:36. In some embodiments, an anti-OX40 antibody comprises a $V_H$ chain having an amino acid sequence according to SEQ ID NO:28, and a $V_L$ chain having an amino acid sequence according to SEQ ID NO:38.

Certain mutations of a $V_H$ or $V_L$ sequence in an anti-OX40 antibody described herein would be understood by a person of skill to afford anti-OX40 antibodies within the scope of the disclosure. Mutations may include amino acid substitutions, additions, or deletions from a $V_H$ or $V_L$ sequence as disclosed herein while retaining significant anti-OX40 activity. Accordingly, in some embodiments, an anti-OX40 antibody comprises a $V_H$ sequence having at least 85%, at least 90%, at least 93%, at least 95%, at least 96%, at least 97%, at least 98%, or at least 99% sequence identity to any one of the $V_H$ sequences shown in TABLE 4. An anti-OX40 antibody can comprise a $V_H$ sequence having up to 8, up to 7, up to 6, up to 5, up to 4, up to 3, or up to 2 mutations compared with any one of the $V_H$ sequences shown in TABLE 4. In some embodiments, an anti-OX40 antibody can comprise a $V_H$ sequence having 5 or fewer, 4 or fewer, 3 or fewer, or 2 or fewer mutations compared with any one of the $V_H$ sequences shown in TABLE 4. In some embodiments, an anti-OX40 antibody comprises a $V_L$ sequence having at least 85%, at least 90%, at least 93%, at least 95%, at least 96%, at least 97%, at least 98%, or at least 99% sequence identity to any one of the $V_L$ sequences shown in TABLE 5. An anti-OX40 antibody can comprise a $V_L$ sequence having up to 8, up to 7, up to 6, up to 5, up to 4, up to 3, or up to 2 mutations compared with any one of the $V_L$ sequences shown in TABLE 5. In some embodiments, an anti-OX40 antibody can comprise a $V_L$ sequence having 5 or fewer, 4 or fewer, 3 or fewer, or 2 or fewer mutations compared with any one of the $V_L$ sequences shown in TABLE 5.

Full length heavy and light chain amino acid sequences generally comprise an above-described $V_H$ or $V_L$ chain linked to an appropriate immunoglobulin constant region, e.g., human $IgG_1$ or kappa light constant region. Post-translational modifications to the full length sequences of an anti-OX40 antibody may occur, such as cleavage of one or more (e.g., 1, 2, 3, or more) amino acid residues on the C-terminal end of the antibody heavy chain. Such cleavage products may comprise some or all of the anti-OX40 antibody as expressed.

Accordingly, in some embodiments, an anti-OX40 antibody comprises a heavy chain amino acid sequence as described in TABLE 6:

TABLE 6

Exemplary Heavy Chain Sequences

| Sequence | Identifier |
|---|---|
| EVQLVESGGGLVQPGGSLRLSCAAS<u>GFTFSRYGMS</u>WVRQAPGKGLELVA<u>TIN SNGGRTYYPDSVKG</u>RFTISRDNAKNSLYLQMNSLRAEDTAVYYCAR<u>EGITTA YAMDY</u>WGQGTTVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKCK VSNKALPAPIEKTISKAKGQPREPQVYTLPPSREEMTKNQVSLTCLVKGFYPSDIAV EWESNGQPENNYKTTPPVLDSDGSFFLYSKLTVDKSRWQQGNVFSCSVMHEALH NHYTQKSLSLSPGK | SEQ ID NO: 41 |
| EVQLVESGGGLVQPGGSLRLSCAAS<u>GFTFSRYGMS</u>WVRQAPGKGLELVA<u>TIN SNGGRTYYPDSVKG</u>RFTISRDNAKNSLYLQMNSLRAEDTAVYYCAR<u>EGITTA YAMDY</u>WGQGTTVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKCK VSNKALPAPIEKTISKAKGQPREPQVYTLPPSREEMTKNQVSLTCLVKGFYPSDIAV EWESNGQPENNYKTTPPVLDSDGSFFLYSKLTVDKSRWQQGNVFSCSVMHEALH NHYTQKSLSLSPG | SEQ ID NO: 42 |
| EVQLQESGPGLVKPSDTLSLTCAVS<u>GYSIASGYYWN</u>WIRQPPGKGLEWMG<u>YI SYDGSNNYNPSLGN</u>RITISRDTSKNQVSLKLSSVTAVDTAVYYCVK<u>TLPYYFD Y</u>WGQGTTVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHNHYTQ KSLSLSPGK | SEQ ID NO: 43 |
| EVQLQESGPGLVKPSDTLSLTCAVS<u>GYSIASGYYWN</u>WIRQPPGKGLEWMG<u>YI SYDGSNNYNPSLGN</u>RITISRDTSKNQVSLKLSSVTAVDTAVYYCVK<u>TLPYYFD Y</u>WGQGTTVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHNHYTQ KSLSLSPG | SEQ ID NO: 44 |
| EVQLVQSGAEVKKPGSSVKVSCKAS<u>GFNIKDTYMH</u>WVRQAPGQGLEWIG<u>RI DPANGNTKYDPKFQG</u>RATITADTSTNTAYMELSSLRSEDTAVYYCAR<u>GGPA WFVY</u>WGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKEYKCKVS NKALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQKSLSLSPGK | SEQ ID NO: 45 |
| EVQLVQSGAEVKKPGSSVKVSCKAS<u>GFNIKDTYMH</u>WVRQAPGQGLEWIG<u>RI DPANGNTKYDPKFQG</u>RATITADTSTNTAYMELSSLRSEDTAVYYCAR<u>GGPA WFVY</u>WGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHED | SEQ ID NO: 46 |

TABLE 6-continued

Exemplary Heavy Chain Sequences

| Sequence | Identifier |
|---|---|
| PEVKFNWYVDGVEVHNAKTKPREEQYNSTYRVVSVLTVLHQDWLNGKEYKCKVS NKALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALHN HYTQKSLSLSPG | |
| EVQLVESGGGLVQPGGSLRLSCAVSGFSLTSYGVHWVRQAPGKGLEWLGVI WSGGSTDYNAAFISRLTISKDNSKSTVYLQMNSLRAEDTAVYYCAREEFDYW GQGTTVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK | SEQ ID NO: 47 |
| EVQLVESGGGLVQPGGSLRLSCAVSGFSLTSYGVHWVRQAPGKGLEWLGVI WSGGSTDYNAAFISRLTISKDNSKSTVYLQMNSLRAEDTAVYYCAREEFDYW GQGTTVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPG | SEQ ID NO: 48 | and a light chain amino acid sequence as described in TABLE 7:

TABLE 7

Exemplary Light Chain Sequences

| Sequence | Identifier |
|---|---|
| DIVMTQSPDSLAVSLGERATINCKASQSVDYDGDSYMHWYQQKPGQPPKLLI YAASILESGVPDRFSGSGSGTDFTLTISSLQAEDVAVYYCQQSNEDPRTFGGG TKVEIKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFNRGEC | SEQ ID NO: 51 |
| DIQMTQTPSSLSASVGDRVTITCRASQDISNYLNWYQQKPGKAPKLLIFYTSR LHSGVPSRFSGSGSGTDYTLTISSLQPEDFATYYCQQGNTLPLTFGQGTKLEIK RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC | SEQ ID NO: 52 |
| DIQMTQSPSSLSASVGDRVTITCRASQDISNYLNWYQQKPGKAPKLLIYYTSR LRSGLPSRFSGSGSGTDYTLTISSLQPEDFATYYCQQGNTLPWTFGGGTKVEIK RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC | SEQ ID NO: 53 |
| DIQMTQSPSSLSASVGDRVTITCRASQDISNYLNWFQQKPGKAPKLLIYYTSR LHSGVPSRFSGSGSGTDYTLTISSLQPEDFATYYCQQGYTLPPTFGGGTKVEIK RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC | SEQ ID NO: 54 | wherein the underlined amino acids represent the CDRs and the italicized amino acids represent the constant regions.

In some embodiments, an anti-OX40 antibody comprises a heavy chain amino acid sequence according to SEQ ID NO:41 or 42, and a light chain amino acid sequence according to SEQ ID NO:51. In some embodiments, an anti-OX40 antibody comprises a heavy chain amino acid sequence according to SEQ ID NO:43 or 44, and a light chain amino acid sequence according to SEQ ID NO:52. In some embodiments, an anti-OX40 antibody comprises a heavy chain amino acid sequence according to SEQ ID NO:45 or 46, and a light chain amino acid sequence according to SEQ ID NO:53. In some embodiments, an anti-OX40 antibody comprises a heavy chain amino acid sequence according to SEQ ID NO:47 or 48, and a light chain amino acid sequence according to SEQ ID NO:54.

In some embodiments, an anti-OX40 antibody comprises a heavy chain sequence having at least 85%, at least 90%, at least 93%, at least 95%, at least 96%, at least 97%, at least 98%, or at least 99% sequence identity to the heavy chain sequence according to any one of SEQ ID NOS:41-48. An anti-OX40 antibody can comprise a heavy chain sequence having up to 8, up to 7, up to 6, up to 5, up to 4, up to 3, or up to 2 mutations compared with the heavy chain sequence according to any one of SEQ ID NOS:41-48. In some embodiments, an anti-OX40 antibody can comprise a heavy chain sequence having 5 or fewer, 4 or fewer, 3 or fewer, or 2 or fewer mutations compared with the heavy chain sequence according to any one of SEQ ID NOS:41-48.

In some embodiments, an anti-OX40 antibody comprises a light chain sequence having at least 85%, at least 90%, at least 93%, at least 95%, at least 96%, at least 97%, at least 98%, or at least 99% sequence identity to the light chain sequence according to any one of SEQ ID NOS:51-54. An anti-OX40 antibody can comprise a light chain sequence having up to 8, up to 7, up to 6, up to 5, up to 4, up to 3, or up to 2 mutations compared with the light chain sequence according to any one of SEQ ID NOS:51-54. In some embodiments, an anti-OX40 antibody can comprise a light chain sequence having 5 or fewer, 4 or fewer, 3 or fewer, or 2 or fewer mutations compared with the light chain sequence according to any one of SEQ ID NOS:51-54.

Additional post-translational modifications of an anti-OX40 antibody may include glycosylation. Common biantennary complexes can be composed of a core structure having two N-acetylglucosamine (GlcNAc), three mannose, and two GlcNAc residues that are β-1,2 linked to α-6 mannose and α-3 mannose to form two antennae. One or more fucose (Fuc), galactose (Gal), high mannose glycans Man-5 or Man-9, bisecting GlcNAc, and sialic acid including N-acetylneuraminic acid (NANA) or N-glycolylneuraminic acid (NGNA) residues may be attached to the core. N-linked glycoforms may include G0 (protein having a core biantennary glycosylation structure), G0F (fucosylated G0), G0F GlcNAc, G1 (protein having a core glycosylation structure with one galactose residue), G1F (fucosylated G1), G2 (protein having a core glycosylation structure with two galactose residues), and/or G2F (fucosylated G2).

In some embodiments, the anti-OX40 antibodies compete for binding human OX40 (SEQ ID NO:1) in in vitro assays with a reference antibody. In some embodiments, the anti-OX40 antibodies compete for binding human OX40 on cells expressing human OX40. The reference antibody may be any of the anti-OX40 antibodies described herein. In some embodiments, the reference antibody is an antibody having a $V_H$ according to one described in TABLE 4 and a $V_L$ according to one described in TABLE 5. In specific embodiments, the reference antibody is mouse antibody comprising Mu3726 $V_H$ and Mu3726 $V_L$ ("Mu3726"), mouse antibody comprising Mu3738 $V_H$ and Mu3738 $V_L$ ("Mu3738"), mouse antibody comprising Mu3739 $V_H$ and Mu3739 $V_L$ ("Mu3739"), or mouse antibody comprising Mu3741 $V_H$ and Mu3741 $V_L$ ("Mu3741"). In some embodiments, the reference antibody is a humanized version of Mu3726, Mu3738, Mu3739, or Mu3741. In certain embodiments, the reference antibody is a humanized antibody comprising a heavy chain according to SEQ ID NO:41 or 42 and a light chain according to SEQ ID NO:51 ("Hu3738"), a humanized antibody comprising a heavy chain according to SEQ ID NO:43 or 44 and a light chain according to SEQ ID NO:52 ("Hu3726"), a humanized antibody comprising a heavy chain according to SEQ ID NO:45 or 46 and a light chain according to SEQ ID NO:53 ("Hu3739"), or a humanized antibody comprising a heavy chain according to SEQ ID NO:47 or 48 and a light chain according to SEQ ID NO:54 ("Hu3741").

The anti-OX40 antibodies described herein generally bind specifically to human OX40. Cross reactivity of the antibodies for binding to OX40 from other species, for example, from monkey, e.g., cynomolgus monkey, may offer advantages, such as the ability to test in monkey animal models for biological activity. Such animal model testing may be used to screen anti-OX40 antibodies to select properties related to efficacy, e.g., favorable pharmacokinetics, or those related to safety, e.g., decreased hepatic toxicity. In some embodiments, an anti-OX40 antibody binds to cynomolgus OX40 (SEQ ID NO:2) (NCBI Reference Sequence XP005545179) as well as human OX40. In some embodiments, an anti-OX40 antibody does not bind to mouse OX40 (SEQ ID NO:3) (NCBI Reference Sequence NP037181).

Assays for competition include, but are not limited to, a radioactive material labeled immunoassay (RIA), an enzyme-linked immunosorbent assay (ELISA), a sandwich ELISA, fluorescence activated cell sorting (FACS) assays, and surface plasmon resonance assays.

Surface plasmon resonance (SPR) assays allow for direct measurement of binding kinetics between two proteins, e.g., a receptor and an antibody, such as human OX40 receptor and an anti-OX40 antibody, without the need for a reporter signal or tag. Both the equilibrium dissociation constant $K_D$, a measure of binding affinity, as well as its two components—the binding kinetic rate constants, $k_a$ ($M^{-1}\text{-sec}^{-1}$) (association constant, $k_{on}$, or "on rate") and $k_d$ ($\text{sec}^{-1}$) (dissociation constant, $k_{off}$, or "off rate")—can be determined using SPR. The constants are related by the following equation:

$$K_D = k_d/k_a.$$

In some embodiments, the anti-OX40 antibodies have a $K_D$ of at least about 100 nM, but may exhibit higher affinity, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the anti-OX40 antibody has a $K_D$ in the range of about 1 pM to about 100 nM, or an affinity ranging between any of the foregoing values, such as but not limited to from about 0.001 to 10 nM, 0.001 to 5 nM, 0.01 to 100 nM, 0.01 to 50 nM, 0.01 to 10 nM, 0.01 to 5 nM, or about 0.01 to 1 nM.

In some embodiments, an anti-OX40 antibody has a dissociation constant $k_d$ no more than about 10 $\text{sec}^{-1}$, for example, no more than about 1, 0.5, 0.2, 0.1, 0.05, 0.01, 0.005, 0.001 $\text{sec}^{-1}$, or even lower. In some embodiments, the anti-OX40 antibody has a $k_d$ in the range of about 0.001 $\text{sec}^{-1}$ to about 10 $\text{sec}^{-1}$, or a $k_d$ ranging between any of the foregoing values, such as but not limited to from about 0.01 to 10 $\text{sec}^{-1}$, 0.001 to 0.5 $\text{sec}^{-1}$, 0.001 to 0.2 $\text{sec}^{-1}$, 0.001 to 0.1 $\text{sec}^{-1}$, 0.01 to 1 $\text{sec}^{-1}$, 0.001 to 0.05 $\text{sec}^{-1}$, or about 0.001 to 1 $\text{sec}^{-1}$.

In some embodiments, an anti-OX40 antibody has an association constant $k_a$ at least about $10^4$ $M^{-1}\text{-sec}^{-1}$, for example, at least about $1\times10^4$, $5\times10^4$, $1\times10^5$, $5\times10^5$, $1\times10^6$, $5\times10^6$, $1\times10^7$ $M^{-1}\text{-sec}^{-1}$, or even greater. In some embodiments, the anti-OX40 antibody has a $k_d$ in the range of about $10^4$ $M^{-1}\text{-sec}^{-1}$ to about $10^7$ $M^{-1}\text{-sec}^{-1}$, or a $k_a$ ranging between any of the foregoing values, such as but not limited to from about $5\times10^4$ to $1\times10^7$ $M^{-1}\text{-sec}^{-1}$, $5\times10^4$ to $5\times10^6$ $M^{-1}\text{-sec}^{-1}$, or about $1\times10^4$ to $5\times10^6$ $M^{-1}\text{-sec}^{-1}$.

An anti-OX40 antibody of the disclosure may exhibit a $K_D$, $k_d$, or $k_a$ in a range around a binding kinetics constant measured for any one of the exemplary anti-OX40 antibodies described herein. For example, in some embodiments, an anti-OX40 antibody has a dissociation constant $k_d$ in a range of from about 0.01 to about 100-fold, e.g., about 0.1 to about 10-fold, or about 0.5 to about 5-fold, the $k_d$ of any one of Hu3738, Hu3726, Hu3739, and Hu3741. In some embodiments, an anti-OX40 antibody has an association constant $k_a$ in a range of from about 0.01 to about 100-fold, e.g., about 0.1 to about 10-fold, or about 0.5 to about 5-fold, the $k_a$ of any one of Hu3738, Hu3726, Hu3739, and Hu3741.

In conducting an antibody competition assay between a reference antibody and a test antibody (irrespective of species or isotype), one may first label the reference with a detectable label, such as a fluorophore, biotin or an enzymatic (or even radioactive) label to enable subsequent identification. In this case, cells expressing human OX40 are incubated with unlabeled test antibody, labeled reference antibody is added, and the intensity of the bound label is measured. If the test antibody competes with the labeled reference antibody by binding to an overlapping epitope, the intensity will be decreased relative to a control reaction carried out without test antibody.

In a specific embodiment of this assay, the concentration of labeled reference antibody that yields 80% of maximal binding ("conc$_{80\%}$") under the assay conditions (e.g., a specified density of cells) is first determined, and a competition assay carried out with 10× conc$_{80\%}$ of unlabeled test antibody and conc$_{80\%}$ of labeled reference antibody.

The inhibition can be expressed as an inhibition constant, or K which is calculated according to the following formula:

$$K_i = IC_{50}/(1+[\text{reference Ab concentration}]/K_d),$$

where IC$_{50}$ is the concentration of test antibody that yields a 50% reduction in binding of the reference antibody and K$_d$ is the dissociation constant of the reference antibody, a measure of its affinity for human OX40. Antibodies that compete with anti-OX40 antibodies disclosed herein can have a K$_i$ from 10 pM to 100 nM under assay conditions described herein.

In various embodiments, a test antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

A specific assay and assay conditions useful for assessing whether an antibody competes for binding human OX40 with a reference antibody as described herein is provided in Section 8.1.4.

In some embodiments, the anti-OX40 antibodies of the disclosure activate human OX40 (SEQ ID NO:1). OX40 receptor activation can occur by a number of mechanisms, for example, by affording ligand-like activity against OX40 receptor. In such cases, an anti-OX40 antibody competes for binding to OX40 receptor with human OX40 ligand (OX40L, CD252; UniProtKB/Swiss-Prot Code P23510.1) (SEQ ID NO:4).

An anti-OX40 antibody of the disclosure can generally activate OX40 receptor in the presence of cross-linking. A specific assay and assay conditions useful for assessing whether an anti-OX40 antibody can activate OX40 receptor, e.g., human OX40 receptor (SEQ ID NO:1), in the presence of cross-linking is provided in Section 8.1.8. In some embodiments, an anti-OX40 antibody activates human OX40 receptor in the presence of cross-linking with an EC$_{50}$ of from about 1 pM to about 500 nM, such as but not limited to from about 0.01 to about 300 nM, from about 0.01 to about 100 nM, from about 0.01 to about 10 nM, from about 0.01 to about 1 nM, from about 0.1 to about 300 nM, from about 0.1 nM to about 100 nM, from about 1 nM to about 100 nM, or from about 0.1 nM to about 100 nM. In some embodiments, an anti-OX40 antibody at 100 µg/mL can activate human OX40 receptor in the presence of cross-linking to an activity at least about 3-fold, such as from about 3 to about 1000, e.g., about 5, 10, 15, 20, 30, 40, 50, 60, 80, 100, 200, 400, 500, 700, 800 or about 1000-fold higher compared with the activity of human OX40 receptor in the absence of the anti-OX40 antibody.

Cross-linking can be provided by a number of methods, including addition of exogenous cross-linker, e.g., by antibodies or antibody F(ab')$_2$ fragments specific for heavy, light or variable regions of human or humanized antibodies; by soluble or immobilized protein A; by Fc receptor transfected cell lines; by endogenous Fc receptor expressing cell lines; by directly coating the subject antibodies to plastic surfaces; by plastic surfaces coated with exogenous cross-linking antibodies or Fc receptors; or by beads conjugated to any of the above. In an illustrative example, subject antibodies can be conjugated to a protein such as biotin, and soluble or immobilized avidin or streptavidin is used as a cross-linker. In another example, in human lymph nodes in vivo, the activation of OX40 after binding to an anti-OX40 antibody is expected to occur after receptor cross-linking provided by endogenous FcγR+ antigen-presenting cells.

In some embodiments, an anti-OX40 antibody binds to and activates human OX40 receptor in the absence of cross-linking. In some embodiments, an anti-OX40 antibody activates OX40 receptor, e.g., human OX40 receptor (SEQ ID NO:1), in the absence of OX40L, e.g., human OX40L (SEQ ID NO:4). A specific assay and assay conditions useful for assessing whether an anti-OX40 antibody can activate OX40 receptor without cross-linking is provided in Section 8.1.8. In some embodiments, an anti-OX40 antibody activates human OX40 receptor without cross-linking with an EC$_{50}$ of from about 1 pM to about 500 nM, such as but not limited to from about 0.01 to about 300 nM, from about 0.01 to about 100 nM, from about 0.1 to about 300 nM, from about 0.1 nM to about 100 nM, from about 1 nM to about 100 nM, from about 0.1 nM to about 100 nM, from about 1 to about 300 nM, from about 1 to about 100 nM, from about 1 to about 50 nM, or from about 10 to about 100 nM. In some embodiments, an anti-OX40 antibody at 100 µg/mL can activate human OX40 receptor without cross-linking to an activity at least about 5-fold, such as from about 5 to about 1000, e.g., about 5, 10, 15, 20, 30, 40, 50, 60, 80, 100, 200, 300, 400, 500, 700, 800 or about 1000-fold higher compared with the activity of human OX40 receptor dosed with an equivalent amount of isotype antibody. In some embodiments, an anti-OX40 antibody at 10 µg/mL can activate human OX40 receptor without cross-linking to an activity at least about 3-fold, such as from about 3 to about 300, e.g., about 3, 5, 6, 8, 10, 12, 15, 20, 25, 30, 40, 50, 60, 80, 100, 200, or about 300-fold higher compared with the activity of human OX40 receptor dosed with an equivalent amount of isotype antibody. In some embodiments, an anti-OX40 antibody at 1 µg/mL can activate human OX40 receptor without cross-linking to an activity at least about 3-fold, such as from about 3 to about 150, e.g., about 3, 4, 5, 6, 7, 8, 10, 12, 15, 20, 25, 30, 40, 50, 60, 80, 100, or about 150-fold higher compared with the activity of human OX40 receptor dosed with an equivalent amount of isotype antibody.

In some embodiments, an anti-OX40 antibody activates OX40 receptor, e.g., human OX40 receptor (SEQ ID NO:1), at a higher level in the presence of cross-linking compared to without cross-linking. A specific assay and assay conditions useful for determining the level at which an anti-OX40 antibody can activate OX40 receptor without cross-linking is provided in Section 8.1.8. The level of activity can be measured, for example, in terms of EC$_{50}$ and/or an observed maximal activation. In some embodiments, the anti-OX40 antibody at 100 µg/mL activates OX40 receptor, e.g., human OX40 receptor (SEQ ID NO:1), without cross-linking at from about 20% to about 95% of NF-κB activity, such as about 25%, 30%, 40%, 50%, 60%, 70%, 80%, or about 90%, as compared to the NF-κB activity with cross-linking in an assay according to Section 8.1.8.

In some embodiments, an anti-OX40 antibody activates human OX40 receptor without cross-linking with an $EC_{50}$ of from about 0.1 nM to about 500 nM, such as but not limited to from about 1 nM to about 100 nM, from about 0.1 nM to about 100 nM, from about 1 to about 300 nM, from about 1 to about 100 nM, from about 1 to about 50 nM, or from about 10 to about 100 nM, in an assay according to Section 8.1.8. In some such embodiments, an anti-OX40 antibody at 10 μg/mL can activate human OX40 receptor without cross-linking to an activity at least about 3-fold, such as from about 3 to about 300, e.g., about 3, 5, 6, 8, 10, 12, 15, 20, 25, 30, 40, 50, 60, 80, 100, 200, or about 300-fold higher compared with the activity of human OX40 receptor dosed with an equivalent amount of isotype antibody. In some such embodiments, an anti-OX40 antibody activates human OX40 receptor in the presence of cross-linking with an $EC_{50}$ of from about 1 pM to about 300 nM, such as but not limited to from about 0.01 to about 300 nM, from about 0.01 to about 100 nM, from about 0.01 to about 10 nM, from about 0.01 to about 1 nM, from about 0.1 to about 300 nM, from about 0.1 nM to about 100 nM, from about 1 nM to about 100 nM, or from about 0.1 nM to about 100 nM, in an assay according to Section 8.1.8. In some such embodiments, an anti-OX40 antibody can activate human OX40 receptor in the presence of cross-linking at a lower $EC_{50}$, such as from about 1.5 to about 100-fold, such as from about 1.5 to about 10-fold, e.g., about 2, 3, 4, 5, 6, 7, 8, 9, or about 10-fold lower, compared with the $EC_{50}$ of antibody 1A7 described in US publication no. 2015/0307617 in an assay according to Section 8.1.8.

An anti-OX40 antibody of the invention can activate human OX40 receptor without cross-linking with an $EC_{50}$ of from about 1 nM to about 100 nM in an assay according to Section 8.1.8, and can activate human OX40 receptor in the presence of cross-linking at a lower $EC_{50}$, such as from about 1.5 to about 10-fold lower, compared with the $EC_{50}$ of antibody 1A7 described in US publication no. 2015/0307617 in an assay according to Section 8.1.8. Exemplary anti-OX40 antibodies having the above-recited properties include Mu3738 and Hu3738 as described in Examples 2 through 8 herein.

Generally, OX40 activation upon treatment with an anti-OX40 antibody results in a signal transduction, such as an increase in cytokine production (e.g., interferon-gamma (IFN-γ)) and/or an increase in cell proliferation, e.g., CD4+ T cell proliferation. In some embodiments, the increase in IFN-γ production after treatment with 1 μg/mL of an anti-OX40 antibody is from about 1.5 to about 50 times, such as about 1.5, 2, 3, 4, 5, 6, 8, 10, 15, 20, 25, 30, 40, or about 50 times the level of IFN-γ production after treatment with an equivalent amount of an isotype antibody. In some embodiments, the increase in CD4+ T cell proliferation after treatment with 1 μg/mL of an anti-OX40 antibody is from about 1.5 to about 20 times, such as about 1.5, 2, 3, 4, 5, 6, 8, 10, 15, or about 20 times the level of CD4+ T cell proliferation after treatment with an equivalent amount of an isotype antibody. Assays for determining cytokine levels or for determining cell proliferation levels are known in the art. A specific assay and assay conditions for determining IFN-γ production and/or CD4+ T cell proliferation is provided herein in Section 8.1.12.

7.4. Polynucleotides Encoding the Anti-OX40 Antibodies, Expression Systems and Methods of Making the Same The present disclosure encompasses nucleic acid molecules encoding immunoglobulin light and heavy chain genes for anti-OX40 antibodies, vectors comprising such nucleic acids, and host cells capable of producing the anti-OX40 antibodies of the disclosure.

An anti-OX40 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

To generate nucleic acids encoding such anti-OX40 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836).

Once DNA fragments encoding anti-OX40 antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2, CH3 and, optionally, CH4). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region. To create a scFv gene, the $V_H$- and $V_L$-encoding DNA fragments are operatively linked to another fragment encoding a flexible linker, e.g., encoding the amino acid sequence $(Gly_4\text{~}Ser)_3$ (SEQ ID NO:60), such that the $V_H$ and $V_L$ sequences can be expressed as a contiguous single-chain protein, with the $V_L$ and $V_H$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-OX40 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-OX40 antibody-related light or heavy chain sequences, the expression vector can already carry antibody constant region sequences. For example, one approach to converting the anti-OX40 monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the anti-OX40 antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce anti-OX40 binding fragments of antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-OX40 antibody of this disclosure.

Recombinant DNA technology can also be used to remove some or all of the DNA encoding either or both of the light and heavy chains that is not necessary for binding to human OX40. The molecules expressed from such truncated DNA molecules are also encompassed by the antibodies of the disclosure.

For recombinant expression of an anti-OX40 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-OX40 antibody has been obtained, further alterations or mutations can be introduced into the coding sequence, for example to generate nucleic acids encoding antibodies with different CDR sequences, antibodies with reduced affinity to the Fc receptor, or antibodies of different subclasses.

The anti-OX40 antibodies of the disclosure can also be produced by chemical synthesis (e.g., by the methods described in Solid Phase Peptide Synthesis, $2^{nd}$ ed., 1984 The Pierce Chemical Co., Rockford, Ill.). Variant antibodies can also be generated using a cell-free platform (See, e.g., Chu et al., Biochemia No. 2, 2001 (Roche Molecular Biologicals) and Murray et al., 2013, Current Opinion in Chemical Biology, 17:420-426).

Once an anti-OX40 antibody of the disclosure has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-OX40 antibodies of the present disclosure can be fused to heterologous polypeptide sequences described herein or otherwise known in the art to facilitate purification.

Once isolated, the anti-OX40 antibody can, if desired, be further purified, e.g., by high performance liquid chromatography (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

7.5. Pharmaceutical Compositions

The anti-OX40 antibodies described herein may be in the form of compositions comprising the antibody and one or more carriers, excipients and/or diluents (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). The compositions may be formulated for specific uses, such as for veterinary uses or pharmaceutical uses in humans. The form of the composition (e.g., dry powder, liquid formulation, etc.) and the carriers used will depend upon the intended uses of the antibody and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as intravenously, intratumorally, or intrathecally.

The most suitable route for administration in any given case will depend on the particular antibody, the subject, and the nature and severity of the disease and the physical condition of the subject. Typically, the pharmaceutical composition will be administered intravenously.

Pharmaceutical compositions can be conveniently presented in unit dosage forms containing a predetermined amount of an anti-OX40 antibody described herein per dose. The quantity of anti-OX40 antibody included in a unit dose will depend on the disease being treated, as well as other factors as are well known in the art. Such unit dosages may be in the form of a lyophilized dry powder containing an amount of antibody suitable for a single administration, or in the form of a liquid. Dry powder unit dosage forms may be packaged in a kit with a syringe, a suitable quantity of carrier and/or other components useful for administration. Unit dosages in liquid form may be conveniently supplied in the form of a syringe pre-filled with a quantity of the anti-OX40 antibody suitable for a single administration.

The pharmaceutical compositions may also be supplied in bulk form containing quantities of anti-OX40 antibody suitable for multiple administrations.

Pharmaceutical compositions may be prepared for storage as lyophilized formulations or aqueous solutions by mixing an antibody having the desired degree of purity with optional pharmaceutically-acceptable carriers typically employed in the art. Such additives should be nontoxic to the recipients at the dosages and concentrations employed.

For example, for intravenous administration, the composition may be in the form of a lyophilized powder that, upon reconstitution with sterile water or other solution suitable for injection or infusion (for example, 0.9% saline, Ringer's solution, lactated Ringer's solution, etc.) provides an aqueous composition.

7.6. Methods of Use 7.6.1. Therapeutic Benefit

Data provided herein demonstrate that the disclosed anti-OX40 antibodies activate OX40 receptor in the presence of cancer cells and exert potent anticancer activity against cancer in vivo. Accordingly, the anti-OX40 antibodies and/or pharmaceutical compositions comprising the anti-OX40 antibodies may be used therapeutically to treat cancers.

In some embodiments, the cancer is a solid tumor. Solid tumors that may be treated with the anti-OX40 antibody include bladder cancer, breast cancer (e.g., triple negative breast cancer), head and neck cancer, kidney cancer (e.g., renal cell carcinoma), liver cancer (e.g., hepatocellular carcinoma, cholangiocarcinoma), lung cancer (e.g., non-small cell lung cancer, mesothelioma, small cell lung cancer), melanoma (e.g., unresectable or metastatic melanoma, advanced malignant melanoma), skin cancer (e.g., Merkel cell carcinoma), ovarian cancer, gastric cancer, and tumors with evidence of DNA mismatch repair deficiency. The cancer may be comprised of tumors containing OX40-expressing cells; comprised of tumors, some of which contain OX40-expressing cells and some of which do not; or comprised of tumors lacking OX40-expressing cells. The cancer may be newly diagnosed and naïve to treatment, or may be relapsed, refractory, or relapsed and refractory, or a metastatic form of a solid tumor. In some embodiments, the solid tumor is naïve to a PD-1 or PD-L1 targeting agent. In other embodiments, the solid tumor is relapsed or refractory after treatment with a PD-1 or PD-L1 targeting agent. In some embodiments, the solid tumor is selected from bladder cancer, breast cancer, head and neck cancer, kidney cancer, lung cancer, melanoma, and gastric cancer. In some embodiments, the solid tumor is selected from: melanoma (e.g., unresectable or metastatic melanoma), lung cancer (e.g., non-small cell lung cancer), and renal cell carcinoma (e.g., advanced renal cell carcinoma). In some embodiments, the solid tumor is selected from triple negative breast cancer, ovarian cancer, hepatocellular carcinoma, gastric cancer, small cell lung cancer, mesothelioma, cholangiocarcinoma, Merkel cell carcinoma and tumors with evidence of DNA mismatch repair deficiency. In certain embodiments, the lung cancer is metastatic non-small cell lung cancer with progression on or after platinum-based chemotherapy. In certain embodiments, the lung cancer is locally advanced or metastatic non-small cell lung cancer that has failed platinum-based therapy and therapy with a PD-1 or PD-L1 targeting agent. In certain embodiments, the head and neck cancer is recurrent squamous cell head and neck carcinoma that is not a candidate for curative treatment with local or systemic therapy, or metastatic (disseminated) head and neck squamous cell carcinoma of the oral cavity, oropharynx, hypopharynx, and larynx that is considered incurable by local therapies.

As discussed above, the presently disclosed anti-OX40 antibodies modulate an immunological response. Accordingly, patients having compromised immune systems may be excluded from treatment. In some embodiments, a patient is excluded after meeting one or more of the following criteria: (1) Active or prior documented autoimmune disease (including, but not limited to, inflammatory bowel disease, celiac disease, Wegener syndrome) within the past 2 years. (Subjects with childhood atopy or asthma, vitiligo, alopecia, Hashimoto syndrome, Grave's disease, or psoriasis not requiring systemic treatment (within the past 2 years) are not excluded); (2) History of primary immunodeficiency, bone marrow transplantation, chronic lymphocytic leukemia, solid organ transplantation, or previous clinical diagnosis of tuberculosis; (3) History of a coagulopathy or a platelet disorder; (4) Confirmed positive test results for human immunodeficiency virus (HIV), or subjects with chronic or active hepatitis B or C. (Subjects who have a history of hepatitis B or C who have documented cures after anti-viral therapy may be enrolled); (5) Prior grade ≥3 immune-mediated neurotoxicity or pneumonitis while receiving immunotherapy (including but not limited to agents directed against CTLA-4, PD-L1, or PD-1). In addition, any other prior grade ≥3 immune-mediated adverse event while receiving immunotherapy that has not resolved or become asymptomatic within 3 months; (6) Receipt of live, attenuated vaccine within 28 days prior to the first dose of the anti-OX40 antibody.

An anti-OX40 antibody of the disclosure may be administered alone (monotherapy) or adjunctive to, or with, other anti-cancer therapies and/or targeted or non-targeted anti-cancer agents. When administered as an anti-OX40 monotherapy, one or more antibodies may be used. Whether administered as monotherapy or adjunctive to, or with, other therapies or agents, an amount of anti-OX40 antibody is administered such that the overall treatment regimen provides therapeutic benefit.

By therapeutic benefit is meant that the use of anti-OX40 antibodies to treat cancer in a patient results in any demonstrated clinical benefit compared with no therapy (when appropriate) or to a known standard of care. Clinical benefit can be assessed by any method known to one of ordinary skill in the art. In one embodiment, clinical benefit is assessed based on objective response rate (ORR) (determined using RECIST version 1.1), duration of response (DOR), progression-free survival (PFS), and/or overall survival (OS). In some embodiments, a complete response indicates therapeutic benefit. In some embodiments, a partial response indicates therapeutic benefit. In some embodiments, stable disease indicates therapeutic benefit. In some embodiments, an increase in overall survival indicates therapeutic benefit. In some embodiments, therapeutic benefit constitutes an improvement in time to disease progression and/or an improvement in symptoms or quality of life. In other embodiments, therapeutic benefit does not translate to an increased period of disease control, but rather a markedly reduced symptom burden resulting in improved quality of life. As will be apparent to those of skill in the art, a therapeutic benefit may be observed using the anti-OX40 antibodies alone (monotherapy) or adjunctive to, or with, other anti-cancer therapies and/or targeted or non-targeted anti-cancer agents.

Typically, therapeutic benefit is assessed using standard clinical tests designed to measure the response to a new treatment for cancer. To assess the therapeutic benefits of the anti-OX40 antibodies described herein one or a combination of the following tests can be used: (1) the Response Evaluation Criteria In Solid Tumors (RECIST) version 1.1, (2) immune-related RECIST (irRECIST), (3) the Eastern Cooperative Oncology Group (ECOG) Performance Status, (4) immune-related response criteria (irRC), (5) disease evaluable by assessment of tumor antigens, (6) validated patient reported outcome scales, and/or (7) Kaplan-Meier estimates for overall survival and progression free survival.

Assessment of the change in tumor burden is an important feature of the clinical evaluation of cancer therapeutics. Both tumor shrinkage (objective response) and time to the development of disease progression are important endpoints in cancer clinical trials. Standardized response criteria, known as RECIST (Response Evaluation Criteria in Solid Tumors), were published in 2000. An update (RECIST 1.1) was released in 2009. RECIST criteria are typically used in clinical trials where objective response is the primary study endpoint, as well as in trials where assessment of stable disease, tumor progression or time to progression analyses are undertaken because these outcome measures are based on an assessment of anatomical tumor burden and its change over the course of the trial. TABLE 8 provides the definitions of the response criteria used to determine objective tumor response to a study drug, such as the anti-OX40 antibodies described herein.

TABLE 8

| Response | Criteria |
| --- | --- |
| Complete Response (CR) | Disappearance of all target lesions. Any pathological lymph nodes (whether target or non-target) must have reduction in short axis to <10 mm. |
| Partial Response (PR) | At least a 30% decrease in the sum of diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) | Neither sufficient shrinkage to qualify for PR nor sufficient increase to qualify for PD, taking as reference the smallest sum diameters while on study. |

Secondary outcome measures that can be used to determine the therapeutic benefit of the anti-OX40 antibodies described herein include, Objective Response Rate (ORR), Progression Free Survival (PFS), Overall Survival (OS), Duration of Overall Response (DOR), and Depth of Response (DpR). ORR is defined as the proportion of the participants who achieve a complete response (CR) or partial response (PR). PFS is defined as the time from the first dose date of an anti-OX40 antibody to either disease progression or death, whichever occurs first. OS is defined as the length of time from either the date of diagnosis or the start of treatment for a disease, that patients diagnosed with the disease are still alive. DOR is defined as the time from the participant's initial CR or PR to the time of disease progression. DpR is defined as the percentage of tumor shrinkage observed at the maximal response point compared to baseline tumor load. Clinical endpoints for both ORR and PFS can be determined based on RECIST 1.1 criteria described above.

Additional criteria that may be used for clinical evaluation specific to cancer patients undergoing immune therapy treatment include the standardized immune-related RECIST (ir-RECIST) criteria. See, e.g., Nishino, M. et al. *Eur. J. Radiol.*, 84(7), pages 1259-1268 (2015 July). These guidelines modified the RECIST 1.1 criteria above with consideration of potential immunomodulatory effects. TABLE 9 provides the definitions of the response criteria used to determine objective tumor response to an immunomodulatory drug, such as the anti-OX40 antibodies described herein.

TABLE 9

| Response | Criteria |
| --- | --- |
| Complete Response (irCR) | Complete disappearance of all measurable and non-measurable lesions. Lymph nodes must decrease to <10 mm in short axis. |
| Partial Response (irPR) | Decrease of ≥30% in total measured tumor burden relative to baseline, non-target lesions are irNN, and no unequivocal progression of new non-measurable lesions |
| Progressive Disease (irPD) | At least a 20% increase and at least 5 mm absolute increase in TMTB compared to nadir, or irPD for non-target or new non-measurable lesions. Confirmation of progression is recommended at least 4 weeks after the first irPD assessment. |
| Non-irCR or non-irPD (irNN) | No target disease was identified at baseline and at follow-up the patient fails to meet criteria for irCR or irPD |
| Stable Disease (irSD) | Neither sufficient shrinkage to qualify for irPR nor sufficient increase to qualify for irPD, taking as reference the smallest sum diameters while on study. |
| irNE | Used in exceptional cases where insufficient data exists. |

The ECOG Scale of Performance Status shown in TABLE 10 is used to describe a patient's level of functioning in terms of their ability to care for themselves, daily activity, and physical ability. The scale was developed by the Eastern Cooperative Oncology Group (ECOG), now part of the ECOG-ACRIN Cancer Research Group, and published in 1982.

TABLE 10

| Grade | ECOG Performance Status |
| --- | --- |
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities; up and about more than 50% of waking hours |
| 3 | Capable of only limited selfcare; confined to bed or chair more than 50% of waking hours |
| 4 | Completely disabled; cannot carry on any selfcare; totally confined to bed or chair |
| 5 | Dead |

Another set of criteria that can be used to characterize fully and to determine response to immunotherapeutic agents, such as antibody-based cancer therapies, is the immune-related response criteria (irRC), which was developed for measurement of solid tumors in 2009, and updated in 2013 (Wolchok, et al. Clin. Cancer Res. 2009; 15(23): 7412-7420 and Nishino, et al. Clin. Cancer Res. 2013; 19(14): 3936-3943). The updated irRC criteria are typically used to assess the effect of an immunotherapeutic agent, such as an anti-OX40 antibody described herein, on tumor burden, and defines response according to TABLE 11.

TABLE 11

| Response | Criteria |
| --- | --- |
| Complete Response (CR) | Disappearance of all target lesions in two consecutive observations not less than 4 weeks apart |
| Partial Response (PR) | At least a 30% decrease in the sum of the longest diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). (Note: the appearance of one or more new lesions is not considered progression. The measurement of new lesions is included in the sum of the measurements). |
| Stable Disease (SD) | Neither sufficient shrinkage to qualify for PR nor sufficient increase to qualify for PD, taking as reference the smallest sum diameters while on study. |

One exemplary therapeutic benefit resulting from the use of anti-OX40 antibodies described herein to treat solid tumors, whether administered as monotherapy or adjunctive to, or with, other therapies or agents, is a complete response. Another exemplary therapeutic benefit resulting from the use of anti-OX40 antibodies to treat solid tumors, whether administered as monotherapy or adjunctive to, or with, other therapies or agents, is a partial response.

Validated patient reported outcome scales can also be used to denote response provided by each patient through a specific reporting system. Rather than being disease focused, such outcome scales are concerned with retained function while managing a chronic condition. One non-limiting example of a validated patient reported outcome scale is PROMIS® (Patient Reported Outcomes Measurement Information System) from the United States National Institutes of Health. For example, PROMIS® Physical Function Instrument for adult cancer patients can evaluate self-reported capabilities for the functioning of upper extremities (e.g., dexterity), lower extremities (e.g., walking or mobility), and central regions (e.g., neck, back mobility), and includes routine daily activities, such as running errands.

Kaplan-Meier curves (Kaplan and Meier, J. Am. Stat. Assoc. 1958; 53(282): 457-481) can also be used to estimate overall survival and progression free survival for cancer patients undergoing anti-OX40 antibody therapy in comparison to standard of care.

7.6.2. Adjunctive Therapies

The anti-OX40 antibodies may be used adjunctive to, or with, other agents or treatments having anti-cancer properties, including standard of care therapies, such as an anti-PD-1 antibody therapy. When used adjunctively, the anti-OX40 antibody and other agent(s) may be formulated together in a single, combination pharmaceutical formulation, or may be formulated and administered separately, either on a single coordinated dosing regimen or on different dosing regimens. Agents administered adjunctive to or with the anti-OX40 antibodies will typically have complementary activities to the anti-OX40 antibodies such that the antibodies and other agents do not adversely affect each other.

7.7. Dosages and Administration Regimens

The amount of anti-OX40 antibodies administered will depend upon a variety of factors, including but not limited to, the particular type of cancer treated, the stage of the cancer being treated, the mode of administration, the frequency of administration, the desired therapeutic benefit, and other parameters such as the age, weight and other characteristics of the patient, etc. Determination of dosages effective to provide therapeutic benefit for specific modes and frequency of administration is within the capabilities of those skilled in the art.

Dosages effective to provide therapeutic benefit may be estimated initially from in vivo animal models. Suitable animal models for a wide variety of diseases are known in the art.

The anti-OX40 antibodies disclosed herein may be administered by any route appropriate to the condition to be treated. In some embodiments, the anti-OX40 antibody is any one of the humanized antibodies with a heavy chain having an amino acid sequence according to any one of SEQ ID NOS:41-48, and a light chain having an amino acid sequence according to any one of SEQ ID NO:51-54. In certain embodiments, the anti-OX40 antibody has a heavy chain having an amino acid sequence according to SEQ ID NO:41 or 42, and a light chain having an amino acid sequence according to SEQ ID NO:51. An anti-OX40 antibody will typically be administered parenterally, i.e., infusion, intravenous (IV), intrathecal, bolus, intratumoral injection or epidural (Shire et al., 2004, *J. Pharm. Sciences* 93(6):1390-1402). In one embodiment, an anti-OX40 antibody is provided as a lyophilized powder in a vial. Prior to administration, the lyophilized powder is reconstituted with sterile water for injection (SWFI) or other suitable medium to provide a solution containing anti-OX40 antibody. In some embodiments, the resulting reconstituted solution is further diluted with saline or other suitable medium for infusion and administered via an IV infusion once every two weeks, i.e., every 13, 14 or 15 days.

In some embodiments, the anti-OX40 antibody is administered as an IV infusion once every two weeks at 0.01 mg/kg, 0.1 mg/kg, 1.0 mg/kg, or 3.0 mg/kg.

When administered adjunctive to or with other agents, such as other chemotherapeutic agents, the anti-OX40 antibodies may be administered on the same schedule as the other agent(s), or on a different schedule. When administered on the same schedule, the anti-OX40 antibody may be administered before, after, or concurrently with the other agent.

As will be appreciated by those of skill in the art, the recommended dosages for the various agents described above may need to be adjusted to optimize patient response and maximize therapeutic benefit.

8. EXAMPLES

The following Examples, which highlight certain features and properties of the exemplary embodiments of the anti-OX40 antibodies described herein are provided for purposes of illustration, and not limitation.

Example 1

Materials and Methods 8.1.1. Anti-OX40 Antibody Binding to Human OX40 by ELISA

Immunolon 4×HB 96-well plates (Thermo Scientific) were coated with 1 μg/mL of human OX40-FC (R&D Systems) at 4° C. overnight. Plates were blocked with phosphate-buffered saline (PBS) containing 1% bovine serum albumin (BSA) for 30 minutes at room temperature and then washed three times with PBST (PBS with 0.1% Tween 20) using a plate washer. OX40-coated plates were then incubated with indicated concentrations of test antibody at room temperature for one hour. Plates were washed four times with PBST and then incubated for 1 hour at room temperature with 100 μL of goat anti-human Fab fragment specific—Biotin (Jackson ImmunoResearch) prepared to a dilution of 1:5000 in PBS containing 1% BSA. Plates were then washed five times in PBST and 100 μL of a 1:1000 dilution of streptavidin-horseradish peroxidase (HRP) (Thermo Scientific) was added to each well and incubated for 30 minutes at room temperature. Plates were subsequently washed five times in PBST and 100 μL of TMB One component (Surmodics) were added to each well and incubated at room temperature (RT) until color developed (approximately 5-10 minutes). Optical density (OD) was read at 650 nm (Molecular Devices Spectromax190).

8.1.2. Anti-OX40 Antibody Binding to Cynomolgus Monkey OX40 by ELISA

Immunolon 4×HB 96-well plates (Thermo Scientific) were coated with 1 μg/mL of Cyno OX40-Fc fusion at 4° C. overnight. Plates were blocked with PBS containing 1% bovine serum albumin (BSA) for 30 minutes at RT and then washed three times with PBST (PBS with 0.1% Tween 20). OX40-coated plates were then incubated with indicated concentrations of anti-OX40 antibody at room temperature for one hour. Plates were washed four times with PBST and then incubated for 1 hour at room temperature with 100 μL of goat anti-human FAB fragment specific—Biotin (Jackson ImmunoResearch) prepared to a dilution of 1:5000 in PBS containing 1% BSA. Plates were then washed five times in PBST and 100 μL of a 1:1000 dilution of streptavidin-HRP (Thermo Scientific) was added to each well and incubated for 30 minutes at room temperature. Plates were then washed five times in PBST and 100 μL of TMB One component (Surmodics) were added to each well and incubated at room temperature until color developed (approximately 5-10 minutes). Optical density (OD) was read at 650 nm (Molecular Devices Spectromax190).

8.1.3. Anti-OX40 Antibody Binding to Rhesus OX40 by Flow Cytometry

Rhesus macaque (*Macaca mulatta*) OX40 is identical to cynomolgus monkey (*Macaca fascicularis*) OX40 (SEQ ID NO:2) at the amino acid level. A 293 NF-κB reporter cell line expressing rhesus OX40 was cultured in Dulbecco's modified Eagle media (DMEM) containing 10% fetal bovine serum (FBS) and Penicillin/Streptomycin. For the binding assay, cells were resuspended at 5 million cells per mL. 50 µL (250,000 cells)/well were transferred to each well of a 500 µL polypropylene 96-well plate (Nunc). A 2× stock of test anti-OX40 antibody or isotype control monoclonal antibody was prepared in a separate dilution plate at 666, 333, 111, 37.03, 12.34, 4.11, 0.457, 0.152, 0.0508, 0.0169, 0.00564 nM in culture media. The monoclonal antibodies (50 µL/well) were transferred into respective wells of the assay plate. Cells were incubated with the primary antibodies for 30 minutes at 4° C. and washed twice with 250 µL/well of PBS by centrifuging at 800 rpm for 3 minutes. Bound antibody was detected with Cy5-Donkey anti-human IgG (H+L) (Jackson ImmunoResearch) diluted to 2 µg/mL (50 µL/well) in PBS for 30 minutes at 4° C. Cells were washed once with 250 µL/well of PBS, resuspended in PBS containing 1% Formaldehyde and analyzed on a dual laser FACSCalibur (Becton Dickinson).

8.1.4. Anti-OX40 Antibody Binding Affinity to Human and Rhesus OX40 by Surface Plasmon Resonance The binding kinetics of an anti-OX40 antibody to recombinant soluble OX40 ECD (extracellular domain) were determined by surface plasmon resonance-based measurements made on a Biacore T200 instrument (GE Healthcare) at 25° C. using an anti-Fc capture assay approach. Recombinant extracellular domains (ECDs) of human OX40 (residues 1-216) and rhesus macaque OX40 (residues 28-214) were purchased (Creative Biomart) and further purified by gel filtration using Superdex200 (GE Healthcare) in 10 mM 4-(2-hydroxyethyl)-1-piperazineethanesulfonic acid (HEPES), pH 7.4, 150 mM NaCl, 3 mM ethylenediaminetetraacetic acid (EDTA). Rhesus macaque (*Macaca mulatta*) OX40 is identical to cynomolgus monkey (*Macaca fascicularis*) OX40 (SEQ ID NO:2) at the amino acid level. Chip preparation and binding kinetic measurements were made in the assay buffer HBS-EP+ (10 mM HEPES, pH 7.4, 150 mM NaCl, 3 mM EDTA, 0.05% Tween 20). For anti-Fc capture chip preparation, approximately 2000 Resonance Units (RU) of goat anti-human IgG Fc polyclonal antibody (Thermo Fisher Scientific Inc.), diluted to 25 µg/mL in 10 mM sodium acetate (pH 4.5), was directly immobilized across a CM5 biosensor chip using a standard amine coupling kit according to manufacturer's instructions and procedures. Unreacted moieties on the biosensor surface were blocked with ethanolamine. For binding kinetics measurements each assay cycle consisted of the following steps: 1) capture of test anti-OX40 antibody on test surface only; 2) analyte injection (OX40 ECD or buffer only) over both reference and test surface, 240 µL at 80 µL/min, after which the dissociation was monitored for 900 seconds at 80 µL/min; 3) regeneration of capture surface by 10 mM Glycine-HCl, pH 1.5 injections over both reference and test surface. During the assay, all measurements were referenced against the capture surface alone (i.e., with no captured test antibody) and buffer-only injections were used for double referencing. OX40 injections ranged in concentration from 900 nM or 300 nM to 11.11 nM in a randomized 9- or 3-fold dilution series, respectively. Data were processed and fitted globally to a 1:1 binding model using Biacore T200 Evaluation software to determine the binding kinetic rate constants, $k_a$ ($M^{-1}s^{-1}$) and $k_d$ ($s^{-1}$), and the equilibrium dissociation constant $K_D$ (M).

8.1.5. OX40 Ligand Blocking with Anti-OX40 Antibody

Jurkat cells stably transfected with human OX40 cultured at 2×10$^5$ cells/well were simultaneously incubated with 0.2 µg/mL test anti-OX40 antibody and a titration of soluble human OX40L (R&D systems) in PBS containing 1% BSA in a round bottom 96-well plate for 30 minutes at RT. Cells were washed twice and incubated for an additional 30 minutes with 100 µL of 1:500 dilution of goat-anti-human Fc PE per well (Jackson ImmunoResearch). Cells were then washed twice and acquired using FACSCanto (BD Biosciences), and analyzed using FACSDiva.

8.1.6. Anti-OX40 Antibody Binding to Cell Surface Expressed Human OX40

A Jurkat NF-κB reporter cell line expressing human OX40 protein was cultured in DMEM containing 10% FBS and penicillin/streptomycin (pen/strep). For the binding assay, each cell line was resuspended at 5 million cells per mL. 50 µL (250,000 cells)/well were transferred to each well of a 500 µL polypropylene 96-well plate (Nunc). A 2× stock of test anti-OX40 antibody or isotype control mAb was prepared in a separate dilution plate at 666, 333, 111, 37.03, 12.34, 4.11, 0.457, 0.152, 0.0508, 0.0169, 0.00564 nM in culture media. Each antibody (50 µL/well) was transferred into respective wells of the assay plate. Cells were incubated with the test anti-OX40 antibody or isotype control antibodies for 30 minutes at 4° C. and washed twice with 250 µL/well of PBS by centrifuging at 800 rpm for 3 minutes. Bound antibody was detected with Cy5-Donkey anti-human IgG (H+L) (Jackson ImmunoResearch) diluted to 2 µg/mL (50 µL/well) in PBS for 30 minutes at 4° C. Cells were washed once with 250 µL/well of PBS, resuspended in PBS containing 1% Formaldehyde and analyzed on a dual laser FACSCalibur (Becton Dickinson).

8.1.7. Anti-OX40 Antibody Binding to Chimeric OX40 Receptor 293s-based transfectants were generated to express chimeric versions of the human OX40 molecule with mouse OX40 cysteine-rich domains (CRDs) individually swapped into corresponding human CRDs. After G418 selection, surviving cells were sorted for expression on the MoFlo flow cytometer (Beckman): 293s-huOX40, 293s-huOX40-muCRD1, 293s-huOX40-muCRDII, 293s-huOX40-muCRDIII, 293s-huOX40-muCRDIV, 293s-huOX40-muCRDII+III and 293s-muOX40. A total of 2×10$^5$ of each 293s OX40 chimeric transfectant cells were added per well into 500 µL polypropylene 96-well plates (Nunc). After plating cells, 50 µL of Hu3738 or isotype control antibody at 2 µg/mL were added to corresponding wells in duplicate for each cell line and allowed to incubate on ice for 30 minutes. Following incubation, 200 µL of Dulbecco's Phosphate Buffered Saline (DPBS) was added into each well and plates were spun down at 1000 rpm for three minutes. Supernatants from each well were removed and 50 µL of Cy5-Donkey anti-Human IgG (Jackson ImmunoResearch) secondary antibody was added at a 1:250 dilution, which was then incubated for 30 minutes on ice in the dark. Following the incubation period, 200 µL of DPBS was added prior to spinning down the plate at 1000 rpm for three minutes. Supernatants were removed and each well was re-suspended with 100 µL of DPBS+1% Formaldehyde. Samples were analyzed on the dual laser FACSCalibur flow cytometer (Becton Dickinson).

8.1.8. NF-κB Fluorescence Reporter Activity for Human and Rhesus OX40

Jurkat-NF-κB-huOX40 and 293-NF-κB-RhOX40, NF-κB reporter cell lines expressing the human and rhesus OX40 proteins, respectively, were maintained in culture media comprising DMEM containing 10% FBS and penicillin/streptomycin (100 U/mL). For the NF-κB reporter assay, the Jurkat-NF-κB-huOX40 cell line was resuspended in growth media (identical to culture media) at 1 million/mL (final 50,000 cells/well) and 293-NF-κB-RhOX40 cell line was resuspended in growth media at 0.5 million/mL (final 25,000 cells/well). 50 µL/well were transferred to the inner 60 wells of a white/clear bottom 96-well assay plate (Costar 3903). A 3× stock of the following antibodies were made in a separate U-bottom 96-well dilution plate (Becton Dickinson): anti-PD-1 antibody used as a negative control antibody, and anti-OX40 antibody. The dilution series to test the activity of the antibodies without exogenous cross-linker included 2000, 500, 125, 31.25, 7.812, 1.953, 0.488, 0.122, 0.0305, 0.00762 nM in culture media. The dilution series to test the effect of cross-linker on the activity of the anti-OX40 antibody included 200, 50, 12.5, 3.125, 0.7812, 0.1953, 0.0488, 0.0122, 0.00305, 0.000762 nM antibody. In duplicate, 50 µL/well of the antibodies were transferred into respective wells of the assay plate. To the antibody alone plates, 50 µL/well of media was added to the inner 60 wells. For the cross-linker dilution series, goat anti-human IgG Fc specific (Jackson ImmunoResearch) was diluted to 800, 200, 50, 12.5, 3.125, 0.7812, 0.1953, 0.0488, 0.0122, 0.00305 nM and 50 µL/well transferred to the inner 60 wells to maintain a 4:1 ratio of anti-OX40 antibody and cross-linker. Growth media (150 µL) was added to the outer wells to prevent evaporation in the inner 60 wells. Plates were incubated at 37° C. for approximately 18 hours. Luciferase activity was quantified with BriteLite Plus (Perkin Elmer). Briefly, substrate was dissolved with 10 mL of vendor-provided buffer and 75 µL substrate/well was added to the inner 60 wells of each plate. The plates were analyzed on the Victor5 (Molecular Devices) using the Luminescence settings.

8.1.9. ADCC Reporter Assay

ADCC effector cells expressing human FcγRIII (Promega) were thawed and grown as per protocol recommendations. Cells were split twice before use. HEK293 cells stably transfected with either human or rhesus OX40 were used as target cells. These cells were propagated in HyClone™ DMEM with 10% heat inactivated FBS (Sigma) and 5 µg/mL Blasticidin (Gibco Life Technologies).

On the day prior to the assay, OX40-expressing HEK293 target cells were harvested with 0.25% Trypsin (Gibco Life Technologies). Cells were washed, counted, and plated at 10,000 cells/well in 96-well Costar Plates (Corning). Plates were incubated at 37° C. overnight in DMEM 10% FBS. ADCC Bioassay Effector Cells, Propagation Model protocol G7102 was followed for the assay. Effector to Target cell ratio was 7.5:1. Luminescence was measured with EnSpire Alpha reader (Perkin Elmer) using EnSpireManager software. Antibodies that were tested in this assay included isotype control antibody and anti-OX40 antibodies.

8.1.10. Anti-OX40 Antibody Binding to Activated Human CD4+ T Cells

Human PBMCs were isolated from buffy coats purchased from Stanford Blood Center (Palo Alto, Calif.). Briefly, buffy coats were diluted in a 1:1 ratio with PBS without magnesium and calcium (GE Healthcare). Diluted blood (30 mL) was layered over 15 mL of 90% Ficoll-Paque Plus (GE Healthcare) prepared in PBS without magnesium and calcium (GE Healthcare) contained in SepMate tubes (Stemcell Technologies). The tubes were spun at 1200 g for 10 minutes. The interphase was collected and washed twice in 1×PBS. CD4+ T cells were isolated using Stemcell Technologies CD4 enrichment kit (Stem Cell Technologies). Cells were resuspended to $2\times10^6$ cells/mL in RPMI/10% FBS. Dynal CD3/28 beads (Life Technologies) were added at a 1:1 ratio. Cells were incubated on an end over end rotator at room temp for 20 minutes. The cells were cultured in 6-well plates for 24 hours at 37° C.

After 24 hours, the beads were removed with a magnet. Cells were counted and resuspended to $1.5\times10^6$/mL. An aliquot of the cell suspension (100 µL) was used per stain. Test antibody was titrated in a 4-fold dilution series starting at 1 µg/mL. Cells were stained for 30 minutes and washed twice. A 1:250 dilution of (4 µg/mL) of Goat anti Human Fc specific-PE/well (Jackson ImmunoResearch) was added in 100 µL/well PBS containing 1% BSA. Cells were stained for an additional 30 minutes and washed twice, transferred to tubes and acquired using the BD LSR Fortessa flow cytometer, and analyzed using FACSDiva analysis software version 8.0.1.

8.1.11 Anti-OX40 Antibody Binding to Activated Cynomolgus T Cells

Cynomolgus monkey whole blood was purchased from Worldwide Primates. For isolation of PBMCs, whole blood was diluted in a 1:1 ratio with PBS without magnesium and calcium (GE Healthcare). Diluted blood (30 mL) was layered under 13 mL of 95% Ficoll-Paque Plus (GE Healthcare) prepared in PBS without magnesium and calcium (GE Healthcare) in 50-mL conical tubes. The tubes were spun at 1000 g for 25 minutes. The interphase was collected and washed twice in 1×PBS. Cells were resuspended to $2\times10^6$ cells/mL in RPMI/10% FBS. Cells were incubated for 72 hours with 10 mg/mL phytohemagglutinin (PHA) (Sigma) and 100 U/mL recombinant human interleukin-2 (IL-2) (Proleukin®, Prometheus) in 6-well plates. After 24 hours, cells were washed, counted and resuspended to $2\times10^6$/mL. 100 µL of the cells were used per stain. Test anti-OX40 antibody was titrated in a 4-fold dilution series starting at 1 µg/mL. Cells were stained for 30 minutes and washed twice. A 1:250 dilution (4 µg/mL) of Goat anti-Human IgG Fc specific-PE (Jackson ImmunoResearch) in 100 µL PBS containing 1% BSA was added per well. Cells were stained for an additional 30 minutes and washed twice, transferred to tubes and acquired using the BD LSR Fortessa flow cytometer, and analyzed using FACSDiva analysis software version 8.0.1.

8.1.12. Activated Human T Cell Proliferation and IFN-γ Induction

Human buffy coats were purchased from Stanford Blood Center (Palo Alto, Calif.). For isolation of human PBMCs, buffy coats were diluted in a 1:1 ratio with PBS without magnesium and calcium (GE Healthcare). Diluted blood (30 mL) was layered over 15 mL of 90% Ficoll-Paque Plus (GE Healthcare) prepared in PBS without magnesium and calcium (GE Healthcare) contained in SepMate tubes (Stemcell Technologies). The tubes were spun at 1200 g for 10 minutes. The interphase was collected and washed twice in 1×PBS. CD4+ T cells were isolated from the PBMCs using EasySep CD4+ T cell enrichment kit (Stemcell Technologies). CD4+ T cells were cultured at $2\times10^6$ cells/mL in RPMI+10% FCS plus 2 µg/mL PHA (Sigma) and 20 IU/mL recombinant human IL-2 (Proleukin®, Prometheus) in 6-well plates for 72 hours.

Biocoat T cell activation control plates-96-well plates (Corning) were coated with 2 µg/mL goat anti-mouse IgG Fc-specific (Jackson ImmunoResearch) and 2 µg/mL goat anti-human IgG-Fc specific (Jackson ImmunoResearch) in 100 μL/well PBS overnight at 4° C. Plates were blocked with 200 μL/well of 1% BSA (Rockland) in PBS for 30 minutes at room temp. Plates were washed twice with 200 μL/well PBS. 4 ng/mL of anti-human CD3 OKT3 (eBioscience) was added in 100 μL/well PBS and incubated for 90 minutes at 37° C. Plates were washed twice with 200 μL/well PBS. A 3-fold dilution series of anti-OX40 antibody and isotype control monoclonal antibody starting at 5 μg/mL was added to the plates in 100 μL PBS. The plates were incubated for 90 minutes at 37° C. Plates were washed twice with 200 μL/well PBS. The washed PHA and IL-2 activated CD4+ T cells ($2\times10^5$) were added to each well.

After 48 hours of culture at 37° C., 30 μL of supernatant from each duplicate was pooled for IFN-γ analysis with Luminex (Millipore) and analyzed on Bioplex Manager 6.0 (BioRad). Plates were pulsed with 0.25 μCi $^3$H-thymidine (Perkin Elmer) overnight and harvested the following morning on Filtermats (Perkin Elmer) with 5 mL Ultima Gold Scintillation fluid (Perkin Elmer). Filtermats were counted on 1450 Microbeta Wallac Trilux counter (PerkinElmer).

8.1.13. Human Regulatory T Cell Suppression Assays

Fresh peripheral blood mononuclear cells (PBMCs) were obtained from AllCells or Stemcell Technologies. Cells were spun down, the cell pellet was resuspended with 1×PBS and spun down once again at 1200 rpm for 10 minutes at room temperature. Supernatants were removed and cells were then resuspended with RoboSep buffer (Stemcell Technologies). Cell viability and cell count were determined using the Vi-Cell XR cell Counter Beckman Coulter. 100-150 million cells were set aside for CD4+ T cell enrichment using Stemcell EasySep Human CD4+ T cell Enrichment Kit. The enriched CD4+ T cells were then depleted of CD25+ cells using Stemcell EasySep Human CD25+ Selection kit. This process resulted in purified CD4+/CD25− responder T cells (Tresp). Residual PBMC were used for isolating regulatory T cells (Treg) following instructions from the Stemcell EasySep Human CD4+/CD127low/CD49d—Regulatory T cell Enrichment Kit. After isolation of CD4+/CD25− Tresp and Treg, cells were resuspended with RPMI 1640 with 10% heat inactivated FBS and 0.01 mM 2-Mercaptoethanol at $1\times10^6$ cells/mL and $5\times10^5$ cells/mL respectively.

Treg Suppression assay was set up using two different ratios of Tresp to Treg at 2:1 and 4:1. For a 2:1 ratio, $5\times10^4$ Tresp cells and $2.5\times10^4$ Treg cells were added to 96-well U-bottom plates. For a 4:1 ratio, $5\times10^4$ Tresp cells and $1.25\times10^4$ Treg cells were added to the 96-wells plate. Treg Suppression Inspector bead reagent (Miltenyi Biotec) was also added to wells at 1:1 bead-to-cell ratio for stimulation. Anti-OX40 antibody and isotype control human $IgG_1$ were tested in triplicate at 10 μg/mL final concentration in the absence or presence of $F(ab')_2$ goat anti-human (GxHu) IgG, Fc specific (Jackson ImmunoResearch) at 1:4 ratio. Plates were incubated at 37° C. in 5% $CO_2$ for four days. Plates were treated with 1 μCi/well $^3$H-thymidine and further incubated for another 16 hours at 37° C. in 5% $CO_2$. After incubation, plates were harvested and proliferation measured using Ultima Gold Scintillation fluid (Perkin Elmer) and the 1450 Microbeta Wallac Trilux scintillation counter (PerkinElmer).

8.1.14. Human Immune Cell-Engrafted PC-3 Mouse Tumor Model

On the day of inoculation, human T cells, autologous human moDC (monocyte-derived dendritic cells) and PC-3 cells were counted by Vi-Cell XR (Beckman Coulter) and combined to deliver a subcutaneous injection of $1\times10^7$ PC-3, $1\times10^6$ T cells and $5\times10^5$ moDC per NSG mice (NOD.Cg-Prkdc$^{scid}$ Il2rg$^{tm1Wjl}$/SzJ mouse) in 100 μL Dulbecco's Phosphate Buffered Saline (DPBS) (GE Lifesciences). Treatment groups (n=8 mice/group) of 10 mg/kg isotype control monoclonal antibody and 10 mg/kg Hu3738 were prepared in 200 μL DPBS for intraperitoneal injection. A single antibody dose was injected at the time of cell-mixture inoculation. Measurement of tumor growth was assessed by standard caliper measurement and tumor growth volume was calculated (Length×width×height/2).

8.1.15. Human PBMC GVHD Model in NSG Mice

Human peripheral blood mononuclear cells (PBMCs) were purchased from AllCells (Oakland, Calif.). Immunodeficient NSG mice (NOD.Cg-Prkdc$^{scid}$ Il2rg$^{tm1Wjl}$/SzJ) were inoculated with $2\times10^7$ human PBMC intraperitoneally on day 1. Anti-OX40 antibody Hu3738 or isotype control was administered intraperitoneally once a week starting on day 1. Once mice exhibited behavioral signs of graft-versus-host disease (GVHD) (e.g., hunched posture, ruffled fur), serum samples were obtained, and levels of cytokines in the serum were determined using a Luminex bead array assay (Millipore).

Example 2

Generation and Humanization of Mouse Anti-OX40 Antibodies

Mice were immunized according to the methods known in the art (E. Harlow, D. Lane. Antibody: A Laboratory Manual, (Cold Spring Harbor Laboratory Press, Cold Spring Harbor, N.Y., 1998)). Isotype of each monoclonal antibody was determined using the Mouse Isotyping kit (Roche). Hybridoma clones producing antibodies of interest were purified and further characterized for affinity by surface plasmon resonance and for ligand competition by FACS.

Cloning and construction of the expression vector were accomplished by methods known in the art for expression of recombinant monoclonal antibodies.

Humanization of the antibody V region was carried out as outlined by Queen, C. et al. (Proc. Natl. Acad. Sci. USA, 1989; 86:10029-10033). The canonical structures of the CDRs were determined according to Huang et al. (Methods, 2005; 36:35-42). Human variable germline sequences with the same or most similar CDR canonical structures were identified, and appropriate human $V_H$, $V_L$, and J segment sequences were selected to provide the frameworks for the anti-OX40 variable region. At framework positions in which the computer model suggested significant contact with the CDRs, the amino acids from the murine anti-OX40 V regions were substituted for the original human framework amino acids (back-mutations).

Anti-OX40 mouse antibodies Mu3726, Mu3738, Mu3739, and Mu3741 were humanized according to the method described above. The humanized version of Mu3726 $V_H$ was Hu3726 $V_H$.1a which had human $V_H$4-28 framework regions, with seven back mutations of I48M, V67I, M69I, V71R, F78V, A93V, and R94K. Hu3726 $V_H$.1a was combined with its respective humanized light chain Hu3726 $V_L$.1b which had human VK1-39 framework regions, with two back mutations of Y48F and F71Y. The humanized version of Mu3738 $V_H$ was Hu3738 $V_H$.1b which had human $V_H$ 3-7 framework regions, with one back mutation of W47L. Hu3738 $V_H$.1b was combined with its respective humanized light chain Hu3738 $V_L$.1 which had human VK4-1 framework regions and no back mutations. The humanized version of Mu3739 $V_H$ was Hu3739 $V_H$.1b which had human $V_H$1-69 framework regions, with four back mutations of M48I, V67A, E73T, and S76N. Hu3739 $V_H$.1b was combined with its respective humanized light chain Hu3739 $V_L$.1b which had human VK1-39 framework regions, with two back mutations of V58L and F71Y. The humanized version of Mu3741 $V_H$ was Hu3741 $V_H$.2b which had human $V_H$3-66 framework regions, with seven back mutations of A24V, V48L, S49G, F67L, R71K, N76S, and L78V. Hu3741 $V_H$0.2b was combined with its respective humanized light chain Hu3741 $V_L$.1c which had human VK1-39 framework regions, with two back mutations of Y36F and F71Y.

Example 3

Binding Affinity of the Anti-OX40 Antibodies

Table 3-1 below shows in vitro binding affinity data of exemplary anti-OX40 antibody Hu3738, or literature anti-OX40 antibodies 11D4 or 18D8 described in U.S. Pat. No. 7,960,515. Each of 11D4 and 18D8 is a human $IgG_1$, with a light kappa region.

As used herein, 11D4 has a $V_H$ with amino acid sequence according to:

(SEQ ID NO: 61)
EVQLVESGGGLVQPGGSLRLSCAASGFTFSSYSMNWVRQAPGKGLEWVSY

ISSSSSTIDYADSVKGRFTISRDNAKNSLYLQMNSLRDEDTAVYYCARES

GWYLFDYWGQGTLVTVSS,
and a $V_L$ with amino acid sequence according to:

(SEQ ID NO: 62)
DIQMTQSPSSLSASVGDRVTITCRASQGISSWLAWYQQKPEKAPKSLIY

AASSLQSGVPSRFSGSGSGTDFTLTISSLQPEDFATYYCQQYNSYPPT

FGGGTKVEIK.

18D8 has a $V_H$ with amino acid sequence according to:

(SEQ ID NO: 63)
EVQLVESGGGLVQPGRLSRLSCAASGFTFDDYAMHWVRQAPGKGLEWVS

GISWNSGSIGYADSVKGRFTISRENAKNSLYLQMNSLRAEDTALYYCAK

DQSTADYYFYYGMDVWGQGTTVTVSS, and a $V_L$ with amino acid sequence according to:

(SEQ ID NO: 64)
EIVVTQSPATLSLSPGERATLSCRASQSVSSYLAWYQQKPGQAPRLLIY

DASNRATGIPARFSGSGSGTDFTLTISSLEPEDFAVYYCQQRSNWPTG

QGTKVEIK.

Hu3738 exhibited potent binding properties to human OX40 by surface plasmon resonance, or in transfected Jurkat NF-κB reporter cells expressing human OX40 as measured in the assays of Example 1, and higher binding affinity by SPR as compared with Hu3739 or Hu3741.

TABLE 3-1

Binding Properties of Exemplary Antibodies against Human OX40

| Antibody | $K_D$ (M)* | $k_d$ (1/sec)* | Jurkat cell surface binding $EC_{50}$ (ng/mL) |
|---|---|---|---|
| 11D4 | 1.6E−09 | 2.7E−04 | 55 |
| 18D8 | 9.1E−09 | 1.1E−01 | 258 |
| Hu3738 | 4.2E−08 | 4.2E−02 | 75 |
| Hu3739 | 3.6E−07 | 1.6E−02 | N/A |
| Hu3741 | 3.0E−06 | 3.1E−01 | N/A |

*as determined by surface plasmon resonance according to Example 1; exponential notation shown (e.g., 3.0E−09 = 3.0 × 10$^{-9}$); N/A = not available.

Exemplary anti-OX40 antibody Hu3738 exhibited cross reactivity against cynomolgus or rhesus monkey OX40, but did not demonstrate significant binding against mouse or rat OX40. The binding activity of Hu3738 to recombinant human or cynomolgus (cyno) OX40, or to cell-surface human or rhesus monkey OX40, as determined by the assays described in Example 1 is summarized in Table 3-2.

TABLE 3-2

Binding Properties of Hu3738 against Human, Cynomolgus or Rhesus OX40

| Assay | | $EC_{50}$ (nM) |
|---|---|---|
| ELISA | Human | 0.044 |
|  | Cyno | 0.039 |
| Jurkat | Human | 0.50 |
| NF-κB cell | rhesus | 2.1 |

Example 4

In Vitro Biological Activity of Anti-OX40 Antibody Hu3738

To assess binding of Hu3738 to endogenously expressed human OX40, both activated CD4+ T cells and unstimulated peripheral blood mononuclear cells (PBMC) were examined by flow cytometry. Table 4-1 summarizes the data for binding of Hu3738 on cell surface OX40 on CD3/CD28 bead activated human CD4+ T cells, or phytohemagglutinin (PHA) and interleukin-2 (IL-2) activated cynomolgus monkey CD4+ T cells, according to the assays described in Example 1. As shown in Table 4-1, Hu3738 potently bound to OX40 on activated CD4+ T cells in human and cynomolgus T cell cultures.

TABLE 4-1

CD4+ T cell Binding of Exemplary Antibody Hu3738

| OX40 Species | $EC_{50}$ (nM) |
|---|---|
| Human | 0.053 |
| Cynomolgus | 0.024 |

The subnanomolar binding of human OX40 by Hu3738 afforded functional activation as demonstrated by increased proliferation of human peripheral blood CD4+ T cells and enhanced interferon-γ production by human CD4+ T cells after in vitro treatment with Hu3738 according to the assays described in Section 8.1.12 (FIGS. 1A, 1B). As shown in a typical experiment depicted in FIG. 1A, Hu3738 effected an increased proliferation of human peripheral blood CD4+ T cells of from about 1.5- to about 6-fold as compared to isotype control huIgG$_1$, which was comparable or greater than the increase in proliferation observed when T cells were dosed with an equivalent amount of literature anti-OX40 antibody 11D4 or 18D8. Hu3738 showed EC$_{50}$=0.11 nM (16 ng/mL) in an average of runs from eight donors.

FIG. 1C shows that proliferation of human peripheral blood CD4+ T cells after in vitro treatment with Hu3738 was similar to literature anti-OX40 antibody 1A7 over a broad range of antibody concentrations from about 0.001 to about 1 µg/mL, when each was tested according to the T cell proliferation assay described in Section 8.1.12.

Antibody 1A7 described in US publication no. 2015/0307617 is a human IgG$_1$ with kappa light chains, having a V$_H$ amino acid sequence according to:

(SEQ ID NO: 69)
EVQLQQSGPELVKPGASVKISCKASGYTFTDSYMSWVKQSHGKTLEWIG

DMYPDNGDSSYNQKFREKVTLTVDKSSTTAYMEFRSLTSEDSAVYYCVL

APRWYFSVWGTGTTVTVSS, and
a V$_L$ amino acid sequence according to:

(SEQ ID NO: 70)
DIQMTQTTSSLSASLGDRVTISCRASQDISNYLNWYQQKPDGTVKLLIYY

TSRLRSGVPSRFSGSGSGKDYFLTISNLEQEDVAAYFCQQGHTLPPTFGG

GTKLEIK.

As shown in a typical experiment depicted in FIG. 1B, IFN-γ production increased in human CD4+ T cells from about 2- to about 10-fold when treated with Hu3738 across the concentration range tested. With regard to IFN-γ production, Hu3738 exhibited EC$_{50}$=0.16 nM (24 ng/mL) in an average of runs from nine donors. Literature anti-OX40 antibodies 11D4 and 18D8 also demonstrated a similar effect on IFN-γ production under these assay conditions.

FIG. 1D shows that Hu3738 effects a higher IFN-γ production increase in human CD4+ T cells as compared with literature anti-OX40 antibody 1A7, when each was tested according to the T cell IFN-γ production assay described in Section 8.1.12.

In addition to the downstream signaling activation effects in increasing proliferation of CD4+ T cells and enhancing production of IFN-γ, the exemplary anti-OX40 antibody Hu3738 also inhibited human T regulatory cell activity in vitro, suggesting that T regulatory cells within a solid tumor, which can inhibit an immunological response by the body to attack the tumor, may be suppressed with administration of Hu3738.

The effect of Hu3738 on T regulatory activity was assessed in vitro according to the assay described in Section 8.1.13. Autologous CD4+/CD25− T responder (Tresp) cells were co-cultured with CD4+/CD25+/CD127low T regulatory (Treg) cells and activator beads (Insp) at a 2:1 or a 4:1 Tresp:Treg ratio (FIGS. 2A, 2B). In the absence of Treg, the Tresp cells proliferated in response to the activator beads. In the presence of Treg, proliferation was inhibited. Inclusion of 10 µg/mL Hu3738 in the culture media had no impact on the Treg mediated suppression. The isotype control used for these T regulatory suppression assay was huIgG$_1$ with the constant region variants L234A and L235A. Separate experiments performed using the huIgG$_1$ isotype control with cross-linker showed no effect on the assay.

By contrast, in the presence of an exogenous cross-linker, Hu3738 resulted in complete restoration of the Tresp proliferation (FIGS. 2A and 2B). Hu3738 in the presence of cross-linker enhanced proliferation in this assay above the level of the Tresp response to the activator beads alone. This result suggested that OX40 signals may overcome T regulatory cell mediated suppression and may enhance antigen-specific responses consistent with results reported above.

ADCC activity mediated by Hu3738 was evaluated using a commercially available ADCC reporter assay as described in Section 8.1.9. This assay utilized engineered Jurkat cells expressing human FcγRIIIa and a nuclear factor of activated T cells (NFAT) reporter as the effector cells. HEK 293 cells expressing human OX40 were used as target cells, and the anti-OX40 antibody was expected to bind to OX40 expressed on the target cells. Additionally, the Fc region of Hu3738 was expected to bind to FcγRIIIa receptors on the cell surface of the reporter cells. These binding events would have resulted in multiple cross-linking of the two cell types leading to ADCC reporter activity activation, an effect that was measured through luminescence readout as a result of the NFAT pathway activation. Compared to isotype control, Hu3738 increased ADCC reporter activity, with an EC$_{50}$=0.51 nM (77 ng/mL).

Example 5

Epitope Classification of Exemplary Anti-OX40 Antibodies 8.5.1. Binding of Hu3738 with Human/Mouse Chimeric OX40

Soluble OX40L blocked Hu3738 binding to OX40 with an IC$_{50}$=67 pM (10 ng/mL) in a human OX40-expressing Jurkat cell assay described in Section 8.1.5 (FIG. 3), suggesting that Hu3738 bound to human OX40 in the ligand binding region of the molecule.

For more detailed epitope mapping of Hu3738 antibody binding, a series of cell lines expressing human/mouse cysteine-rich domain (CRD)-swapped OX40 molecules were created. This method is based on the observation that Hu3738 does not bind to mouse OX40 (FIG. 4B). A sequence alignment of human OX40 (SEQ ID NO:1) with mouse OX40 (SEQ ID NO:3) is shown in FIG. 4A. From the analysis of the sequences, a series of 293s transfectants expressing chimeric versions of the human OX40 receptor with swapped-in mouse CRD sequences were generated and stained with Hu3738.

The amino acid sequences (including signal sequences) of the human-mouse OX40 receptor chimeras, with murine swapped-in regions indicated as underline, are as follows. The human OX40 chimera with murine CRDI replacing human CRDI has an amino acid sequence according to:

(SEQ ID NO: 5)
MCVGARRLGRGPCAALLLLGLGLSTVTGL<u>NCVKHTYPSGHKCCRECQPGH</u>

<u>GMVSRCDHTRDTLCHPCGPGFYNDVVSSKPCKPCTWCNLRSGSERKQLCT</u>

ATQDTVCRCRAGTQPLDSYKPGVDCAPCPPGHFSPGDNQACKPWTNCTLA

GKHTLQPASNSSDAICEDRDPPATQPQETQGPPARPITVQPTEAWPRTSQ

GPSTRPVEVPGGRAVAAILGLGLVLGLLGPLAILLALYLLRRDQRLPPDA

HKPPGGGSFRTPIQEEQADAHSTLAKI, the human OX40 chimera with murine CRDII replacing human CRDII has an amino acid sequence according to:

(SEQ ID NO: 6)
MCVGARRLGRGPCAALLLLGLGLSTVTGLHCVGDTYPSNDRCCHECRPGN

GMVSRCSRSQNTVCRPCETGFYNEAVNYDTCKQCTQCNHRSGSELKQNCT

PTQDTVCRCRAGTQPLDSYKPGVDCAPCPPGHFSPGDNQACKPWTNCTLA

GKHTLQPASNSSDAICEDRDPPATQPQETQGPPARPITVQPTEAWPRTSQ

GPSTRPVEVPGGRAVAAILGLGLVLGLLGPLAILLALYLLRRDQRLPPDA

HKPPGGGSFRTPIQEEQADAHSTLAKI, the human OX40 chimera with murine CRDIII replacing human CRDIII has an amino acid sequence according to:

(SEQ ID NO: 7)
MCVGARRLGRGPCAALLLLGLGLSTVTGLHCVGDTYPSNDRCCHECRPGN

GMVSRCSRSQNTVCRPCGPGFYNDVVSSKPCKPCTWCNLRSGSERKQLCT

ATQDTVCRCRPGTQPRQDSGYKLGVDCVPCPPGHFSPGDNQACKPWTNCT

LAGKHTLQPASNSSDAICEDRDPPATQPQETQGPPARPITVQPTEAWPRT

SQGPSTRPVEVPGGRAVAAILGLGLVLGLLGPLAILLALYLLRRDQRLPP

DAHKPPGGGSFRTPIQEEQADAHSTLAKI, the human OX40 chimera with murine CRDIV replacing human CRDIV has an amino acid sequence according to:

(SEQ ID NO: 8)
MCVGARRLGRGPCAALLLLGLGLSTVTGLHCVGDTYPSNDRCCHECRPGN

GMVSRCSRSQNTVCRPCGPGFYNDVVSSKPCKPCTWCNLRSGSERKQLCT

ATQDTVCRCRAGTQPLDSYKPGVDCAPCPPGHFSPGNNQACKPWTNCTLS

GKQTRHPASDSLDAVCEDRDPPATQPQETQGPPARPITVQPTEAWPRTSQ

GPSTRPVEVPGGRAVAAILGLGLVLGLLGPLAILLALYLLRRDQRLPPDA

HKPPGGGSFRTPIQEEQADAHSTLAKI, and the human OX40 chimera with murine CRDII and CRDIII replacing human CRDII and CRDIII has an amino acid sequence according to:

(SEQ ID NO: 9)
MCVGARRLGRGPCAALLLLGLGLSTVTGLHCVGDTYPSNDRCCHECRPGN

GMVSRCSRSQNTVCRPCETGFYNEAVNYDTCKQCTQCNHRSGSELKQNCT

PTQDTVCRCRPGTQPRQDSGYKLGVDCVPCPPGHFSPGDNQACKPWTNCT

LAGKHTLQPASNSSDAICEDRDPPATQPQETQGPPARPITVQPTEAWPRT

SQGPSTRPVEVPGGRAVAAILGLGLVLGLLGPLAILLALYLLRRDQRLPP

DAHKPPGGGSFRTPIQEEQADAHSTLAKI.

Binding determination of Hu3738 to this series of chimeras was performed according to the assay described in Section 8.1.7 to localize the binding site to specific CRD regions. A loss in binding suggested which CRDs were critical for OX40 recognition by a particular antibody. In this instance, the absence of detectable binding to a specific CRD-swapped region in the mouse suggested the region of human OX40 receptor recognized by Hu3738. The anti-OX40 antibody Hu3738 was shown to lose binding when the human CRDII was replaced with the corresponding mouse CRDII, consistent with Hu3738 binding to CRDII of human OX40 (FIG. 4B).

8.5.2. Competition Assay with Exemplary Anti-OX40 Antibody Hu3738 Bound to Human OX40

Additional literature humanized anti-OX40 antibodies were generated to compare with the exemplary anti-OX40 antibodies of the disclosure. Antibodies 106-222 and 119-122, described in US publication no. 2013/0280275, are human IgG$_1$ with kappa light chains.

Antibody 106-222 has a V$_H$ amino acid sequence according to:

(SEQ ID NO: 65)
QVQLVQSGSELKKPGASVKVSCKASGYTFTDYSMHWVRQAPGQGLKWMGW

INTETGEPTYADDFKGRFVFSLDTSVSTAYLQISSLKAEDTAVYYCANPY

YDYVSYYAMDYWGQGTTVTVSS, and
a V$_L$ amino acid sequence according to:

(SEQ ID NO: 66)
DIQMTQSPSSLSASVGDRVTITCKASQDVSTAVAWYQQKPGKAPKLLIYS

ASYLYTGVPSRFSGSGSGTDFTFTISSLQPEDIATYYCQQHYSTPRTFGQ

GTKLEIK.

Antibody 119-122 has a V$_H$ amino acid sequence according to:

(SEQ ID NO: 67)
EVQLVESGGGLVQPGGSLRLSCAASEYEFPSHDMSWVRQAPGKGLELVAA

INSDGGSTYYPDTMERRFTISRDNAKNSLYLQMNSLRAEDTAVYYCARHY

DDYYAWFAYWGQGTMVTVSS, and
a V$_L$ amino acid sequence according to:

(SEQ ID NO: 68)
EIVLTQSPATLSLSPGERATLSCRASKSVSTSGYSYMHWYQQKPGQAPRL

LIYLASNLESGVPARFSGSGSGTDFTLTISSLEPEDFAVYYCQHSRELPL

TFGGGTKVEIK.

Binding of Hu3738 to cell-surface expressed OX40 was shown to be competitive with some but not all literature anti-OX40 antibodies by direct competition studies. As shown in FIG. 5, Jurkat-NF-κB-huOX40 cells treated with a dose titration of literature antibodies, then were subsequently subjected to 2 μg/mL of fluorescent ALEXA FLUOR® 647-labeled Hu3738 to determine binding competition. Analysis was performed by flow cytometry. Literature anti-OX40 antibodies 106-222 or 1A7 were competitive with Hu3738. However, antibodies 11D4, 18D8, or 119-122 did not compete with Hu3738 up to 100 μg/mL.

Example 6

OX40 Activation by Exemplary Anti-OX40 Antibody Hu3738

The Jurkat NF-κB cell data highlights the activating ability of exemplary anti-OX40 antibody Hu3738, even in the absence of a cross-linker (FIGS. 6A, 6B). As shown in FIG. 6A, the only anti-OX40 antibodies that demonstrated significant NF-κB signaling activity across the range of concentrations from about 0.001 to about 100 μg/mL antibody were Hu3738 and the corresponding murine Mu3738. Literature anti-OX40 antibodies 11D4, 18D8, 106-222, and 119-122 each lacked a significant NF-κB signaling effect up to about 100 μg/mL antibody.

The activity of Hu3738 in the absence of exogenous cross-linking contrasted to the lack of activity of other literature anti-OX40 antibodies under the same assay conditions. A summary of the NF-κB cell signaling data is shown in Tables 6-1 and 6-2. Notably, though Hu3738 competed to bind human OX40 with literature anti-OX40 antibodies 106-222 and 1A7, Hu3738 exhibited a different functional activity compared to each of the antibodies in the absence of a cross-linker.

TABLE 6-1

NF-κB signaling in Jurkat-NF-κB-huOX40 cells

| Antibody | EC$_{50}$ Without Cross-linker (nM) | EC$_{50}$ With Cross-linker (nM) |
|---|---|---|
| Hu3738 | 20 | 0.088 |
| 11D4 | NS* | 0.94 |
| 18D8 | NS* | 0.50 |
| 106-222 | NS* | 0.63 |
| 119-122 | NS* | 0.34 |
| Isotype | NS* | NS* |

*NS = no significant NF-κB signaling up to 100 μg/mL antibody; N/A = not available.

In addition to its ability to effect NF-κB signaling in the absence of exogenous cross-linker in the Jurkat-NF-κB-huOX40 cell, Hu3738 also demonstrated greater potency as measured by EC$_{50}$ with cross-linker, compared with literature anti-OX40 antibodies 11D4, 18D8, 106-222, and 119-122 (Table 6-1).

A side-by-side comparison of Hu3738 with 1A7 is shown in FIG. 6B and summarized in Table 6-2 below. In addition to the lack of NF-κB signaling in the absence of exogenous cross-linker in the Jurkat-NF-κB-huOX40 cell, each of the literature anti-OX40 antibodies described above also exhibited a lower EC$_{50}$ as compared with Hu3738.

TABLE 6-2

NF-κB signaling in Jurkat-NF-κB-huOX40 cells

| Antibody | EC$_{50}$ Without Cross-linker (nM) | EC$_{50}$ With Cross-linker (nM) |
|---|---|---|
| Hu3738 | 22 | 0.020 |
| 1A7 | NS* | 0.066 |
| Isotype | NS* | NS* |

*NS = no significant NF-κB signaling up to 100 μg/mL antibody.

Example 7

Anti-Tumor Activity of Hu3738 in Human Cell Adoptive Transfer Model in Mouse

Hu3738 demonstrated anti-tumor activity in an in vivo NSG mouse model after a single dose inoculation with human PC3 cells, T cells and autologous monocyte-derived dendritic cells (moDC) according to the protocol described in Section 8.1.14 (FIG. 7). On the day of inoculation, human T cells, moDC and PC3 cells were delivered by subcutaneous injection to each NSG mouse. Isotype control monoclonal antibody or Hu3738 (10 mg/kg) was each dosed intraperitoneally per animal in each treatment group (n=8), with the antibody dose injected at the time of inoculation. Measurement of tumor growth was assessed by standard caliper measurement and tumor growth volume was calculated (Length×width×height/2).

As shown in FIG. 7, Hu3738 significantly inhibited the growth of the PC3 tumor in NSG mice 17 days post-inoculation as compared with an equivalent dose of isotype control antibody.

Example 8

In Vivo Immune Activation in Human PBMC GVHD Model

NSG mice were inoculated with human PBMC intraperitoneally. The mice were then treated with 1 mg/kg Hu3738 or huIgG$_1$ isotype control q7d×4 (i.e., once every 7 days for a total of 4 doses), with the first dose at day 1 immediately after inoculation with human cells. On day 22, the mice were sacrificed and levels of cytokines in the serum were determined using a Luminex bead array assay (Millipore).

The results in FIG. 8 demonstrated that enhancement in interleukin-8 (IL-8), granulocyte macrophage colony-stimulating factor (GM-CSF), tumor necrosis factor alpha (TNF-α), and interferon-gamma (IFN-γ) was observed after dosing of anti-OX40 antibody Hu3738 as compared with isotype, suggestive of an increase in the immunological response in the mouse due to Hu3738.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An anti-OX40 antibody which comprises (i) a $V_H$ chain comprising three CDRs; and (ii) a $V_L$ chain comprising three CDRs, wherein:

$V_H$ CDR#1 is selected from:

(SEQ ID NO: 111) GYSIASGYYWN, (SEQ ID NO: 121) GFNIKDTYMH, (SEQ ID NO: 131) GFSLTSYGVH;

$V_H$ CDR#2 is selected from:

(SEQ ID NO: 112) YISYDGSNNYNPSLG, (SEQ ID NO: 122) RIDPANGNTKYDPKFQG, (SEQ ID NO: 132) VIWSGGSTDYNAAFIS;

$V_H$ CDR#3 is selected from:

(SEQ ID NO: 113) TLPYYFDY, (SEQ ID NO: 123) GGPAWFVY,

```
                                         (SEQ ID NO: 133)
                                EEFDY;

V_L CDR#1 is selected from:             (SEQ ID NO: 114)
                                RASQDISNYLN;

V_L CDR#2 is selected from:             (SEQ ID NO: 115)
                                YTSRLHS, (SEQ ID NO: 125)
                                YTSRLRS;

and V_L CDR#3 is selected from:         (SEQ ID NO: 116)
                                QQGNTLPLT, (SEQ ID NO: 126)
                                QQGNTLPWT, (SEQ ID NO: 136)
                                QQGYTLPPT.
```

2. The anti-OX40 antibody of claim 1, which is monoclonal.

3. The anti-OX40 antibody of claim 1, which is humanized.

4. The anti-OX40 antibody of claim 3, which comprises a V_H chain having an amino acid sequence according to:

```
                                                    (SEQ ID NO: 24)
EVQLQESGPGLVKPSDTLSLTCAVSGYSIASGYYWNWIRQPPGKGLEWM

GYISYDGSNNYNPSLGNRITISRDTSKNQVSLKLSSVTAVDTAVYYCVK

TLPYYFDYWGQGTTVTVSS;

(SEQ ID NO: 26)
EVQLVQSGAEVKKPGSSVKVSCKASGFNIKDTYMHWVRQAPGQGLEWIG

RIDPANGNTKYDPKFQGRATITADTSTNTAYMELSSLRSEDTAVYYCAR

GGPAWFVYWGQGTLVTVSS; or (SEQ ID NO: 28)
EVQLVESGGGLVQPGGSLRLSCAVSGFSLTSYGVHWVRQAPGKGLEWLG

VIWSGGSTDYNAAFISRLTISKDNSKSTVYLQMNSLRAEDTAVYYCARE

EFDYWGQGTTVTVSS;
``` and a V_L chain having an amino acid sequence according to:

```
                                                    (SEQ ID NO: 34)
DIQMTQTPSSLSASVGDRVTITCRASQDISNYLNWYQQKPGKAPKLLIF

YTSRLHSGVPSRFSGSGSGTDYTLTISSLQPEDFATYYCQQGNTLPLTF

GQGTKLEIK;

(SEQ ID NO: 36)
DIQMTQSPSSLSASVGDRVTITCRASQDISNYLNWYQQKPGKAPKLLIY

YTSRLRSGLPSRFSGSGSGTDYTLTISSLQPEDFATYYCQQGNTLPWTF

GGGTKVEIK; or (SEQ ID NO: 38)
DIQMTQSPSSLSASVGDRVTITCRASQDISNYLNWFQQKPGKAPKLLIY

YTSRLHSGVPSRFSGSGSGTDYTLTISSLQPEDFATYYCQQGYTLPPTF

GGGTKVEIK.
```

5. The anti-OX40 antibody of claim 3, which is an IgG.

6. The anti-OX40 antibody of claim 5, which is an IgG_1.

7. The anti-OX40 antibody of claim 3 comprising a kappa light chain constant region.

8. The anti-OX40 antibody of claim 1 which comprises a heavy chain having an amino acid sequence according to any one of SEQ ID NOS:43-48 ;and a light chain having an amino acid sequence according to any one of SEQ ID NOS:52-54.

9. A pharmaceutical composition comprising the anti-OX40 antibody of claim 1, and a pharmaceutically acceptable carrier.

10. A nucleic acid comprising a nucleotide sequence encoding an anti-OX40antibody which comprises (i) a V_H chain comprising three CDRs; and (ii) a V_L chain comprising three CDRs, wherein:

```
                                         (SEQ ID NO: 111)
V_H CDR#1 is selected from:     GYSIASGYYWN, (SEQ ID NO: 121)
                                GFNIKDTYMH, (SEQ ID NO: 131)
                                GFSLTSYGVH;

(SEQ ID NO: 112)
V_H CDR#2 is selected from:     YISYDGSNNYNPSLG, (SEQ ID NO: 122)
                                RIDPANGNTKYDPKFQG, (SEQ ID NO: 132)
                                VIWSGGSTDYNAAFIS;

(SEQ ID NO: 113)
V_H CDR#3 is selected from:     TLPYYFDY, (SEQ ID NO: 123)
                                GGPAWFVY, (SEQ ID NO: 133)
                                EEFDY;

(SEQ ID NO: 114)
V_L CDR#1 is selected from:     RASQDISNYLN;

(SEQ ID NO: 115)
V_L CDR#2 is selected from:     YTSRLHS, (SEQ ID NO: 125)
                                YTSRLRS;

(SEQ ID NO: 116)
and V_L CDR#3 is selected from: QQGNTLPLT, (SEQ ID NO: 126)
                                QQGNTLPWT, (SEQ ID NO: 136)
                                QQGYTLPPT.
```

11. A vector comprising the nucleic acid of claim 10.

12. A prokaryotic host cell transformed with the vector of claim 10.

13. A eukaryotic host cell transformed with the vector of claim 10.

14. The eukaryotic host cell of claim 13 which is a mammalian host cell.

15. A method of producing an anti-OX40 antibody, comprising: (a) culturing the host cell of claim 14 and (b) recovering the anti-OX40 antibody.

16. A method of treating a cancer, comprising administering to a patient in need thereof an effective amount of an anti-OX40 antibody which comprises (i) a V_H chain comprising three CDRs; and (ii) a V_L chain comprising three CDRs, wherein:

V_H CDR#1 is selected from:
GYSIASGYYWN, (SEQ ID NO: 111)
GFNIKDTYMH, (SEQ ID NO: 121)
GFSLTSYGVH; (SEQ ID NO: 131)

V_H CDR#2 is selected from:
YISYDGSNNYNPSLG, (SEQ ID NO: 112)
RIDPANGNTKYDPKFQG, (SEQ ID NO: 122)
VIWSGGSTDYNAAFIS; (SEQ ID NO: 132)

V_H CDR#3 is selected from:
TLPYYFDY, (SEQ ID NO: 113)
GGPAWFVY, (SEQ ID NO: 123)
EEFDY; (SEQ ID NO: 133)

V_L CDR#1 is selected from:
RASQDISNYLN; (SEQ ID NO: 114)

V_L CDR#2 is selected from:
YTSRLHS, (SEQ ID NO: 115)
YTSRLRS; (SEQ ID NO: 125)

and V_L CDR#3 is selected from:
QQGNTLPLT, (SEQ ID NO: 116)
QQGNTLPWT, (SEQ ID NO: 126)
QQGYTLPPT. (SEQ ID NO: 136)

17. The method of claim 16, wherein the cancer is selected from bladder cancer, breast cancer, head and neck cancer, gastric cancer, kidney cancer, liver cancer, lung cancer, ovarian cancer, skin cancer, and a tumor with evidence of DNA mismatch repair deficiency.

18. The method of claim 17, wherein the lung cancer is small cell lung cancer, non-small cell lung cancer, or mesothelioma.

* * * * *

UNITED STATES PATENT AND TRADEMARK OFFICE
CERTIFICATE OF CORRECTION

PATENT NO. : 10,040,864 B2
APPLICATION NO. : 15/908221
DATED : August 7, 2018
INVENTOR(S) : Fiona A. Harding It is certified that error appears in the above-identified patent and that said Letters Patent is hereby corrected as shown below:

In the Claims

Column 127, Line 54, cancel the text beginning with "1. An anti-OX40 antibody" through the text ending with "or mesothelioma." in Column 132, Line 23, and insert the following claims:

--1. An anti-OX40 antibody which comprises (i) a $V_H$ chain comprising three CDRs; and (ii) a $V_L$ chain comprising three CDRs, wherein:

| | | |
|---|---|---|
| $V_H$ CDR#1 has an amino acid sequence: | GFTFSRYGMS | (SEQ ID NO: 101), |
| $V_H$ CDR#2 has an amino acid sequence: | TINSNGGRTYYPDSVKG | (SEQ ID NO: 102), |
| $V_H$ CDR#3 has an amino acid sequence: | EGITTAYAMDY | (SEQ ID NO: 103), |
| $V_L$ CDR#1 has an amino acid sequence: | KASQSVDYDGDSYMH | (SEQ ID NO: 104), |
| $V_L$ CDR#2 has an amino acid sequence: | AASILES | (SEQ ID NO: 105), |
| and $V_L$ CDR#3 has an amino acid sequence: | QQSNEDPRT | (SEQ ID NO: 106). |

2. The anti-OX40 antibody of claim 1, which is monoclonal.

3. The anti-OX40 antibody of claim 1, which is humanized.

4. The anti-OX40 antibody of claim 3, which comprises a $V_H$ chain having an amino acid sequence according to:
EVQLVESGGGLVQPGGSLRLSCAASGFTFSRYGMSWVRQAPGKGLELVATINSNGGRTY YPDSVKGRFTISRDNAKNSLYLQMNSLRAEDTAVYYCAREGITTAYAMDYWGQGTTVT VSS (SEQ ID NO:22);
and a $V_L$ chain having an amino acid sequence according to:
DIVMTQSPDSLAVSLGERATINCKASQSVDYDGDSYMHWYQQKPGQPPKLLIYAASILE SGVPDRFSGSGSGTDFTLTISSLQAEDVAVYYCQQSNEDPRTFGGGTKVEIK (SEQ ID NO:32).

5. The anti-OX40 antibody of claim 3, which is an IgG.

Signed and Sealed this
Thirteenth Day of November, 2018

Andrei Iancu
*Director of the United States Patent and Trademark Office*

6. The anti-OX40 antibody of claim 5, which is an IgG$_1$.

7. The anti-OX40 antibody of claim 3 comprising a kappa light chain constant region.

8. The anti-OX40 antibody of claim 1 which comprises a heavy chain having an amino acid sequence according to SEQ ID NOS: 41 or 42; and a light chain having an amino acid sequence according to SEQ ID NO: 51.

9. The anti-OX40 antibody of claim 1 which has a $k_d$ against human OX40 (SEQ ID NO:1) of less than about 1 sec$^{-1}$.

10. The anti-OX40 antibody of claim 1 which has a $K_D$ against human OX40 (SEQ ID NO:1) of less than about 100 nM.

11. A pharmaceutical composition comprising the anti-OX40 antibody of claim 1, and a pharmaceutically acceptable carrier.

12. A nucleic acid comprising a nucleotide sequence encoding an anti-OX40 antibody which comprises (i) a $V_H$ chain comprising three CDRs; and (ii) a $V_L$ chain comprising three CDRs, wherein:

| | | |
|---|---|---|
| $V_H$ CDR#1 has an amino acid sequence: | GFTFSRYGMS | (SEQ ID NO:101), |
| $V_H$ CDR#2 has an amino acid sequence: | TINSNGGRTYYPDSVKG | (SEQ ID NO:102), |
| $V_H$ CDR#3 has an amino acid sequence: | EGITTAYAMDY | (SEQ ID NO:103), |
| $V_L$ CDR#1 has an amino acid sequence: | KASQSVDYDGDSYMH | (SEQ ID NO:104), |
| $V_L$ CDR#2 has an amino acid sequence: | AASILES | (SEQ ID NO:105), |
| and $V_L$ CDR#3 has an amino acid sequence: | QQSNEDPRT | (SEQ ID NO:106). |

13. A vector comprising the nucleic acid of claim 12.

14. A prokaryotic host cell transformed with the vector of claim 12.

15. A eukaryotic host cell transformed with the vector of claim 12.

16. The eukaryotic host cell of claim 15 which is a mammalian host cell.

17. A method of producing an anti-OX40 antibody, comprising: (a) culturing the host cell of claim 16 and (b) recovering the anti-OX40 antibody.

18. A method of treating a cancer, comprising administering to a patient in need thereof an effective amount of an anti-OX40 antibody which comprises (i) a $V_H$ chain comprising three CDRs; and (ii) a $V_L$ chain comprising three CDRs, wherein:

| | | |
|---|---|---|
| $V_H$ CDR#1 has an amino acid sequence: | GFTFSRYGMS | (SEQ ID NO:101), |
| $V_H$ CDR#2 has an amino acid sequence: | TINSNGGRTYYPDSVKG | (SEQ ID NO:102), |
| $V_H$ CDR#3 has an amino acid sequence: | EGITTAYAMDY | (SEQ ID NO:103), |
| $V_L$ CDR#1 has an amino acid sequence: | KASQSVDYDGDSYMH | (SEQ ID NO:104), |

| | | |
|---|---|---|
| V$_L$ CDR#2 has an amino acid sequence: | AASILES | (SEQ ID NO:105), |
| and V$_L$ CDR#3 has an amino acid sequence: | QQSNEDPRT | (SEQ ID NO:106). |

19. The method of claim 18, wherein the cancer is selected from bladder cancer, breast cancer, head and neck cancer, gastric cancer, kidney cancer, liver cancer, lung cancer, ovarian cancer, skin cancer, and a tumor with evidence of DNA mismatch repair deficiency.

20. The method of claim 19, wherein the lung cancer is small cell lung cancer, non-small cell lung cancer, or mesothelioma.--

SEQUENCE LISTING

<160> NUMBER OF SEQ ID NOS: 136

<210> SEQ ID NO 1
<211> LENGTH: 277
<212> TYPE: PRT
<213> ORGANISM: Homo sapiens

<400> SEQUENCE: 1

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275

<210> SEQ ID NO 2
<211> LENGTH: 277
<212> TYPE: PRT
<213> ORGANISM: Macaca fascicularis

<400> SEQUENCE: 2

Met Cys Val Gly Ala Arg Arg Leu Gly Arg Gly Pro Cys Ala Ala Leu
1               5                   10                  15

Leu Leu Leu Gly Leu Gly Leu Ser Thr Thr Ala Lys Leu His Cys Val
            20                  25                  30

Gly Asp Thr Tyr Pro Ser Asn Asp Arg Cys Cys Gln Glu Cys Arg Pro
            35                  40                  45

Gly Asn Gly Met Val Ser Arg Cys Asn Arg Ser Gln Asn Thr Val Cys
        50                  55                  60

Arg Pro Cys Gly Pro Gly Phe Tyr Asn Asp Val Val Ser Ala Lys Pro
65                  70                  75                  80

Cys Lys Ala Cys Thr Trp Cys Asn Leu Arg Ser Gly Ser Glu Arg Lys
                85                  90                  95
```

-continued

Gln Pro Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Thr Gln Pro
                165                 170                 175

Gln Glu Thr Gln Gly Pro Pro Ala Arg Pro Thr Thr Val Gln Pro Thr
            180                 185                 190

Glu Ala Trp Pro Arg Thr Ser Gln Arg Pro Ser Thr Arg Pro Val Glu
        195                 200                 205

Val Pro Arg Gly Pro Ala Val Ala Ala Ile Leu Gly Leu Gly Leu Ala
        210                 215                 220

Leu Gly Leu Leu Gly Pro Leu Ala Met Leu Leu Ala Leu Leu Leu Leu
225                 230                 235                 240

Arg Arg Asp Gln Arg Leu Pro Pro Asp Ala Pro Lys Ala Pro Gly Gly
                245                 250                 255

Gly Ser Phe Arg Thr Pro Ile Gln Glu Glu Gln Ala Asp Ala His Ser
            260                 265                 270

Ala Leu Ala Lys Ile
        275

<210> SEQ ID NO 3
<211> LENGTH: 272
<212> TYPE: PRT
<213> ORGANISM: Mus musculus

<400> SEQUENCE: 3

Met Tyr Val Trp Val Gln Gln Pro Thr Ala Leu Leu Leu Gly Leu
1               5                   10                  15

Thr Leu Gly Val Thr Ala Arg Arg Leu Asn Cys Val Lys His Thr Tyr
                20                  25                  30

Pro Ser Gly His Lys Cys Cys Arg Glu Cys Gln Pro Gly His Gly Met
            35                  40                  45

Val Ser Arg Cys Asp His Thr Arg Asp Thr Leu Cys His Pro Cys Glu
        50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
        130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val

```
                180                 185                 190
Trp Pro Arg Thr Ser Glu Leu Pro Ser Pro Thr Leu Val Thr Pro
            195                 200                 205
Glu Gly Pro Ala Phe Ala Val Leu Leu Gly Leu Gly Leu Gly Leu
            210                 215                 220
Ala Pro Leu Thr Val Leu Leu Ala Leu Tyr Leu Leu Arg Lys Ala Trp
225                 230                 235                 240
Arg Leu Pro Asn Thr Pro Lys Pro Cys Trp Gly Asn Ser Phe Arg Thr
                245                 250                 255
Pro Ile Gln Glu Glu His Thr Asp Ala His Phe Thr Leu Ala Lys Ile
            260                 265                 270
```

<210> SEQ ID NO 4
<211> LENGTH: 183
<212> TYPE: PRT
<213> ORGANISM: Homo sapiens

<400> SEQUENCE: 4

```
Met Glu Arg Val Gln Pro Leu Glu Glu Asn Val Gly Asn Ala Ala Arg
1               5                   10                  15
Pro Arg Phe Glu Arg Asn Lys Leu Leu Leu Val Ala Ser Val Ile Gln
            20                  25                  30
Gly Leu Gly Leu Leu Leu Cys Phe Thr Tyr Ile Cys Leu His Phe Ser
        35                  40                  45
Ala Leu Gln Val Ser His Arg Tyr Pro Arg Ile Gln Ser Ile Lys Val
    50                  55                  60
Gln Phe Thr Glu Tyr Lys Lys Glu Lys Gly Phe Ile Leu Thr Ser Gln
65                  70                  75                  80
Lys Glu Asp Glu Ile Met Lys Val Gln Asn Asn Ser Val Ile Ile Asn
                85                  90                  95
Cys Asp Gly Phe Tyr Leu Ile Ser Leu Lys Gly Tyr Phe Ser Gln Glu
            100                 105                 110
Val Asn Ile Ser Leu His Tyr Gln Lys Asp Glu Glu Pro Leu Phe Gln
        115                 120                 125
Leu Lys Lys Val Arg Ser Val Asn Ser Leu Met Val Ala Ser Leu Thr
    130                 135                 140
Tyr Lys Asp Lys Val Tyr Leu Asn Val Thr Thr Asp Asn Thr Ser Leu
145                 150                 155                 160
Asp Asp Phe His Val Asn Gly Gly Glu Leu Ile Leu Ile His Gln Asn
                165                 170                 175
Pro Gly Glu Phe Cys Val Leu
            180
```

<210> SEQ ID NO 5
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Cys Val Gly Ala Arg Arg Leu Gly Arg Gly Pro Cys Ala Ala Leu
1               5                   10                  15
Leu Leu Leu Gly Leu Gly Leu Ser Thr Val Thr Gly Leu Asn Cys Val
            20                  25                  30
Lys His Thr Tyr Pro Ser Gly His Lys Cys Cys Arg Glu Cys Gln Pro
```

```
                35                  40                  45
Gly His Gly Met Val Ser Arg Cys Asp His Thr Arg Asp Thr Leu Cys
    50                  55                  60

His Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 6
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Glu Thr Gly Phe Tyr Asn Glu Ala Val Asn Tyr Asp Thr
65                  70                  75                  80

Cys Lys Gln Cys Thr Gln Cys Asn His Arg Ser Gly Ser Glu Leu Lys
                85                  90                  95

Gln Asn Cys Thr Pro Thr Gln Asp Thr Val Cys Arg Cys Arg Ala Gly
            100                 105                 110
```

```
Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Ala Thr Gln Pro
                165                 170                 175

Gln Glu Thr Gln Gly Pro Pro Ala Arg Pro Ile Thr Val Gln Pro Thr
                180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 7
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Pro Gly
            100                 105                 110

Thr Gln Pro Arg Gln Asp Ser Gly Tyr Lys Leu Gly Val Asp Cys Val
        115                 120                 125

Pro Cys Pro Pro Gly His Phe Ser Pro Gly Asp Asn Gln Ala Cys Lys
        130                 135                 140

Pro Trp Thr Asn Cys Thr Leu Ala Gly Lys His Thr Leu Gln Pro Ala
145                 150                 155                 160

Ser Asn Ser Ser Asp Ala Ile Cys Glu Asp Arg Asp Pro Pro Ala Thr
                165                 170                 175

Gln Pro Gln Glu Thr Gln Gly Pro Pro Ala Arg Pro Ile Thr Val Gln
                180                 185                 190
```

```
Pro Thr Glu Ala Trp Pro Arg Thr Ser Gln Gly Pro Ser Thr Arg Pro
        195                 200                 205

Val Glu Val Pro Gly Gly Arg Ala Val Ala Ala Ile Leu Gly Leu Gly
    210                 215                 220

Leu Val Leu Gly Leu Leu Gly Pro Leu Ala Ile Leu Leu Ala Leu Tyr
225                 230                 235                 240

Leu Leu Arg Arg Asp Gln Arg Leu Pro Pro Asp Ala His Lys Pro Pro
            245                 250                 255

Gly Gly Gly Ser Phe Arg Thr Pro Ile Gln Glu Gln Ala Asp Ala
        260                 265                 270

His Ser Thr Leu Ala Lys Ile
        275
```

<210> SEQ ID NO 8
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asn Asn Gln Ala Cys Lys Pro Trp
    130                 135                 140

Thr Asn Cys Thr Leu Ser Gly Lys Gln Thr Arg His Pro Ala Ser Asp
145                 150                 155                 160

Ser Leu Asp Ala Val Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
```

```
                    260                 265                 270

Thr Leu Ala Lys Ile
        275

<210> SEQ ID NO 9
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Glu Thr Gly Phe Tyr Asn Glu Ala Val Asn Tyr Asp Thr
65                  70                  75                  80

Cys Lys Gln Cys Thr Gln Cys Asn His Arg Ser Gly Ser Glu Leu Lys
                85                  90                  95

Gln Asn Cys Thr Pro Thr Gln Asp Thr Val Cys Arg Cys Arg Pro Gly
            100                 105                 110

Thr Gln Pro Arg Gln Asp Ser Gly Tyr Lys Leu Gly Val Asp Cys Val
        115                 120                 125

Pro Cys Pro Pro Gly His Phe Ser Pro Gly Asp Asn Gln Ala Cys Lys
    130                 135                 140

Pro Trp Thr Asn Cys Thr Leu Ala Gly Lys His Thr Leu Gln Pro Ala
145                 150                 155                 160

Ser Asn Ser Ser Asp Ala Ile Cys Glu Asp Arg Asp Pro Pro Ala Thr
                165                 170                 175

Gln Pro Gln Glu Thr Gln Gly Pro Pro Ala Arg Pro Ile Thr Val Gln
            180                 185                 190

Pro Thr Glu Ala Trp Pro Arg Thr Ser Gln Gly Pro Ser Thr Arg Pro
        195                 200                 205

Val Glu Val Pro Gly Gly Arg Ala Val Ala Ala Ile Leu Gly Leu Gly
    210                 215                 220

Leu Val Leu Gly Leu Leu Gly Pro Leu Ala Ile Leu Leu Ala Leu Tyr
225                 230                 235                 240

Leu Leu Arg Arg Asp Gln Arg Leu Pro Pro Asp Ala His Lys Pro Pro
                245                 250                 255

Gly Gly Gly Ser Phe Arg Thr Pro Ile Gln Glu Glu Gln Ala Asp Ala
            260                 265                 270

His Ser Thr Leu Ala Lys Ile
        275

<210> SEQ ID NO 10

<400> SEQUENCE: 10

000

<210> SEQ ID NO 11
```

```
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Arg Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Glu Gly Ile Thr Thr Ala Tyr Ala Met Asp Tyr Trp Gly Gln
            100                 105                 110

Gly Thr Ser Val Thr Val Ser Ser
        115                 120
```

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Leu Val
        35                  40                  45

Ala Thr Ile Asn Ser Asn Gly Gly Arg Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Thr Thr Ala Tyr Ala Met Asp Tyr Trp Gly Gln
            100                 105                 110

Gly Thr Thr Val Thr Val Ser Ser
        115                 120
```

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Asn Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Ala Ser Gly
            20                  25                  30

Tyr Tyr Trp Asn Trp Ile Arg Gln Phe Pro Gly Asn Lys Leu Glu Trp
        35                  40                  45
```

Met Gly Tyr Ile Ser Tyr Asp Gly Ser Asn Asn Tyr Asn Pro Ser Leu
            50                  55                  60

Gly Asn Arg Ile Ser Ile Thr Arg Asp Thr Ser Lys Asn Gln Val Phe
65                  70                  75                  80

Leu Lys Leu Asn Ser Val Thr Thr Glu Asp Thr Ala Thr Tyr Tyr Cys
                85                  90                  95

Val Lys Thr Leu Pro Tyr Tyr Phe Asp Tyr Trp Gly Gln Gly Thr Thr
                100                 105                 110

Leu Thr Val Ser Ser
        115

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ala Ser Gly
                20                  25                  30

Tyr Tyr Trp Asn Trp Ile Arg Gln Pro Pro Gly Lys Gly Leu Glu Trp
            35                  40                  45

Met Gly Tyr Ile Ser Tyr Asp Gly Ser Asn Asn Tyr Asn Pro Ser Leu
            50                  55                  60

Gly Asn Arg Ile Thr Ile Ser Arg Asp Thr Ser Lys Asn Gln Val Ser
65                  70                  75                  80

Leu Lys Leu Ser Ser Val Thr Ala Val Asp Thr Ala Val Tyr Tyr Cys
                85                  90                  95

Val Lys Thr Leu Pro Tyr Tyr Phe Asp Tyr Trp Gly Gln Gly Thr Thr
                100                 105                 110

Val Thr Val Ser Ser
        115

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Asn Gly Asn Thr Lys Tyr Asp Pro Lys Phe
            50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Asp Val Tyr Tyr Cys
                85                  90                  95

```
Ala Arg Gly Gly Pro Ala Trp Phe Val Tyr Trp Gly Gln Gly Thr Leu
            100                 105                 110
Val Thr Val Ser Ala
        115

<210> SEQ ID NO 26
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Arg Ala Thr Ile Thr Ala Asp Thr Ser Asn Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Pro Ala Trp Phe Val Tyr Trp Gly Gln Gly Thr Leu
            100                 105                 110

Val Thr Val Ser Ser
        115

<210> SEQ ID NO 27
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Cys Cys Ala
            85                  90                  95

Arg Glu Glu Phe Asp Tyr Trp Gly Gln Gly Thr Thr Leu Thr Val Ser
            100                 105                 110

Ser

<210> SEQ ID NO 28
<211> LENGTH: 113
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Glu Glu Phe Asp Tyr Trp Gly Gln Gly Thr Thr Val Thr Val Ser
            100                 105                 110

Ser

<210> SEQ ID NO 29

<400> SEQUENCE: 29

000

<210> SEQ ID NO 30

<400> SEQUENCE: 30

000

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met His Trp Tyr Gln Gln Lys Pro Gly Gln Pro Pro
        35                  40                  45

Lys Leu Leu Ile Tyr Ala Ala Ser Ile Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110

<210> SEQ ID NO 32
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met His Trp Tyr Gln Gln Lys Pro Gly Gln Pro Pro
        35                  40                  45

Lys Leu Leu Ile Tyr Ala Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Arg Thr Phe Gly Gly Gly Thr Lys Val Glu Ile Lys
            100                 105                 110

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Phe Tyr Thr Ser Arg Leu His Ser Gly Val Pro Ser Arg Phe Ser Gly
    50                  55                  60

Gly Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Lys Leu Glu Leu Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
```

```
            35                  40                  45
Phe Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Leu
                85                  90                  95

Thr Phe Gly Gln Gly Thr Lys Leu Glu Ile Lys
                100                 105

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu Arg Ser Gly Leu Pro Ser Arg Phe Ser Gly
 50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
                100                 105

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Leu Pro Ser Arg Phe Ser Gly
 50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
                100                 105
```

```
<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Phe Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Pro
                85                  90                  95

Thr Phe Gly Gly Gly Thr Lys Leu Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Phe Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Tyr Thr Leu Pro Pro
                85                  90                  95

Thr Phe Gly Gly Gly Thr Lys Val Glu Ile Lys
            100                 105

<210> SEQ ID NO 39

<400> SEQUENCE: 39

000

<210> SEQ ID NO 40

<400> SEQUENCE: 40

000

<210> SEQ ID NO 41
```

```
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Leu Val
        35                  40                  45

Ala Thr Ile Asn Ser Asn Gly Gly Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Thr Thr Ala Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
```

```
                    370                 375                 380
Glu Ser Asn Gly Gln Pro Glu Asn Asn Tyr Lys Thr Thr Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 42
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Leu Val
        35                  40                  45

Ala Thr Ile Asn Ser Asn Gly Gly Arg Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Gly Ile Thr Thr Ala Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 43
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ala Ser Gly
            20                  25                  30

Tyr Tyr Trp Asn Trp Ile Arg Gln Pro Pro Gly Lys Gly Leu Glu Trp
        35                  40                  45

Met Gly Tyr Ile Ser Tyr Asp Gly Ser Asn Asn Tyr Asn Pro Ser Leu
    50                  55                  60

Gly Asn Arg Ile Thr Ile Ser Arg Asp Thr Ser Lys Asn Gln Val Ser
65                  70                  75                  80

Leu Lys Leu Ser Ser Val Thr Ala Val Asp Thr Ala Val Tyr Tyr Cys
                85                  90                  95

Val Lys Thr Leu Pro Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 44
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ala Ser Gly
            20                  25                  30

Tyr Tyr Trp Asn Trp Ile Arg Gln Pro Pro Gly Lys Gly Leu Glu Trp
        35                  40                  45

Met Gly Tyr Ile Ser Tyr Asp Gly Ser Asn Asn Tyr Asn Pro Ser Leu
    50                  55                  60

Gly Asn Arg Ile Thr Ile Ser Arg Asp Thr Ser Lys Asn Gln Val Ser
65                  70                  75                  80

Leu Lys Leu Ser Ser Val Thr Ala Val Asp Thr Ala Val Tyr Tyr Cys
                85                  90                  95

Val Lys Thr Leu Pro Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 45
<211> LENGTH: 447
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 45

Glu Val Gln Leu Val Gln Ser Gly Ala Glu Val Lys Lys Pro Gly Ser

-continued

```
1               5                   10                  15
Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Ile
            35                  40                  45

Gly Arg Ile Asp Pro Ala Asn Gly Asn Thr Lys Tyr Asp Pro Lys Phe
            50                  55                  60

Gln Gly Arg Ala Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Ala Trp Phe Val Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

```
His Asn His Tyr Thr Gln Lys Ser Leu Ser Leu Ser Pro Gly Lys
            435                 440                 445

<210> SEQ ID NO 46
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Arg Ala Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Ala Trp Phe Val Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
```

```
                    340                 345                 350
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 47
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Glu Glu Phe Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255
```

```
Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 48
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Glu Glu Phe Asp Tyr Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175
```

```
Ser Leu Ser Ser Val Thr Val Pro Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
            435                 440

<210> SEQ ID NO 49

<400> SEQUENCE: 49

000

<210> SEQ ID NO 50

<400> SEQUENCE: 50

000

<210> SEQ ID NO 51
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Ser Pro Asp Ser Leu Ala Val Ser Leu Gly
1               5                   10                  15
```

Glu Arg Ala Thr Ile Asn Cys Lys Ala Ser Gln Ser Val Asp Tyr Asp
            20                  25                  30

Gly Asp Ser Tyr Met His Trp Tyr Gln Gln Lys Pro Gly Gln Pro Pro
        35                  40                  45

Lys Leu Leu Ile Tyr Ala Ala Ser Ile Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                85                  90                  95

Glu Asp Pro Arg Thr Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 52
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 53
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Leu Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 54
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
```

```
    1               5                  10                 15
Asp Arg Val Thr Ile Thr Cys Arg Ala Ser Gln Asp Ile Ser Asn Tyr
            20                 25                 30

Leu Asn Trp Phe Gln Gln Lys Pro Gly Lys Ala Pro Lys Leu Leu Ile
            35                 40                 45

Tyr Tyr Thr Ser Arg Leu His Ser Gly Val Pro Ser Arg Phe Ser Gly
            50                 55                 60

Ser Gly Ser Gly Thr Asp Tyr Thr Leu Thr Ile Ser Ser Leu Gln Pro
65                         70                 75                 80

Glu Asp Phe Ala Thr Tyr Tyr Cys Gln Gln Gly Tyr Thr Leu Pro Pro
                    85                 90                 95

Thr Phe Gly Gly Gly Thr Lys Val Glu Ile Lys Arg Thr Val Ala Ala
                    100                105                110

Pro Ser Val Phe Ile Phe Pro Pro Ser Asp Glu Gln Leu Lys Ser Gly
                    115                120                125

Thr Ala Ser Val Val Cys Leu Leu Asn Asn Phe Tyr Pro Arg Glu Ala
            130                135                140

Lys Val Gln Trp Lys Val Asp Asn Ala Leu Gln Ser Gly Asn Ser Gln
145                 150                155                160

Glu Ser Val Thr Glu Gln Asp Ser Lys Asp Ser Thr Tyr Ser Leu Ser
                    165                170                175

Ser Thr Leu Thr Leu Ser Lys Ala Asp Tyr Glu Lys His Lys Val Tyr
            180                185                190

Ala Cys Glu Val Thr His Gln Gly Leu Ser Ser Pro Val Thr Lys Ser
                    195                200                205

Phe Asn Arg Gly Glu Cys
    210
```

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Gly Gly Ser Gly Gly Gly Ser Gly Gly Gly Gly Ser
1               5                   10                  15

<210> SEQ ID NO 61
<211> LENGTH: 118
<212> TYPE: PRT
<213> ORGANISM: Homo sapiens

<400> SEQUENCE: 61

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
        115

<210> SEQ ID NO 62
<211> LENGTH: 107
<212> TYPE: PRT
<213> ORGANISM: Homo sapiens

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 63
<211> LENGTH: 124
<212> TYPE: PRT
<213> ORGANISM: Homo sapiens

<400> SEQUENCE: 63
```

-continued

```
Glu Val Gln Leu Val Glu Ser Gly Gly Leu Val Gln Pro Gly Arg
1               5                   10                  15

Leu Ser Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120
```

<210> SEQ ID NO 64
<211> LENGTH: 106
<212> TYPE: PRT
<213> ORGANISM: Homo sapiens

<400> SEQUENCE: 64

```
Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

<210> SEQ ID NO 65
<211> LENGTH: 122
<212> TYPE: PRT
<213> ORGANISM: Homo sapiens

<400> SEQUENCE: 65

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

```
Ala Asn Pro Tyr Tyr Asp Tyr Val Ser Tyr Tyr Ala Met Asp Tyr Trp
                100                 105                 110

Gly Gln Gly Thr Thr Val Thr Val Ser Ser
            115                 120

<210> SEQ ID NO 66
<211> LENGTH: 107
<212> TYPE: PRT
<213> ORGANISM: Homo sapiens

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105

<210> SEQ ID NO 67
<211> LENGTH: 120
<212> TYPE: PRT
<213> ORGANISM: Homo sapiens

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 68
<211> LENGTH: 111
<212> TYPE: PRT
<213> ORGANISM: Homo sapiens

<400> SEQUENCE: 68

Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Lys Ser Val Ser Thr Ser
             20                  25                  30

Gly Tyr Ser Tyr Met His Trp Tyr Gln Gln Lys Pro Gly Gln Ala Pro
         35                  40                  45

Arg Leu Leu Ile Tyr Leu Ala Ser Asn Leu Glu Ser Gly Val Pro Ala
         50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
             85                  90                  95

Glu Leu Pro Leu Thr Phe Gly Gly Gly Thr Lys Val Glu Ile Lys
            100                 105                 110

<210> SEQ ID NO 69
<211> LENGTH: 117
<212> TYPE: PRT
<213> ORGANISM: Homo sapiens

<400> SEQUENCE: 69

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
             20                  25                  30

Tyr Met Ser Trp Val Lys Gln Ser His Gly Lys Thr Leu Glu Trp Ile
         35                  40                  45

Gly Asp Met Tyr Pro Asp Asn Gly Asp Ser Ser Tyr Asn Gln Lys Phe
         50                  55                  60

Arg Glu Lys Val Thr Leu Thr Val Asp Lys Ser Ser Thr Thr Ala Tyr
65                  70                  75                  80

Met Glu Phe Arg Ser Leu Thr Ser Glu Asp Ser Ala Val Tyr Tyr Cys
             85                  90                  95

Val Leu Ala Pro Arg Trp Tyr Phe Ser Val Trp Gly Thr Gly Thr Thr
            100                 105                 110

Val Thr Val Ser Ser
        115

<210> SEQ ID NO 70
<211> LENGTH: 107
<212> TYPE: PRT
<213> ORGANISM: Homo sapiens

<400> SEQUENCE: 70

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Arg Leu Arg Ser Gly Val Pro Ser Arg Phe Ser Gly
         50                  55                  60

Ser Gly Ser Gly Lys Asp Tyr Phe Leu Thr Ile Ser Asn Leu Glu Gln
65                  70                  75                  80

Glu Asp Val Ala Ala Tyr Phe Cys Gln Gln Gly His Thr Leu Pro Pro
             85                  90                  95

Thr Phe Gly Gly Gly Thr Lys Leu Glu Ile Lys
            100                 105

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82

```
<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93
```

000

<210> SEQ ID NO 94
<400> SEQUENCE: 94

000

<210> SEQ ID NO 95
<400> SEQUENCE: 95

000

<210> SEQ ID NO 96
<400> SEQUENCE: 96

000

<210> SEQ ID NO 97
<400> SEQUENCE: 97

000

<210> SEQ ID NO 98
<400> SEQUENCE: 98

000

<210> SEQ ID NO 99
<400> SEQUENCE: 99

000

<210> SEQ ID NO 100
<400> SEQUENCE: 100

000

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Thr Phe Ser Arg Tyr Gly Met Ser
1               5                   10

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Ile Asn Ser Asn Gly Gly Arg Thr Tyr Tyr Pro Asp Ser Val Lys
1               5                   10                  15

```
<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Glu Gly Ile Thr Thr Ala Tyr Ala Met Asp Tyr
1               5                   10

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Ala Ser Gln Ser Val Asp Tyr Asp Gly Asp Ser Tyr Met His
1               5                   10                  15

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Ala Ser Ile Leu Glu Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gln Ser Asn Glu Asp Pro Arg Thr
1               5

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000
```

<210> SEQ ID NO 110

<400> SEQUENCE: 110

000

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Tyr Ser Ile Ala Ser Gly Tyr Tyr Trp Asn
1               5                   10

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Tyr Ile Ser Tyr Asp Gly Ser Asn Asn Tyr Asn Pro Ser Leu Gly
1               5                   10                  15

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Thr Leu Pro Tyr Tyr Phe Asp Tyr
1               5

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ala Ser Gln Asp Ile Ser Asn Tyr Leu Asn
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Thr Ser Arg Leu His Ser
1               5

```
<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Gly Asn Thr Leu Pro Leu Thr
1               5

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Phe Asn Ile Lys Asp Thr Tyr Met His
1               5                   10

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Ile Asp Pro Ala Asn Gly Asn Thr Lys Tyr Asp Pro Lys Phe Gln
1               5                   10                  15

Gly

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 123

Gly Gly Pro Ala Trp Phe Val Tyr
1               5

<210> SEQ ID NO 124

<400> SEQUENCE: 124

000

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Tyr Thr Ser Arg Leu Arg Ser
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Gln Gly Asn Thr Leu Pro Trp Thr
1               5

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Gly Phe Ser Leu Thr Ser Tyr Gly Val His
1               5                   10

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Val Ile Trp Ser Gly Gly Ser Thr Asp Tyr Asn Ala Ala Phe Ile Ser
1               5                   10                  15

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Glu Phe Asp Tyr
1               5

<210> SEQ ID NO 134

<400> SEQUENCE: 134

000

<210> SEQ ID NO 135

<400> SEQUENCE: 135

000

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Gln Gly Tyr Thr Leu Pro Pro Thr
1               5
```